US009540428B2

(12) United States Patent
Hubbell et al.

(10) Patent No.: US 9,540,428 B2
(45) Date of Patent: Jan. 10, 2017

(54) EXTRACELLULAR MATRIX HEPARIN-BINDING DOMAINS

(71) Applicant: EPFL-TTO, Lausanne (CH)

(72) Inventors: Jeffrey A. Hubbell, Preverenges (CH); Mikael Martino, Nyon (CH); Laura De Laporte, De Pinte (BE); Jeffrey J. Rice, Port Salerno, FL (US); Federico Tortelli, Lausanne (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 9 days.

(21) Appl. No.: 13/933,448

(22) Filed: Jul. 2, 2013

(65) Prior Publication Data
US 2014/0011978 A1    Jan. 9, 2014

Related U.S. Application Data

(60) Provisional application No. 61/667,634, filed on Jul. 3, 2012.

(51) Int. Cl.
| | |
|---|---|
| C07K 14/315 | (2006.01) |
| C07K 14/47 | (2006.01) |
| C07K 14/75 | (2006.01) |
| C07K 14/78 | (2006.01) |

(52) U.S. Cl.
CPC ........ C07K 14/4718 (2013.01); C07K 14/75 (2013.01); C07K 14/78 (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,227,165 A | 7/1993 | Domb et al. | |
| 6,022,564 A | 2/2000 | Takechi et al. | |
| 6,090,925 A | 7/2000 | Woiszwillo et al. | |
| 6,224,794 B1 | 5/2001 | Amsden et al. | |
| 6,331,422 B1 | 12/2001 | Hubbell et al. | |
| 6,607,740 B1 | 8/2003 | Hubbell et al. | |
| 6,723,344 B2 | 4/2004 | Sakiyama-Elbert et al. | |
| 6,894,022 B1 | 5/2005 | Hubbell et al. | |
| 7,060,681 B2 | 6/2006 | Hubbell et al. | |
| 7,241,730 B2 | 7/2007 | Hubbell et al. | |
| 7,744,912 B1 | 6/2010 | Hubbell et al. | |
| 2003/0187232 A1* | 10/2003 | Hubbell et al. ............... 530/399 |
| 2007/0202178 A1 | 8/2007 | Schense et al. | |
| 2007/0264227 A1 | 11/2007 | Lutolf et al. | |
| 2008/0031899 A1 | 2/2008 | Reddy et al. | |
| 2009/0226435 A1* | 9/2009 | Khare .................. 424/133.1 |
| 2010/0003338 A1 | 1/2010 | Hubbell et al. | |
| 2010/0055189 A1 | 3/2010 | Hubbell et al. | |

FOREIGN PATENT DOCUMENTS

| | | |
|---|---|---|
| KR | 20060005595 | 1/2006 |
| WO | 03048185 | 6/2003 |
| WO | 2009038729 | 3/2009 |
| WO | WO 2009038729 A2 * | 3/2009 |

OTHER PUBLICATIONS

Simon et al., TAT-mediated intracellular protein delivery to primary brain cells is dependent on glycosaminoglycan expression, Biotechnol. Bioeng. 101:10-19 (2009).*
Sahni et al., "Vascular endothelial growth factor binds to fibrinogen and fibrin and stimulates endothelial cell proliferation," Blood 96:3772-3778 (2000).*
Martino et al., "Heparin-binding domain of fibrin(ogen) binds growth factors and promotes tissue repair when incorporated within a synthetic matrix," PNAS 110:4563-68 (Mar. 19, 2013).*
De Laporte et al. "Tenascin C Promiscuously Binds Growth Factors Via Its Fifth Fibronectin Type III-Like Domain", PLoS One, vol. 8(4), 9 Pages (Apr. 18, 2013).
Devalapally et al., "Poly(ethylene oxide)-Modified Poly(beta-amino ester) Nanoparticles as a pH-Sensitive System for Tumor-Targeted Delivery of Hydrophobic Drug: Part 3. Therapeutic Efficacy and Safety Studies in Ovarian Cancer Xenograft Model", Cancer Chemother Pharmacol, vol. 59:477-484 (Jul. 22, 2006).
Langer et al., "Optimization of the Preparation Process for Human Serum Albumin (HAS) Nanoparticles", International Journal of Pharmaceutics, vol. 257:169-180 (2003).
Lutolf et al., "Synthesis and Physicochemical Characterization of End-Linked Poly(ethylene glycol)-co-peptide Hydrogels Formed by Michael-Type Addition", Biomacromolecules, vol. 4:713-722 (2003).
Martino et al., "The 12th-14th Type III Repeats of Fibronectin Function as a Highly Promiscuous Growth Factor Binding Domain", The FASEB Journal,24:4711-4721 (Dec. 2010).
Tobio et al., "Stealth PLA-PEG Nanoparticles as Protein Carriers for Nasal Administration", Pharmaceutical Research, vol. 15(2)270-275 (1998).
International Search Report and Written Opinion from corresponding PCT Application No. PCT/EP2013/064023 mailed Dec. 17, 2013, 16 pages.

* cited by examiner

*Primary Examiner* — Julie Ha
*Assistant Examiner* — Kristina M Hellman
(74) *Attorney, Agent, or Firm* — Dardi & Herbert, PLLC; Curtis B. Herbert

(57) ABSTRACT

Heparin binding peptides derived from a Tenascin (TNC) III1-5 domain or a fibrinogen β15-66 domain have been found that bind certain cytokines with high affinity. Materials and methods for making compositions and devices using these peptides are disclosed.

14 Claims, 20 Drawing Sheets

SEQUENCE LISTING

```
<160> NUMBER OF SEQ ID NOS: 13

<210> SEQ ID NO 1
<211> LENGTH: 504
<212> TYPE: PRT
<213> ORGANISM: artificial
<220> FEATURE:
<223> OTHER INFORMATION: Tenascin III signal sequence with polyhistidine
      tag

<400> SEQUENCE: 1
```

-continued

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Ile Glu Gly Arg Asn Gln
            20                  25                  30

Glu Gln Val Ser Pro Leu Gly Gly Ser Glu Val Ser Pro Pro Lys Asp
        35                  40                  45

Leu Val Val Thr Glu Val Thr Glu Glu Thr Val Asn Leu Ala Trp Asp
    50                  55                  60

Asn Glu Met Arg Val Thr Glu Tyr Leu Val Val Tyr Thr Pro Thr His
65                  70                  75                  80

Glu Gly Gly Leu Glu Met Gln Phe Arg Val Pro Gly Asp Gln Thr Ser
                85                  90                  95

Thr Ile Ile Gln Glu Leu Glu Pro Gly Val Glu Tyr Phe Ile Arg Val
                100                 105                 110

Phe Ala Ile Leu Glu Asn Lys Lys Ser Ile Pro Val Ser Ala Arg Val
            115                 120                 125

Ala Thr Tyr Leu Pro Ala Pro Glu Gly Leu Lys Phe Lys Ser Ile Lys
130                 135                 140

Glu Thr Ser Val Glu Val Glu Trp Asp Pro Leu Asp Ile Ala Phe Glu
145                 150                 155                 160

Thr Trp Glu Ile Ile Phe Arg Asn Met Asn Lys Glu Asp Glu Gly Glu
                165                 170                 175

Ile Thr Lys Ser Leu Arg Arg Pro Glu Thr Ser Tyr Arg Gln Thr Gly
            180                 185                 190

Leu Ala Pro Gly Gln Glu Tyr Glu Ile Ser Leu His Ile Val Lys Asn
        195                 200                 205

Asn Thr Arg Gly Pro Gly Leu Lys Arg Val Thr Thr Thr Arg Leu Asp
210                 215                 220

Ala Pro Ser Gln Ile Glu Val Lys Asp Val Thr Asp Thr Thr Ala Leu
225                 230                 235                 240

Ile Thr Trp Phe Lys Pro Leu Ala Glu Ile Asp Gly Ile Glu Leu Thr
                245                 250                 255

Tyr Gly Ile Lys Asp Val Pro Gly Asp Arg Thr Thr Ile Asp Leu Thr
            260                 265                 270

Glu Asp Glu Asn Gln Tyr Ser Ile Gly Asn Leu Lys Pro Asp Thr Glu
        275                 280                 285

Tyr Glu Val Ser Leu Ile Ser Arg Arg Gly Asp Met Ser Ser Asn Pro
290                 295                 300

Ala Lys Glu Thr Phe Thr Thr Gly Leu Asp Ala Pro Arg Asn Leu Arg
305                 310                 315                 320

Arg Val Ser Gln Thr Asp Asn Ser Ile Thr Leu Glu Trp Arg Asn Gly
                325                 330                 335

Lys Ala Ala Ile Asp Ser Tyr Arg Ile Lys Tyr Ala Pro Ile Ser Gly
            340                 345                 350

Gly Asp His Ala Glu Val Asp Val Pro Lys Ser Gln Gln Ala Thr Thr
        355                 360                 365

Lys Thr Thr Leu Thr Gly Leu Arg Pro Gly Thr Glu Tyr Gly Ile Gly
370                 375                 380

Val Ser Ala Val Lys Glu Asp Lys Glu Ser Asn Pro Ala Thr Ile Asn
385                 390                 395                 400

Ala Ala Thr Glu Leu Asp Thr Pro Lys Asp Leu Gln Val Ser Glu Thr
                405                 410                 415
```

Ala Glu Thr Ser Leu Thr Leu Leu Trp Lys Thr Pro Leu Ala Lys Phe
            420                 425                 430

Asp Arg Tyr Arg Leu Asn Tyr Ser Leu Pro Thr Gly Gln Trp Val Gly
        435                 440                 445

Val Gln Leu Pro Arg Asn Thr Thr Ser Tyr Val Leu Arg Gly Leu Glu
    450                 455                 460

Pro Gly Gln Glu Tyr Asn Val Leu Leu Thr Ala Glu Lys Gly Arg His
465                 470                 475                 480

Lys Ser Lys Pro Ala Arg Val Lys Ala Ser Thr Glu Gln Ala Gly Gly
                485                 490                 495

Gly Ser His His His His His His
            500

<210> SEQ ID NO 2
<211> LENGTH: 68
<212> TYPE: PRT
<213> ORGANISM: artificial
<220> FEATURE:
<223> OTHER INFORMATION: GS linker, transglutaminase substrate, the Fg
      beta15-66, with a Histidine tag

<400> SEQUENCE: 2

Gly Ser Asn Gln Glu Gln Val Ser Pro Leu Gly His Arg Pro Leu Asp
1               5                   10                  15

Lys Lys Arg Glu Glu Ala Pro Ser Leu Arg Pro Ala Pro Pro Pro Ile
            20                  25                  30

Ser Gly Gly Gly Tyr Arg Ala Arg Pro Ala Lys Ala Ala Ala Thr Gln
        35                  40                  45

Lys Lys Val Glu Arg Lys Ala Pro Asp Ala Gly Gly Cys Gly His His
    50                  55                  60

His His His His
65

<210> SEQ ID NO 3
<211> LENGTH: 477
<212> TYPE: PRT
<213> ORGANISM: artificial
<220> FEATURE:
<223> OTHER INFORMATION: TG-FN III9-10/12/TNC III4-5, without C-terminal
      His tag

<400> SEQUENCE: 3

Asn Gln Glu Gln Val Ser Pro Leu Ala Gly Gly Leu Asp Ser Pro Thr
1               5                   10                  15

Gly Ile Asp Phe Ser Asp Ile Thr Ala Asn Ser Phe Thr Val His Trp
            20                  25                  30

Ile Ala Pro Arg Ala Thr Ile Thr Gly Tyr Arg Ile Arg His His Pro
        35                  40                  45

Glu His Phe Ser Gly Arg Pro Arg Glu Asp Arg Val Pro His Ser Arg
    50                  55                  60

Asn Ser Ile Thr Leu Thr Asn Leu Thr Pro Gly Thr Glu Tyr Val Val
65                  70                  75                  80

Ser Ile Val Ala Leu Asn Gly Arg Glu Glu Ser Pro Pro Leu Ile Gly
                85                  90                  95

Gln Gln Ser Thr Val Ser Asp Val Pro Arg Asp Leu Glu Val Val Ala
            100                 105                 110

Ala Thr Pro Thr Ser Leu Leu Ile Ser Trp Asp Ala Pro Ala Val Thr
        115                 120                 125

```
Val Arg Tyr Tyr Arg Ile Thr Tyr Gly Glu Thr Gly Gly Asn Ser Pro
    130                 135                 140

Val Gln Glu Phe Thr Val Pro Gly Ser Lys Ser Thr Ala Thr Ile Ser
145                 150                 155                 160

Gly Leu Lys Pro Gly Val Asp Tyr Thr Ile Thr Val Tyr Ala Val Thr
                165                 170                 175

Gly Arg Gly Asp Ser Pro Ala Ser Ser Lys Pro Ile Ser Ile Asn Tyr
            180                 185                 190

Arg Thr Glu Ile Asp Ser Ala Thr Ala Ile Pro Ala Pro Thr Asp Leu
        195                 200                 205

Lys Phe Thr Gln Val Thr Pro Thr Ser Leu Ser Ala Gln Trp Thr Pro
210                 215                 220

Pro Asn Val Gln Leu Thr Gly Tyr Arg Val Arg Val Thr Pro Lys Glu
225                 230                 235                 240

Lys Thr Gly Pro Met Lys Glu Ile Asn Leu Ala Pro Asp Ser Ser Ser
                245                 250                 255

Val Val Val Ser Gly Leu Met Val Ala Thr Lys Tyr Glu Val Ser Val
            260                 265                 270

Tyr Ala Leu Lys Asp Thr Leu Thr Ser Arg Pro Ala Gln Gly Val Val
        275                 280                 285

Thr Thr Gly Leu Asp Ala Pro Arg Asn Leu Arg Arg Val Ser Gln Thr
    290                 295                 300

Asp Asn Ser Ile Thr Leu Glu Trp Arg Asn Gly Lys Ala Ala Ile Asp
305                 310                 315                 320

Ser Tyr Arg Ile Lys Tyr Ala Pro Ile Ser Gly Gly Asp His Ala Glu
                325                 330                 335

Val Asp Val Pro Lys Ser Gln Gln Ala Thr Thr Lys Thr Thr Leu Thr
            340                 345                 350

Gly Leu Arg Pro Gly Thr Glu Tyr Gly Ile Gly Val Ser Ala Val Lys
        355                 360                 365

Glu Asp Lys Glu Ser Asn Pro Ala Thr Ile Asn Ala Ala Thr Glu Leu
    370                 375                 380

Asp Thr Pro Lys Asp Leu Gln Val Ser Glu Thr Ala Glu Thr Ser Leu
385                 390                 395                 400

Thr Leu Leu Trp Lys Thr Pro Leu Ala Lys Phe Asp Arg Tyr Arg Leu
                405                 410                 415

Asn Tyr Ser Leu Pro Thr Gly Gln Trp Val Gly Val Gln Leu Pro Arg
            420                 425                 430

Asn Thr Thr Ser Tyr Val Leu Arg Gly Leu Glu Pro Gly Gln Glu Tyr
        435                 440                 445

Asn Val Leu Leu Thr Ala Glu Lys Gly Arg His Lys Ser Lys Pro Ala
    450                 455                 460

Arg Val Lys Ala Ser Thr Glu Gln Ala Gly Gly Ser
465                 470                 475

<210> SEQ ID NO 4
<211> LENGTH: 474
<212> TYPE: PRT
<213> ORGANISM: artificial
<220> FEATURE:
<223> OTHER INFORMATION: TG-FN III9-10/TNC III3-5, without His tag

<400> SEQUENCE: 4

Asn Gln Glu Gln Val Ser Pro Leu Ala Gly Gly Leu Asp Ser Pro Thr
1               5                   10                  15
```

Gly Ile Asp Phe Ser Asp Ile Thr Ala Asn Ser Phe Thr Val His Trp
            20                  25                  30
Ile Ala Pro Arg Ala Thr Ile Thr Gly Tyr Arg Ile Arg His His Pro
        35                  40                  45
Glu His Phe Ser Gly Arg Pro Arg Glu Asp Arg Val Pro His Ser Arg
    50                  55                  60
Asn Ser Ile Thr Leu Thr Asn Leu Thr Pro Gly Thr Glu Tyr Val Val
65                  70                  75                  80
Ser Ile Val Ala Leu Asn Gly Arg Glu Glu Ser Pro Pro Leu Ile Gly
                85                  90                  95
Gln Gln Ser Thr Val Ser Asp Val Pro Arg Asp Leu Glu Val Val Ala
            100                 105                 110
Ala Thr Pro Thr Ser Leu Leu Ile Ser Trp Asp Ala Pro Ala Val Thr
        115                 120                 125
Val Arg Tyr Tyr Arg Ile Thr Tyr Gly Glu Thr Gly Gly Asn Ser Pro
    130                 135                 140
Val Gln Glu Phe Thr Val Pro Gly Ser Lys Ser Thr Ala Thr Ile Ser
145                 150                 155                 160
Gly Leu Lys Pro Gly Val Asp Tyr Thr Ile Thr Val Tyr Ala Val Thr
                165                 170                 175
Gly Arg Gly Asp Ser Pro Ala Ser Ser Lys Pro Ile Ser Ile Asn Tyr
            180                 185                 190
Arg Thr Thr Thr Arg Leu Asp Ala Pro Ser Gln Ile Glu Val Lys
        195                 200                 205
Asp Val Thr Asp Thr Thr Ala Leu Ile Thr Trp Phe Lys Pro Leu Ala
    210                 215                 220
Glu Ile Asp Gly Ile Glu Leu Thr Tyr Gly Ile Lys Asp Val Pro Gly
225                 230                 235                 240
Asp Arg Thr Thr Ile Asp Leu Thr Glu Asp Glu Asn Gln Tyr Ser Ile
                245                 250                 255
Gly Asn Leu Lys Pro Asp Thr Glu Tyr Glu Val Ser Leu Ile Ser Arg
            260                 265                 270
Arg Gly Asp Met Ser Ser Asn Pro Ala Lys Glu Thr Phe Thr Thr Gly
        275                 280                 285
Leu Asp Ala Pro Arg Asn Leu Arg Arg Val Ser Gln Thr Asp Asn Ser
    290                 295                 300
Ile Thr Leu Glu Trp Arg Asn Gly Lys Ala Ala Ile Asp Ser Tyr Arg
305                 310                 315                 320
Ile Lys Tyr Ala Pro Ile Ser Gly Gly Asp His Ala Glu Val Asp Val
                325                 330                 335
Pro Lys Ser Gln Gln Ala Thr Thr Lys Thr Thr Leu Thr Gly Leu Arg
            340                 345                 350
Pro Gly Thr Glu Tyr Gly Ile Gly Val Ser Ala Val Lys Glu Asp Lys
        355                 360                 365
Glu Ser Asn Pro Ala Thr Ile Asn Ala Ala Thr Glu Leu Asp Thr Pro
    370                 375                 380
Lys Asp Leu Gln Val Ser Glu Thr Ala Glu Thr Ser Leu Thr Leu Leu
385                 390                 395                 400
Trp Lys Thr Pro Leu Ala Lys Phe Asp Arg Tyr Arg Leu Asn Tyr Ser
                405                 410                 415
Leu Pro Thr Gly Gln Trp Val Gly Val Gln Leu Pro Arg Asn Thr Thr
            420                 425                 430
Ser Tyr Val Leu Arg Gly Leu Glu Pro Gly Gln Glu Tyr Asn Val Leu

```
                        435                 440                 445
Leu Thr Ala Glu Lys Gly Arg His Lys Ser Lys Pro Ala Arg Val Lys
    450                 455                 460

Ala Ser Thr Glu Gln Ala Gly Gly Ser
465                 470

<210> SEQ ID NO 5
<211> LENGTH: 654
<212> TYPE: PRT
<213> ORGANISM: artificial
<220> FEATURE:
<223> OTHER INFORMATION: FN III9-10/TNC III1-5, without His tag

<400> SEQUENCE: 5

Asn Gln Glu Gln Val Ser Pro Leu Ala Gly Leu Asp Ser Pro Thr
1               5                   10                  15

Gly Ile Asp Phe Ser Asp Ile Thr Ala Asn Ser Phe Thr Val His Trp
                20                  25                  30

Ile Ala Pro Arg Ala Thr Ile Thr Gly Tyr Arg Ile Arg His His Pro
            35                  40                  45

Glu His Phe Ser Gly Arg Pro Arg Glu Asp Arg Val Pro His Ser Arg
    50                  55                  60

Asn Ser Ile Thr Leu Thr Asn Leu Thr Pro Gly Thr Glu Tyr Val Val
65                  70                  75                  80

Ser Ile Val Ala Leu Asn Gly Arg Glu Glu Ser Pro Pro Leu Ile Gly
                85                  90                  95

Gln Gln Ser Thr Val Ser Asp Val Pro Arg Asp Leu Glu Val Val Ala
            100                 105                 110

Ala Thr Pro Thr Ser Leu Leu Ile Ser Trp Asp Ala Pro Ala Val Thr
    115                 120                 125

Val Arg Tyr Tyr Arg Ile Thr Tyr Gly Glu Thr Gly Gly Asn Ser Pro
130                 135                 140

Val Gln Glu Phe Thr Val Pro Gly Ser Lys Ser Thr Ala Thr Ile Ser
145                 150                 155                 160

Gly Leu Lys Pro Gly Val Asp Tyr Thr Ile Thr Val Tyr Ala Val Thr
                165                 170                 175

Gly Arg Gly Asp Ser Pro Ala Ser Ser Lys Pro Ile Ser Ile Asn Tyr
            180                 185                 190

Arg Thr Gly Gly Ser Glu Val Ser Pro Pro Lys Asp Leu Val Val Thr
    195                 200                 205

Glu Val Thr Glu Glu Thr Val Asn Leu Ala Trp Asp Asn Glu Met Arg
210                 215                 220

Val Thr Glu Tyr Leu Val Val Tyr Thr Pro Thr His Glu Gly Gly Leu
225                 230                 235                 240

Glu Met Gln Phe Arg Val Pro Gly Asp Gln Thr Ser Thr Ile Ile Gln
                245                 250                 255

Glu Leu Glu Pro Gly Val Glu Tyr Phe Ile Arg Val Phe Ala Ile Leu
            260                 265                 270

Glu Asn Lys Lys Ser Ile Pro Val Ser Ala Arg Val Ala Thr Tyr Leu
    275                 280                 285

Pro Ala Pro Glu Gly Leu Lys Phe Lys Ser Ile Lys Glu Thr Ser Val
290                 295                 300

Glu Val Glu Trp Asp Pro Leu Asp Ile Ala Phe Glu Thr Trp Glu Ile
305                 310                 315                 320

Ile Phe Arg Asn Met Asn Lys Glu Asp Glu Gly Glu Ile Thr Lys Ser
```

```
                325                 330                 335
Leu Arg Arg Pro Glu Thr Ser Tyr Arg Gln Thr Gly Leu Ala Pro Gly
            340                 345                 350

Gln Glu Tyr Glu Ile Ser Leu His Ile Val Lys Asn Asn Thr Arg Gly
        355                 360                 365

Pro Gly Leu Lys Arg Val Thr Thr Thr Arg Leu Asp Ala Pro Ser Gln
    370                 375                 380

Ile Glu Val Lys Asp Val Thr Asp Thr Thr Ala Leu Ile Thr Trp Phe
385                 390                 395                 400

Lys Pro Leu Ala Glu Ile Asp Gly Ile Glu Leu Thr Tyr Gly Ile Lys
                405                 410                 415

Asp Val Pro Gly Asp Arg Thr Thr Ile Asp Leu Thr Glu Asp Glu Asn
            420                 425                 430

Gln Tyr Ser Ile Gly Asn Leu Lys Pro Asp Thr Glu Tyr Glu Val Ser
        435                 440                 445

Leu Ile Ser Arg Arg Gly Asp Met Ser Ser Asn Pro Ala Lys Glu Thr
    450                 455                 460

Phe Thr Thr Gly Leu Asp Ala Pro Arg Asn Leu Arg Arg Val Ser Gln
465                 470                 475                 480

Thr Asp Asn Ser Ile Thr Leu Glu Trp Arg Asn Gly Lys Ala Ala Ile
                485                 490                 495

Asp Ser Tyr Arg Ile Lys Tyr Ala Pro Ile Ser Gly Gly Asp His Ala
            500                 505                 510

Glu Val Asp Val Pro Lys Ser Gln Gln Ala Thr Thr Lys Thr Thr Leu
        515                 520                 525

Thr Gly Leu Arg Pro Gly Thr Glu Tyr Gly Ile Gly Val Ser Ala Val
    530                 535                 540

Lys Glu Asp Lys Glu Ser Asn Pro Ala Thr Ile Asn Ala Ala Thr Glu
545                 550                 555                 560

Leu Asp Thr Pro Lys Asp Leu Gln Val Ser Glu Thr Ala Glu Thr Ser
                565                 570                 575

Leu Thr Leu Leu Trp Lys Thr Pro Leu Ala Lys Phe Asp Arg Tyr Arg
            580                 585                 590

Leu Asn Tyr Ser Leu Pro Thr Gly Gln Trp Val Gly Val Gln Leu Pro
        595                 600                 605

Arg Asn Thr Thr Ser Tyr Val Leu Arg Gly Leu Glu Pro Gly Gln Glu
    610                 615                 620

Tyr Asn Val Leu Leu Thr Ala Glu Lys Gly Arg His Lys Ser Lys Pro
625                 630                 635                 640

Ala Arg Val Lys Ala Ser Thr Glu Gln Ala Gly Gly Ser
                645                 650

<210> SEQ ID NO 6
<211> LENGTH: 246
<212> TYPE: PRT
<213> ORGANISM: artificial
<220> FEATURE:
<223> OTHER INFORMATION: FN III9-10/Fg beta 15-66, without His tag

<400> SEQUENCE: 6

Asn Gln Glu Gln Val Ser Pro Leu Ala Gly Gly Leu Asp Ser Pro Thr
1               5                   10                  15

Gly Ile Asp Phe Ser Asp Ile Thr Ala Asn Ser Phe Thr Val His Trp
            20                  25                  30

Ile Ala Pro Arg Ala Thr Ile Thr Gly Tyr Arg Ile Arg His His Pro
```

-continued

```
                35                  40                  45
Glu His Phe Ser Gly Arg Pro Arg Glu Asp Arg Val Pro His Ser Arg
 50                  55                  60
Asn Ser Ile Thr Leu Thr Asn Leu Thr Pro Gly Thr Glu Tyr Val Val
 65                  70                  75                  80
Ser Ile Val Ala Leu Asn Gly Arg Glu Glu Ser Pro Pro Leu Ile Gly
                 85                  90                  95
Gln Gln Ser Thr Val Ser Asp Val Pro Arg Asp Leu Glu Val Val Ala
            100                 105                 110
Ala Thr Pro Thr Ser Leu Leu Ile Ser Trp Asp Ala Pro Ala Val Thr
            115                 120                 125
Val Arg Tyr Tyr Arg Ile Thr Tyr Gly Glu Thr Gly Gly Asn Ser Pro
130                 135                 140
Val Gln Glu Phe Thr Val Pro Gly Ser Lys Ser Thr Ala Thr Ile Ser
145                 150                 155                 160
Gly Leu Lys Pro Gly Val Asp Tyr Thr Ile Thr Val Tyr Ala Val Thr
                165                 170                 175
Gly Arg Gly Asp Ser Pro Ala Ser Ser Lys Pro Ile Ser Ile Asn Tyr
            180                 185                 190
Arg Thr Gly His Arg Pro Leu Asp Lys Lys Arg Glu Glu Ala Pro Ser
            195                 200                 205
Leu Arg Pro Ala Pro Pro Ile Ser Gly Gly Gly Tyr Arg Ala Arg
210                 215                 220
Pro Ala Lys Ala Ala Ala Thr Gln Lys Lys Val Glu Arg Lys Ala Pro
225                 230                 235                 240
Asp Ala Gly Gly Cys Gly
                245

<210> SEQ ID NO 7
<211> LENGTH: 525
<212> TYPE: PRT
<213> ORGANISM: artificial
<220> FEATURE:
<223> OTHER INFORMATION: FN III9-10/12-14/Fg 15-66, without His tag

<400> SEQUENCE: 7

Asn Gln Glu Gln Val Ser Pro Leu Ala Gly Gly Leu Asp Ser Pro Thr
 1                5                  10                  15
Gly Ile Asp Phe Ser Asp Ile Thr Ala Asn Ser Phe Thr Val His Trp
                 20                  25                  30
Ile Ala Pro Arg Ala Thr Ile Thr Gly Tyr Arg Ile Arg His His Pro
             35                  40                  45
Glu His Phe Ser Gly Arg Pro Arg Glu Asp Arg Val Pro His Ser Arg
 50                  55                  60
Asn Ser Ile Thr Leu Thr Asn Leu Thr Pro Gly Thr Glu Tyr Val Val
 65                  70                  75                  80
Ser Ile Val Ala Leu Asn Gly Arg Glu Glu Ser Pro Pro Leu Ile Gly
                 85                  90                  95
Gln Gln Ser Thr Val Ser Asp Val Pro Arg Asp Leu Glu Val Val Ala
            100                 105                 110
Ala Thr Pro Thr Ser Leu Leu Ile Ser Trp Asp Ala Pro Ala Val Thr
            115                 120                 125
Val Arg Tyr Tyr Arg Ile Thr Tyr Gly Glu Thr Gly Gly Asn Ser Pro
130                 135                 140
Val Gln Glu Phe Thr Val Pro Gly Ser Lys Ser Thr Ala Thr Ile Ser
```

```
            145                 150                 155                 160
Gly Leu Lys Pro Gly Val Asp Tyr Thr Ile Thr Val Tyr Ala Val Thr
                165                 170                 175

Gly Arg Gly Asp Ser Pro Ala Ser Ser Lys Pro Ile Ser Ile Asn Tyr
                180                 185                 190

Arg Thr Glu Ile Asp Ser Ala Thr Ala Ile Pro Ala Pro Thr Asp Leu
                195                 200                 205

Lys Phe Thr Gln Val Thr Pro Thr Ser Leu Ser Ala Gln Trp Thr Pro
210                 215                 220

Pro Asn Val Gln Leu Thr Gly Tyr Arg Val Arg Val Thr Pro Lys Glu
225                 230                 235                 240

Lys Thr Gly Pro Met Lys Glu Ile Asn Leu Ala Pro Asp Ser Ser Ser
                245                 250                 255

Val Val Val Ser Gly Leu Met Val Ala Thr Lys Tyr Glu Val Ser Val
                260                 265                 270

Tyr Ala Leu Lys Asp Thr Leu Thr Ser Arg Pro Ala Gln Gly Val Val
                275                 280                 285

Thr Thr Leu Glu Asn Val Ser Pro Pro Arg Arg Ala Arg Val Thr Asp
290                 295                 300

Ala Thr Glu Thr Thr Ile Thr Ile Ser Trp Arg Thr Lys Thr Glu Thr
305                 310                 315                 320

Ile Thr Gly Phe Gln Val Asp Ala Val Pro Ala Asn Gly Gln Thr Pro
                325                 330                 335

Ile Gln Arg Thr Ile Lys Pro Asp Val Arg Ser Tyr Thr Ile Thr Gly
                340                 345                 350

Leu Gln Pro Gly Thr Asp Tyr Lys Ile Tyr Leu Tyr Thr Leu Asn Asp
                355                 360                 365

Asn Ala Arg Ser Ser Pro Val Val Ile Asp Ala Ser Thr Ala Ile Asp
                370                 375                 380

Ala Pro Ser Asn Leu Arg Phe Leu Ala Thr Thr Pro Asn Ser Leu Leu
385                 390                 395                 400

Val Ser Trp Gln Pro Pro Arg Ala Arg Ile Thr Gly Tyr Ile Ile Lys
                405                 410                 415

Tyr Glu Lys Pro Gly Ser Pro Arg Glu Val Val Pro Arg Pro Arg
                420                 425                 430

Pro Gly Val Thr Glu Ala Thr Ile Thr Gly Leu Glu Pro Gly Thr Glu
                435                 440                 445

Tyr Thr Ile Tyr Val Ile Ala Leu Lys Asn Asn Gln Lys Ser Glu Pro
450                 455                 460

Leu Ile Gly Arg Lys Lys Thr Phe Lys Gly His Arg Pro Leu Asp Lys
465                 470                 475                 480

Lys Arg Glu Glu Ala Pro Ser Leu Arg Pro Ala Pro Pro Ile Ser
                485                 490                 495

Gly Gly Gly Tyr Arg Ala Arg Pro Ala Lys Ala Ala Thr Gln Lys
                500                 505                 510

Lys Val Glu Arg Lys Ala Pro Asp Ala Gly Gly Cys Gly
515                 520                 525

<210> SEQ ID NO 8
<211> LENGTH: 52
<212> TYPE: PRT
<213> ORGANISM: artificial
<220> FEATURE:
<223> OTHER INFORMATION: frgament of fibrinogen beta 15-66
```

```
<400> SEQUENCE: 8

Gly His Arg Pro Leu Asp Lys Lys Arg Glu Glu Ala Pro Ser Leu Arg
1               5                   10                  15

Pro Ala Pro Pro Ile Ser Gly Gly Tyr Arg Ala Arg Pro Ala
            20                  25                  30

Lys Ala Ala Ala Thr Gln Lys Lys Val Glu Arg Lys Ala Pro Asp Ala
        35                  40                  45

Gly Gly Cys Gly
        50

<210> SEQ ID NO 9
<211> LENGTH: 452
<212> TYPE: PRT
<213> ORGANISM: artificial
<220> FEATURE:
<223> OTHER INFORMATION: Tenascin III1-5

<400> SEQUENCE: 9

Glu Val Ser Pro Pro Lys Asp Leu Val Val Thr Glu Val Thr Glu Glu
1               5                   10                  15

Thr Val Asn Leu Ala Trp Asp Asn Glu Met Arg Val Thr Glu Tyr Leu
            20                  25                  30

Val Val Tyr Thr Pro Thr His Glu Gly Gly Leu Glu Met Gln Phe Arg
        35                  40                  45

Val Pro Gly Asp Gln Thr Ser Thr Ile Ile Gln Glu Leu Glu Pro Gly
    50                  55                  60

Val Glu Tyr Phe Ile Arg Val Phe Ala Ile Leu Glu Asn Lys Lys Ser
65                  70                  75                  80

Ile Pro Val Ser Ala Arg Val Ala Thr Tyr Leu Pro Ala Pro Glu Gly
                85                  90                  95

Leu Lys Phe Lys Ser Ile Lys Glu Thr Ser Val Glu Val Glu Trp Asp
            100                 105                 110

Pro Leu Asp Ile Ala Phe Glu Thr Trp Glu Ile Ile Phe Arg Asn Met
        115                 120                 125

Asn Lys Glu Asp Glu Gly Glu Ile Thr Lys Ser Leu Arg Arg Pro Glu
    130                 135                 140

Thr Ser Tyr Arg Gln Thr Gly Leu Ala Pro Gly Gln Glu Tyr Glu Ile
145                 150                 155                 160

Ser Leu His Ile Val Lys Asn Asn Thr Arg Gly Pro Gly Leu Lys Arg
                165                 170                 175

Val Thr Thr Thr Arg Leu Asp Ala Pro Ser Gln Ile Glu Val Lys Asp
            180                 185                 190

Val Thr Asp Thr Thr Ala Leu Ile Thr Trp Phe Lys Pro Leu Ala Glu
        195                 200                 205

Ile Asp Gly Ile Glu Leu Thr Tyr Gly Ile Lys Asp Val Pro Gly Asp
    210                 215                 220

Arg Thr Thr Ile Asp Leu Thr Glu Asp Glu Asn Gln Tyr Ser Ile Gly
225                 230                 235                 240

Asn Leu Lys Pro Asp Thr Glu Tyr Glu Val Ser Leu Ile Ser Arg Arg
                245                 250                 255

Gly Asp Met Ser Ser Asn Pro Ala Lys Glu Thr Phe Thr Thr Gly Leu
            260                 265                 270

Asp Ala Pro Arg Asn Leu Arg Arg Val Ser Gln Thr Asp Asn Ser Ile
        275                 280                 285

Thr Leu Glu Trp Arg Asn Gly Lys Ala Ala Ile Asp Ser Tyr Arg Ile
```

```
                    290                 295                 300
Lys Tyr Ala Pro Ile Ser Gly Gly Asp His Ala Glu Val Asp Val Pro
305                 310                 315                 320

Lys Ser Gln Gln Ala Thr Thr Lys Thr Thr Leu Thr Gly Leu Arg Pro
                325                 330                 335

Gly Thr Glu Tyr Gly Ile Gly Val Ser Ala Val Lys Glu Asp Lys Glu
                340                 345                 350

Ser Asn Pro Ala Thr Ile Asn Ala Ala Thr Glu Leu Asp Thr Pro Lys
            355                 360                 365

Asp Leu Gln Val Ser Glu Thr Ala Glu Thr Ser Leu Thr Leu Leu Trp
        370                 375                 380

Lys Thr Pro Leu Ala Lys Phe Asp Arg Tyr Arg Leu Asn Tyr Ser Leu
385                 390                 395                 400

Pro Thr Gly Gln Trp Val Gly Val Gln Leu Pro Arg Asn Thr Thr Ser
                405                 410                 415

Tyr Val Leu Arg Gly Leu Glu Pro Gly Gln Glu Tyr Asn Val Leu Leu
                420                 425                 430

Thr Ala Glu Lys Gly Arg His Lys Ser Lys Pro Ala Arg Val Lys Ala
                435                 440                 445

Ser Thr Glu Gln
    450
```

<210> SEQ ID NO 10
<211> LENGTH: 7
<212> TYPE: PRT
<213> ORGANISM: artificial
<220> FEATURE:
<223> OTHER INFORMATION: residues 1-8 of alpha2-plasmin inhibitor

<400> SEQUENCE: 10

```
Asn Gln Glu Gln Val Ser Pro
1               5
```

<210> SEQ ID NO 11
<211> LENGTH: 5
<212> TYPE: PRT
<213> ORGANISM: artificial
<220> FEATURE:
<223> OTHER INFORMATION: FN III9 synergy site

<400> SEQUENCE: 11

```
Pro His Ser Arg Asn
1               5
```

<210> SEQ ID NO 12
<211> LENGTH: 7
<212> TYPE: PRT
<213> ORGANISM: artificial
<220> FEATURE:
<223> OTHER INFORMATION: domain of TNCIII3

<400> SEQUENCE: 12

```
Val Thr Asp Thr Thr Ala Leu
1               5
```

<210> SEQ ID NO 13
<211> LENGTH: 8
<212> TYPE: PRT
<213> ORGANISM: artificial
<220> FEATURE:
<223> OTHER INFORMATION: fibronection type III domain fragment

```
<400> SEQUENCE: 13

Ala Glu Ile Asp Gly Ile Glu Leu
1               5
```

EXTRACELLULAR MATRIX HEPARIN-BINDING DOMAINS

CROSS REFERENCE TO RELATED APPLICATIONS

This application claims priority to U.S. Ser. No. 61/667,634 filed Jul. 3, 2012 which is hereby incorporated by reference herein.

TECHNICAL FIELD OF THE INVENTION

The technical field relates to extracellular matrix heparin-binding domains, and applications and uses thereof including recombinant fusion molecules and blocking antibodies.

BACKGROUND

The extracellular matrices (ECMs) of the body provide organization to its cells to create tissues and organs. An ECM has many cell signaling factors, including factors that are part of the ECM, for example cell adhesion ligands, and factors that are releasable, such as cytokines. ECMs and cell-ECM interactions are complex and are the subject of ongoing research and discoveries.

SUMMARY

Presented herein are discoveries that the heparin binding domains of both tenascin (TNC, specifically the domain therein referred to as TNC III5) and fibrinogen (FG, specifically the domain thereof referred to as Fg β15-66) are able to specifically bind very strongly to a number of cytokines, which may play an important role in providing signals to a variety of cells to adhere, proliferate, migrate, and otherwise function. Both the TNC III5 and Fg β15-66 domain can be engineered to provide pharmacologically beneficial binding of cytokines with various medical uses, for instance, in promoting tissue repair. These domains can be used to deliver various therapeutic agents as medicaments, for instance by direct injection into tissue or the bloodstream, or as part of biomaterial matrices that interact with cells or release drugs.

DETAILED DESCRIPTION OF THE PREFERRED EMBODIMENTS

Figure 1:
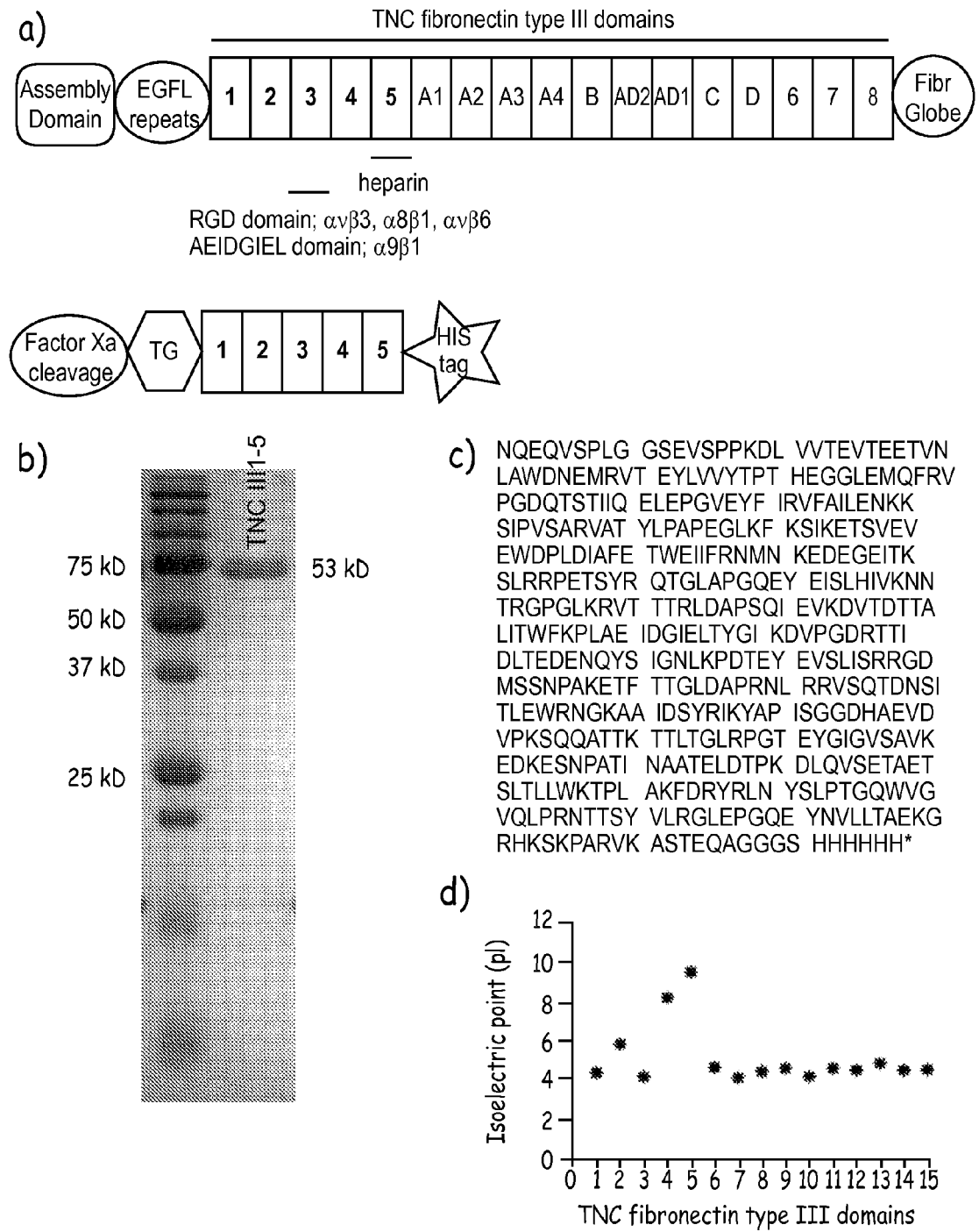
FIG. 1 is a montage having panels a to d, showing a structure and experimental results. Panel a) Schematic of full length human tenascin and engineered TNC III1-5, Panel b) SDS page gel of purified TNC III1-5, Panel c) amino acid sequence of TNC III1-5 (SEQ ID NO:1) with a GGS linker to residues 1-8 of alpha2-plasmin inhibitor (NQEQVSPL) SEQ ID NO:10)) on its N-terminus; at the C-terminus of the construct is a short linker sequence, GGGS, followed by a 6×His tag; Panel d) Isoelectric point (pI) of fibronectin type III domains of tenascin.

Heparin binding domains of both tenascin (TNC, specifically the domain therein referred to as TNC III5) and fibrinogen (FG, specifically the domain thereof referred to as Fg β15-66) have been discovered to specifically bind very strongly to a number of cytokines. The domains may be used to deliver therapeutic agents as well as create biomaterials that bind and/or release cytokines and other biochemicals involved in cellular and physiological functions.

Extracellular Matrix (ECM) Molecules

Extracellular matrix (ECM) molecules are the backbone of the cellular organization inside the body. ECM biomolecules are grouped together because of their role in the ECM. They are, however, very diverse, generally being from different protein families and generally having very different structures, cells of origin, sequences, and patterns of expression, as well as having remarkably distinct modes of action and function. They frequently contain many integrin binding domains for cell attachment, migration, and differentiation, while many cytokines are physiologically stored in this natural scaffold (Schonherr and Hausser, 2000). Cells receive numerous signals from their immediate microenvironment, the ECM (Kleinman, Philp, et al., 2003). Within a biomechanical context provided by this elastic milieu (Discher, Mooney, et al., 2009), cells adhere by receptor-mediated interactions with ECM components, such as FN, laminin, etc, mediated by specialized adhesion receptors such as integrins and others (Berrier and Yamada, 2007). These receptors transmit stress from the ECM, through the membrane, to the cytoskeleton within the cell in a dynamic and concerted manner (Hinz, 2009). The adhesion receptors do much more than transmit stress, however; in particular within clusters of adhesion receptors in the membrane, biochemical signal transduction takes place through kinase activation and other mechanisms (Berrier and Yamada, 2007; Hinz, 2009). In addition to adhesion proteins, the ECM also sequesters and presents a number of morphoregulatory molecules including cytokines, which control processes of cell division, and/or migration, and/or differentiation, and/or multicellular morphogenesis (Discher, Mooney, et al., 2009; Schultz and Wysocki, 2009). For example, key cytokines involved in tissue morphogenesis include vascular endothelial growth factors (VEGFs), platelet derived growth factors (PDGFs), fibroblast growth factor (FGFs), insulin-like growth factors (IGFs), bone morphogenetic proteins (BMPs), transforming growth factors beta (TGF-β), and neurotrophins. The cytokines bind ECM components such as heparan sulfate proteoglycans (Lindahl and Li, 2009), and reside there until released by enzymatic processes or dissociation. These factors, when released and sometimes also when matrix-bound (Makarenkova, Hoffman, et al., 2009), bind to cell-surface receptors and trigger signaling, principally through kinase activation. Thus, the ECM serves as a reservoir of signaling molecules, both adhesion molecules and cytokines, that instruct cell decision processes. Angiogenesis, multicellular morphogenesis, and stem cell differentiation are cellular processes that are tightly controlled by the ECM and cytokines, and especially by their cooperative signaling.

Herein it is reported that the HBD of two ECM proteins, tenascin C (TNC) and fibrinogen, have the ability to bind many cytokines of different protein families, which leads to many possible ECM fusion fragments, e.g., by combining specific integrin and cytokine binding domains, depending on the application. Elsewhere, it was demonstrated that another ECM protein, fibronectin (FN), binds a wide variety of specific cytokines at the location of its heparin binding domain (HBD) (Martino and Hubbell, 2010), while a multifunctional recombinant FN fragment containing a mayor integrin binding domain in combination with this HBD resulted in potent synergistic signaling and morphogenesis between integrins and growth factor receptors (Martino, Tortelli, et al., 2011).

Tenascin C

Tenascin C (TNC) is a large multifunctional extracellular matrix (ECM) glycoprotein that is present during development and re-expressed in adult life in the case of tissue remodeling, such as wound healing (Trebaul, Chan, et al., 2007), cancer (Orend, 2005), and inflammation (Udalova, Ruhmann, et al., 2011). During development, TNC plays a highly restricted and dynamic role in the patterning of the neural and vascular networks and the skeleton. It has shown to affect cell adhesion, proliferation, and migration via direct interaction with cells or indirectly through binding to other ECM molecules, such as fibronectin (Jones and Jones, 2000).

In a healthy adult organism, TNC is produced in a tightly controlled, rapid, and transient manner and contained to specific locations where tissue repair, such as wound healing and nerve regeneration (Joester and Faissner, 2001), is necessary and infection needs to be resolved (Udalova, Ruhmann, et al., 2011). However, in the case of uncontrolled TNC production, this molecule becomes pathological resulting in abnormal tissue growth, such as cancer, restenosis after percutaneous coronary angioplasty (Imanaka-Yoshida, Matsuura, et al., 2001) and stent implantation (Iso 2005), fibrotic diseases, chronic wounds, cardiovascular diseases (Golledge, Clancy, et al., 2011), and autoimmune diseases (Udalova, Ruhmann, et al., 2011). Recently, TNC has been linked to cardiac and arterial injury, tumor angiogenesis and metastasis (O'Connell, Sugimoto, et al., 2011; Oskarsson, Acharyya, et al., 2011), as well as in modulating stem cell behavior (Midwood, Hussenet, et al., 2011). In the case of cancer metastasis, it has been shown that cancer cells, responsible for metastasis, produce TNC, with inhibition of this TNC production resulting in reduced metastasis (Oskarsson, Acharyya, et al., 2011). Accordingly, the HBD domains and the cytokine binding activity of TNC reported herein are useful for making various therapeutic materials and treatments.

Fibrinogen

Fibrinogen is a soluble plasma glycoprotein that is synthesized by the liver and the precursor protein during blood coagulation. The proteolytic enzyme thrombin, coagulation factor II, will polymerize fibrinogen into fibrin during coagulation by cleaving fibrinopeptides from its central domain, preventing physicochemical self-assembly or polymerization of the molecule (Weisel, 2007). Fibrin is sequentially chemically cross-linked by factor XIIIa forming the primary structural protein of a viscoelastic blood clot (Mosesson, 2005), and functioning as a specialized provisional protein network that is formed principally in spontaneous tissue repair.

The stability of fibrin depends on its interplay with molecular/cellular components of the hemostatic system (Hantgan, Francis, et al., 1994). In addition to cross-linking fibrin to itself, factor XIIIa cross-links other adhesive proteins into the blood clot. Fibrin can bind several cell-adhesion receptors such as integrins and notably promotes the adhesion of platelet and leukocytes such as monocytes and neutrophils (Ugarova and Yakubenko, 2001; Flick, Du, et al., 2004).

Fibrin gels were one of the first biomaterials used to prevent bleeding and promote wound healing (Janmey, Winer, et al., 2009). Fibrin is available from autologous sources and from cryoprecipitated pooled human blood plasma. Today, fibrin is one of the most used hydrogels in the clinic. The complex fibril structure and cross-linked character of fibrin matrix can be controlled by the details of its formation (Lorand and Graham, 2003; Standeven, Carter, et al., 2007; Weisel, 2004). Importantly, in contrast to fibrillar collagen matrices where cell migration occurs both through mechanisms that are dependent and independent of proteolytic degradation, cell migration in fibrin is almost exclusively dependent upon cell-associated proteolytic activity (essentially from plasmin and matrix metalloproteinases (Mosesson, 2005)). One of the main advantages of fibrin is that several proteins are naturally incorporated into fibrin matrix during the coagulation such as fibronectin and alpha-2-plasmin inhibitor, by covalent cross-linking via the transglutaminase factor XIIIa (Mosesson, 2005). Therefore, this natural reaction can be exploited to functionalize fibrin with multiple cell-signaling molecules (Schense and Hubbell, 1999; Patterson, Martino, et al., 2010). In addition, fibrinogen is known to possess specific interactions with fibroblast growth factor (FGF)-2, VEGF-A165 and insulin-like growth factor binding protein (IGFBP)-3 (Sahni, Khorana, et al., 2006; Peng, Sahni, et al., 2004; Werner and Grose, 2003; Sahni, Odrljin, et al., 1998). The reports presented herein provide demonstration of specific binding domains for some of these factors and identify further factors for binding to the same.

Fibronectin

Fibronectin (FN) is a key adhesion protein found in the blood and in the interstitial ECM, widely expressed by multiple cell types, and critically important in many ECM-dependent processes in vertebrate (Krammer, Craig, et al., 2002) by playing important roles in cell adhesion, migration, growth and differentiation (Mao and Schwarzbauer, 2005; Pankov and Yamada, 2002). FN can be subdivided into two forms, soluble plasma FN (abundant soluble constituent of plasma [300 μg/mL]) and less-soluble cellular FN. Plasma FN is secreted by hepatocytes and enriched in blood whereas cellular FN is secreted by fibroblasts and many other cell types and is incorporated into a fibrillar matrix at the cell surface. Cellular FN consists of a much larger and more heterogeneous group of FN isoforms that result from cell-type specific splicing patterns producing FNs with different cell-adhesive, ligand-binding, and solubility properties that provide a mechanism for cells to precisely alter the composition of the ECM in a developmental and tissue-specific manner.

Elsewhere, inventors of the present application discovered that FN acts as a promiscuous growth factor (GF) binding protein (Martino and Hubbell, 2010). Through its second heparin-binding domain (FN III12-14), fibronectin binds GFs from the platelet-derived growth factor (PDGF)/VEGF and FGF families and some GFs from the transforming growth factor-β (TGF-β) and neurotrophin families. Similarly, vitronectin has been shown to bind insulin-like growth factor (IGF)-II, IBFBP-3, IGFBP-5, TGF-β1, TGF-β2, epidermal growth factor (EGF), VEGF-A165 and FGF-2, probably through its heparin-binding domain (Upton, Webb, et al., 1999; Kricker, Towne, et al., 2003; Schoppet, Chavakis, et al., 2002).

Tenascin C Structure

Human tenascin C (Uniprot: P24821) is a disulfide-bonded hexabranchion containing 4 major domains: First, an assembly domain at the N-terminal forms a coiled coil structure and interchain disulfide bonds that mediates the hexamer formation. Second, a series of 14.5 epidermal growth factor-like (EGFL) repeats, which are between 30 and 50 amino acids long and each contain six cysteines, have shown to obtain anti-adhesive properties. Third, a series of 15 fibronectin type III repeats, which are approximately 90 amino acids long and form two sheets of antiparallel β-strands, contain several integrin binding regions (Jones and Jones, 2000). Fourth, a fibrinogen like globular domain is located at the C terminal (Udalova, Ruhmann, et al., 2011; Midwood, Hussenet, et al., 2011).

The fibronectin type III domain region of tenascin has shown a large variability due to alternative splicing depending on the TNC source (Jones and Jones, 2000). The numbers (x-y) of fibronectin type III domains of TNC will be defined in this report as TNC IIIx-y. Domain TNC III3 consists of six extended loops separating seven β strands (A-G) (Leahy, Hendrickson, et al., 1992; Peng, Zhuang, et al., 2009; Yokosaki, Matsuura, et al., 1998) and multiple integrin binding domains (for example: $\alpha_\nu\beta_3$, $\alpha_2\beta_1$, $\alpha_\nu\beta_6$, $\alpha_9\beta_1$, $\alpha_\xi\beta_1$, $\alpha_8\beta_1$) for a large variety of cell types (for example: smooth muscle cells, endothelial cells, neurons, astrocytes, glioma) (Jones and Jones, 2000). Domain TNC III5 has been demonstrated to bind heparin (Weber, Zimmermann, et al., 1995). The F-G loop contains the RGD peptide, which has shown to bind integrins $\alpha_\nu\beta_3$, $\alpha_8\beta_1$, and $\alpha_\nu\beta_6$, the recognition sequence AEIDGIEL (SEQ ID NO:13, which includes portions of the B-C loop and the adjacent C strand, has shown to bind $\alpha_9\beta_1$. Additionally, it has been suggested that another domain, VTDTTAL (SEQ ID NO:12) in TNC III3, may play a role in $\alpha_9\beta_1$ binding, as the D787A mutation inhibited adhesion probably by altering the conformation of the critical AEIDGIEL (SEQ ID NO:13) region in the B-C loop on the opposite face of TN III3 (Yokosaki, Matsuura, et al., 1998).

Fibrinogen

Fibrinogen is a dimeric molecule consisting of three pairs of disulfide-bonded polypeptide chains: Aα, Bβ, and γ (Weisel, Stauffacher, et al., 1985). Each set of the three polypeptide chains of human fibrinogen contains 1482 amino acid residues with defined domains for disulfide crosslinks, carbohydrate attachment, proteolytic cleavage, enzymatic crosslinking, fibrin assembly, and platelet recognition (Hantgan, Francis, et al., 1994). The computed molecular weight of fibrinogen is 340 Da. The amino terminals form the E domain and the carboxy terminals form the D domains. The heparin-binding domain of fibrinogen (Fg) is located in the β strand of the E domain between aa15-66 (Fg β15-66) (Odrljin, Shainoff, et al., 1996).

Fibronectin

Fibronectin (FN) is widely expressed by multiple cell types and is critically important in many ECM-dependent processes in vertebrate (Krammer, Craig, et al., 2002), by playing important roles in cell adhesion, migration, growth and differentiation (Mao and Schwarzbauer, 2005; Pankov and Yamada, 2002). FN is a dimeric glycoprotein composed of two nearly identical 230-270 kDa subunits linked covalently near their C-termini by a pair of disulfide bonds. Each subunit consists of three types of repeating modules, type I, II and III. These modules comprise functional domains that mediate interactions with other ECM components, with cell surface receptors, and with FN itself. FN contains 12 type I repeats, 2 type II repeats and 15-18 type III repeats. The numbers (x-y) of fibronectin type III domains of fibronectin (FN) will be defined in this report as FN IIIx-y.

FN can be subdivided into two forms, soluble plasma FN (abundant soluble constituent of plasma [300 μg/mL]) and less-soluble cellular FN. Plasma FN is secreted by hepatocytes and enriched in blood whereas cellular FN is secreted by fibroblasts and many other cell types and is incorporated into a fibrillar matrix at the cell surface. Cellular FN consists of a much larger and more heterogeneous group of FN isoforms that result from cell-type specific splicing patterns producing FNs with different cell-adhesive, ligand-binding, and solubility properties that provide a mechanism for cells to precisely alter the composition of the ECM in a developmental and tissue-specific manner.

FN is a ligand for a dozen members of the integrin receptor family. The most well studied recognition sequence, RGD, is located in the $10^{th}$ type III repeat (FN III10). The recognition of this simple tripeptide sequence is complex and depends on flanking residues, its three dimensional presentation and individual features of the integrin-binding pockets. For example, a second site in the $9^{th}$ type III repeat (FN III9), the "synergy site" PHSRN (SEQ ID NO:11) (Mardon and Grant, 1994), promotes specific $\alpha_5\beta_1$ integrin binding to FN, via interactions with the $\alpha_5$ subunit (Mould, Askari, et al., 1997), whereas $\alpha_\nu\beta_3$ integrin binding to RGD is independent of this synergy site (Danen, Aota, et al., 1995). Importantly, instability issues related to FN III9, and even FN III9-10, led to the finding of a mutation (Leu1408 with Pro) that was able to increase the conformational stability of the FN III9 by 2-3-fold (van der Walle, Altroff, et al., 2002). The fragment FN III9 containing this mutation is defined herein in this report as FN III9*.

Integrin $\alpha_5\beta_1$ is the initial receptor mediating assembly of FN in fibrillar matrix formation. The integrin interacts with the RGD and the synergy sequence in adjacent module. Integrins link FN to the actin cytoskeleton through interactions between their cytoplasmic domains, cytoskeletal-associated proteins, intracellular adapter and signalling proteins. Initially, complexes, containing an $\alpha_5\beta_1$ integrin, focal adhesion kinase, and tensin, form at sites of fibrillar adhesion. These complexes then dissociate into both focal adhesions and fibrillar adhesions. Focal adhesions provide firm cell attachment to two dimensional substrates in a synergy-site independent manner and contain $\alpha_\nu\beta_3$ integrin, whereas fibrillar adhesions are enriched in integrin $\alpha_5\beta_1$. Fibrillar adhesions are generated by movement of ligated FN and $\alpha_5\beta_1$ integrin from the ends of stationary focal adhesions toward the cell centre along actin stress fibres.

Tissue Repair Processes, Cancer Treatments

After damage, tissue repair or regeneration is the result of a spatio-temporal coordination of cell fate processes that are controlled by a multitude of cell-signaling events coming from the extracellular microenvironment and recruited cells at the site of injury (Gurtner, Werner, et al., 2008). To site few, tissue healing processes such as angiogenesis (Herbert and Stainier, 2011), stem cells homing (Karp and Leng Teo, 2009), or inflammation (Eming, Hammerschmidt, et al., 2009) are all tightly coordinated and controlled by a cascade of cell-signaling events. Angiogenesis, the formation of new blood vessels, is crucial to provide oxygen and nutrients to the regenerating tissue. Various approaches have been made with a goal of providing amenable and tissue-specific matrices to control cell processes, such as adhesion, migration, proliferation, differentiation (Lutolf and Hubbell, 2005; Atala, 2008; Huebsch and Mooney, 2009). A goal is to provide matrices to contain signals that directly act on tissue-damaged cells, attract regeneration-competent cells, block regeneration-suppressing signals, and guide cell fate. Powerful molecules to control these processes are secreted cell-signaling molecules such as morphogens (Affolter and Basler, 2007), cytokines (Vilcek and Feldmann, 2004), and growth factors (Cross and Dexter, 1991).

Many processes in cancer progression correspond to processes in tissue repair (Oviedo and Beane, 2009), in that many of the same cytokines are involved in tissue morphogenesis and tissue repair also play roles in cancer stem cell function and in cancer metastasis. A tumor could be viewed, at least in part, as an over-healing wound, or tissue repair in the absence of control (Schafer and Werner, 2008). Cytokines influence cell growth and thus can contribute to developing effective therapies in regenerative medicine and cancer.

For example, TGFβ promotes immune suppression in the tumor environment, inhibiting the anti-tumor effector functions of many immune cells (Wrzesinski, Wan, et al., 2007). TGFβ plays an important role in epithelial-mesenchymal transition (EMT), which induces the transformation of epithelial cells to mesenchymal like cells with enhanced motility, invasion, and metastasis (Bierie and Moses, 2010). Additionally, TGFβ promotes differentiation of myofibroblasts, which remodel the collagen stroma within the tumor into aligned collagen fibers that promotes stromal stiffness, invasion and metastasis (Untergasser, Gander, et al., 2005). FGFs and their receptors function in an oncogenic manner during cancer, resulting in proliferation, survival, migration and differentiation, while promoting EMT, invasion and angiogenesis (Wesche, Haglund, et al., 2011). Tumor-associated angiogenesis supports tumor growth and is promoted by the VEGF family. In the initial stages of wound healing and tumor growth, VEGF-A induces vascular permeability. However, in wound healing, this leakiness is only transient, while in the case of cancer it might persist (Schafer and Werner, 2008). Enhanced expression of VEGF-C in tumors promotes lymphangiogenesis and is correlated with lymph node metastases (Lohela, Bry, et al., 2009). Direct autocrine signaling of VEGF-C expressing tumor cells promotes expression of matrix metalloproteinases (MMPs), matrix degradation, and lymphatic homing (Issa, Le, et al., 2009). Platelet-derived growth factor-D (PDGF-D) can regulate many cellular processes, including cell proliferation, apoptosis, transformation, migration, invasion, angiogenesis and metastasis (Wang, Ahmad, et al., 2010), while brain-derived neurotrophic factor (BDNF), which has recently emerged as a novel angiogenic factor, promotes tumorigenesis via induction of neovascularization (Lam, Yang, et al., 2011). BDNF was also upregulated in certain tumors, promoting proliferation (Kramer, Stover, et al., 2010) and metastasis/invasive properties of individual cancer cells.

Heparin Binding Peptide Activities

Tenascin C (TNC) is a large multifunctional protein. The unexpected and surprising discovery is reported herein that an N-terminal domain, namely the domain TNC III5, which binds heparin, binds very strongly to a large number of cytokines. TNC has not been previously described to bind cytokines. The discovered affinity between TNC III1-5 and smaller domains from within this domain and a number of cytokines leads to a number of embodiments, described herein.

Fibrinogen, which is converted into fibrin during the coagulation process to form the fibrin clot, has been reported to act as GF reservoir during tissue healing processes (Upton, Webb, et al., 1999; Kricker, Towne, et al., 2003; Mosesson, 2005). So far, fibrin(ogen) has been shown to bind with high affinity to FGF-2 (Sahni, Khorana, et al., 2006; Peng, Sahni, et al., 2004; Sahni, Odrljin, et al., 1998; Upton, Webb, et al., 1999), VEGF-A165 (Kricker, Towne, et al., 2003), and IGFBP-3 (Werner and Grose, 2003). As reported herein, it has been discovered that fibrin(ogen) is able to bind cytokines very promiscuously through its heparin-binding domain with high affinity. Sixteen new binding interactions were identified with cytokines from diverse families and two new interactions with cytokine-binding proteins, namely VEGF-A165, VEGF-B, PlGF-2, PlGF-3, PDGF-AB, PDGF-BB, FGF-2, FGF-5, FGF-7, FGF-10, TGF-β1, TGF-β2, BMP-2, BMP-2/7, NT-3, BDNF, IGFBP-3 and IGFBP-5.

Figure 2:
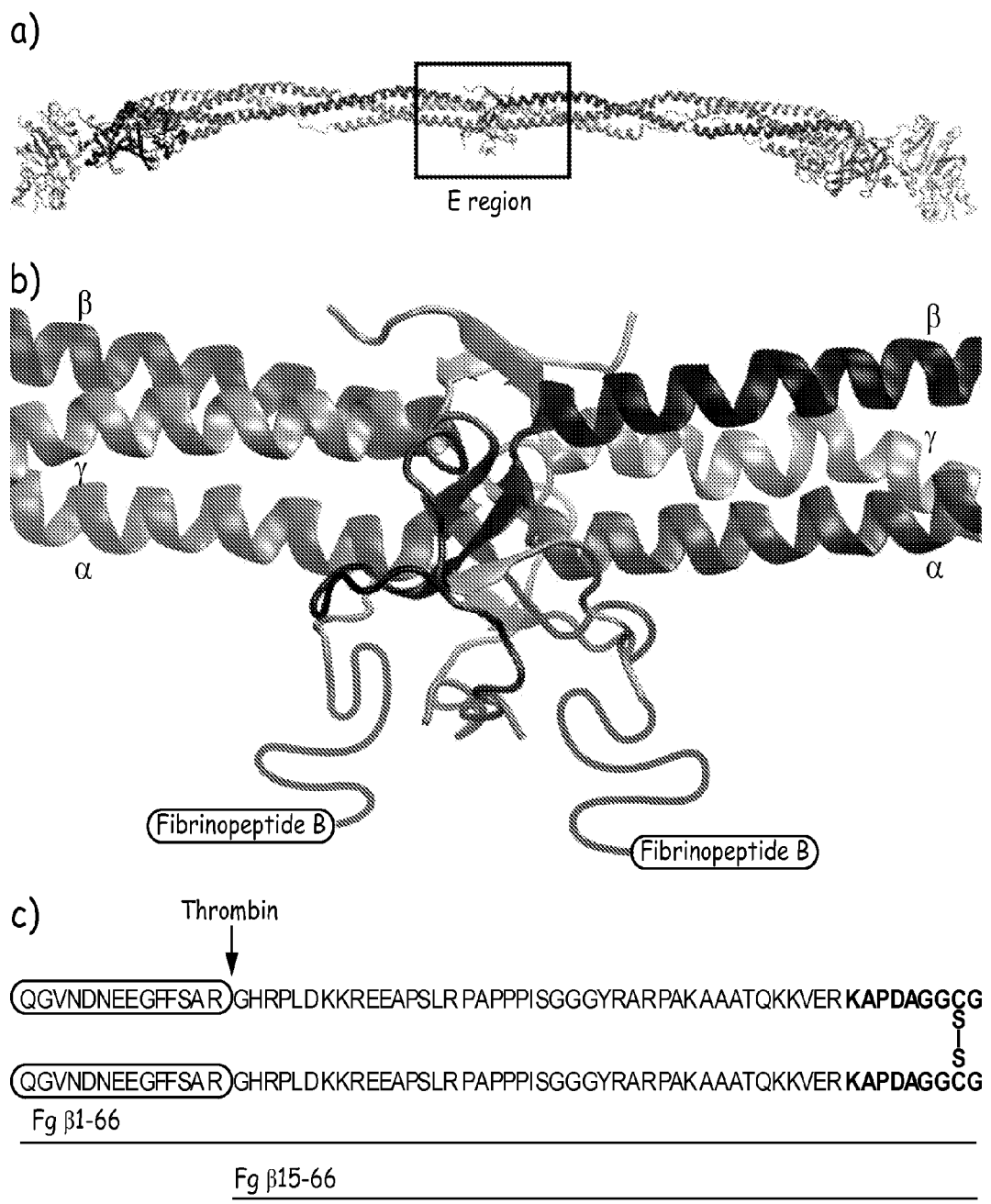
FIG. 2 is three-panel an illustration of a heparin-binding domain of fibrin(ogen), with a ribbon diagram representation of fibrinogen and its central region E. Panel a) Representation of the fibrinogen molecule. Panel b) Focus on the E region. The coiled-coil domains are colored in gray; the N-terminus portions of the Bβ chain indicated (Fg β59-66), while the N-terminus part of the Bβ chain missing in the crystal structure (Ehrbar, Rizzi, et al., 2007) are in contrast (Fg β1-58); the fibrinopeptides B are in highlighted in contrast (Fg β1-14). Panel c) Amino acid sequence of the heparin-binding domain Fg β15-66 (SEQ ID NO: 8) (Ehrbar, Rizzi, et al., 2007). The region within Fg β1-66 (SEQ ID NO: 14) with unknown tertiary structure is in contrast, while the known tertiary structure is in lighter contrast. The arrow indicates the thrombin cleavage site to remove fibrinopeptide B.

Example 1 describes the recombinant production of TNCIII1-5, which is a TNC domain. SEQ ID NO:1 provides details of the specific sequence used, with SEQ ID NO:9 showing TNCIII1-5. FIG. 1 provides details on TNCIII1-5. Example 2 describes the recombinant production of Fg β15-66. SEQ ID NO:2 provides details of the specific sequence used. FIG. 2 illustrates the location of Fg β15-66.

Example 3 (see FIG. 3) demonstrates that TNCIII1-5 bound certain cytokines (FGF-2, FGF-4, FGF-6, FGF-7, FGF-17, FGF-18, TGF-β1, TGF-β2, NT-3, BDNF, PLGF-2, PLGF-1, BMP-2, PDGF-AA, PDGF-AB, PDGF-BB, PDGF-DD, VEGF-A165, VEGF-B, VEGF-C, IGF-BP3, IGF-BP5, HGF) but not others tested. Heparin was identified as impairing binding to TNCIII1-5, which implicated a role for a heparin binding domain (HBD). Example 4 (see also FIG. 4) demonstrates that Fg β15-66 bound certain cytokines (VEGF-A165, VEGF-B, PlGF-2, PlGF-3, PDGF-AB, PDGF-BB, FGF-2, FGF-5, FGF-7, FGF-10, TGF-β1, TGF-β2, BMP-2, BMP-2/7, NT-3, BDNF, IGFBP-3 and IGFBP-5) but not others tested. Accordingly, both sites bound FGF-2, FGF-7, FGF-10, TGF-β1, TGF-β2, NT-3, BDNF, PLGF-2 BMP-2, PDGF-AB, PDGF-BB, VEGF-A165, VEGF-B, IGF-BP3, and IGF-BP5 but other cytokines bound only one of the sites and not the other. Examples 3 and 4 clearly show specific binding of the domains to the various cytokines.

Figure 9:
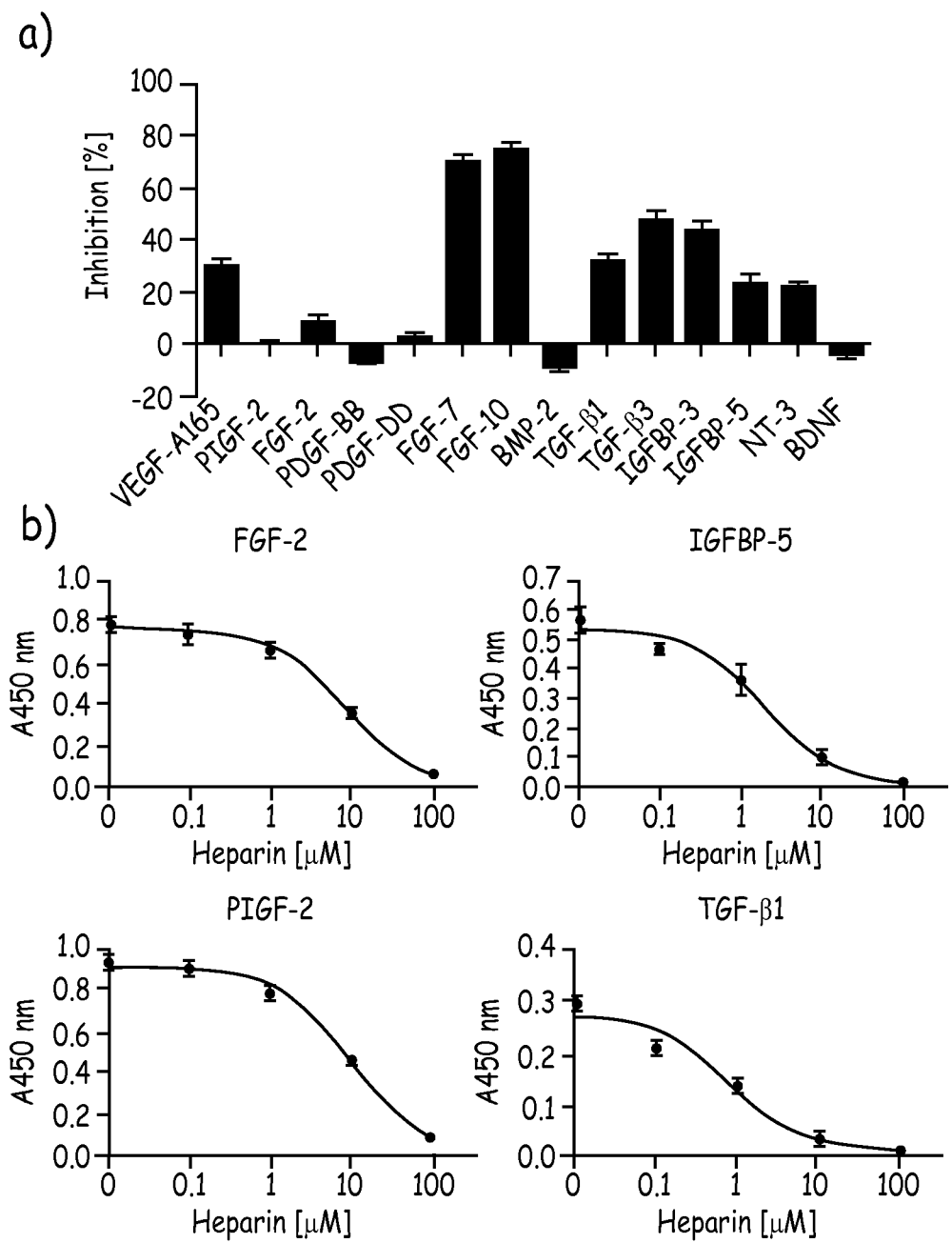
FIG. 9 has two panels of experimental results showing the influence of heparin on cytokine binding to Fg β15-66. Panel a: The graph shows the percent increase of Fg β15-66 binding signal to cytokines when incubated with heparin in excess (20 fold molar excess relative to Fg β15-66). Panel b: The graphs show the binding signal of Fg β15-66 to cytokines when incubated with heparin at increasing concentration (10 to 10,000 fold molar excess relative to Fg β15-66).
Figure 10:
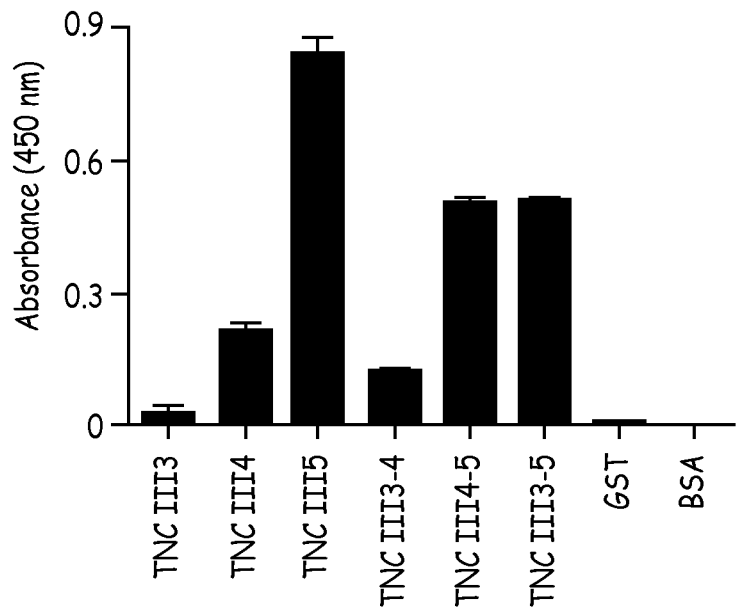
FIG. 10 is a bar graph showing the binding of PDGF-BB to different domains of TNC III1-5.

Example 5 (see FIG. 5) and Example 6 (see FIG. 6) show the actual measured binding affinity, $K_D$, of certain of the cytokines the domains, and shows that the binding can be modeled by Langmuir kinetics. A low $K_D$ indicates avid binding, so there is stronger (increased) binding at a low-value for $K_D$ relative to a higher numerical value for $K_D$. TNC III1-5 binding to cytokines could be blocked with competitive binding of full-length tenascin or heparin (Example 7, FIGS. 7 and 8). The graphs show the binding signal of Fg β15-66 to cytokines when incubated with heparin at increasing concentration (10 to 10,000 fold molar excess relative to Fg β15-66) (Example 8, FIG. 9). Example 9 (FIG. 10) depicts an assay of various regions of TNC, specifically the TNCIII5 domain. These results point to the TNCIII5 subdomain as mediating the cytokines' binding.

Example 10 details embodiments of molecular fusions of heparin binding peptides with moieties that bind to an integrin receptor. One was a fusion of TG-FN III9-10 to TNC III3-5 (see SEQ ID NO:4) TNC III1-5 contains the AEIDGIEL (SEQ ID NO:13) sequence (for $α_9β_1$ integrin). TNC III4-5 demonstrated cytokine-binding. Another molecular fusion involved FN III9-10 to TNC III3-5 (see SEQ ID NO:5). Another molecular fusion involved FN III9-10 to Fg β15-66 (See SEQ ID NO:6). Another molecular fusion involved FN III9-10 to 12-14 and to Fg β15-66 (see SEQ ID NO:7). There is an RGD integrin-binding sequence in the TNC III3 domain, while the addition of FN III9-10 contains the sequence PHSRN (SEQ ID NO:11) (for $α_5β_1$ integrin) and an additional RGD integrin-binding sequence to enhance the overall integrin binding of the TNC-FN fragment. The molecular fusions had a binding activity compared to binding moieties that were not involved in fusions, as demonstrated in Example 11 see also FIG. 11.

Molecular fusions of heparin binding peptides with a transglutaminase substrate (TG) were effectively reacted at the substrate site by a transglutaminase that linked them to complementary substrate. Example 12 (FIG. 12) shows that the activity of the transglutaminase substrate (TG: NQEQVSPL) (SEQ ID NO:10) of the molecular fusion protein TG-TNC III1-5 was confirmed in three different manners and to two different biomaterials: natural fibrinogen and synthetic PEG-lysine. This example includes data showing that a molecular fusion of a TG to TNC III1-5 and a molecular fusion of a TG to FN III9*-10 to fibrinogen and also to gels expressing lysines reactive with the transglutaminase.

Molecular fusions of heparin binding peptides retained their cytokine-binding properties in a biomaterial matrix.

Figure 13:
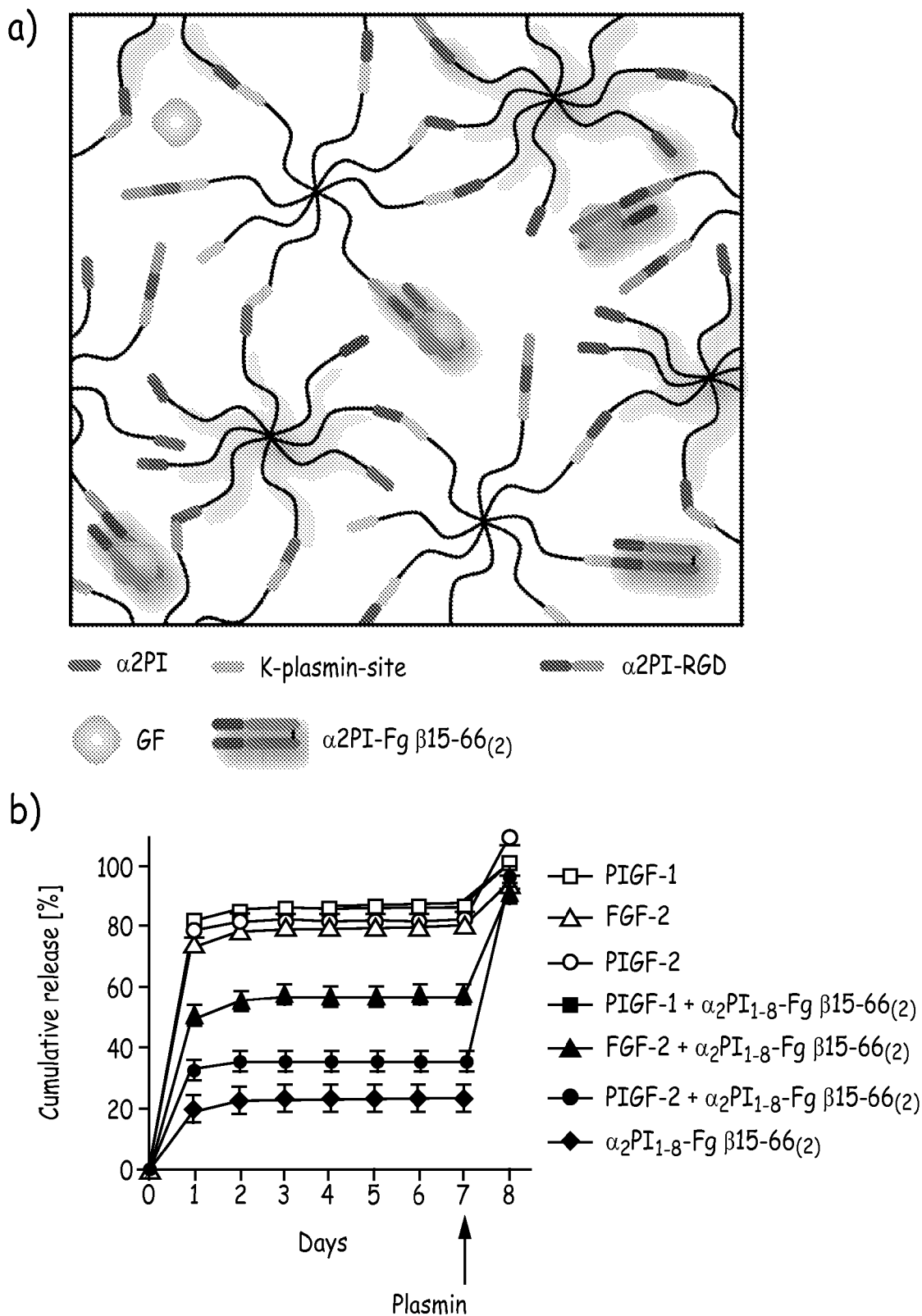
FIG. 13 has two panels, with Panel a being an illustration of a design of TG-PEG gels; and with Panel b being experimental data showing a cumulative release of cytokines and TG-Fg β15-66 over 7 days.

Example 13 (FIG. 13) shows that a molecular fusion of TG and Fg β15-66 retained binding after incorporation into a polyethylene glycol hydrogel.

Figure 16:
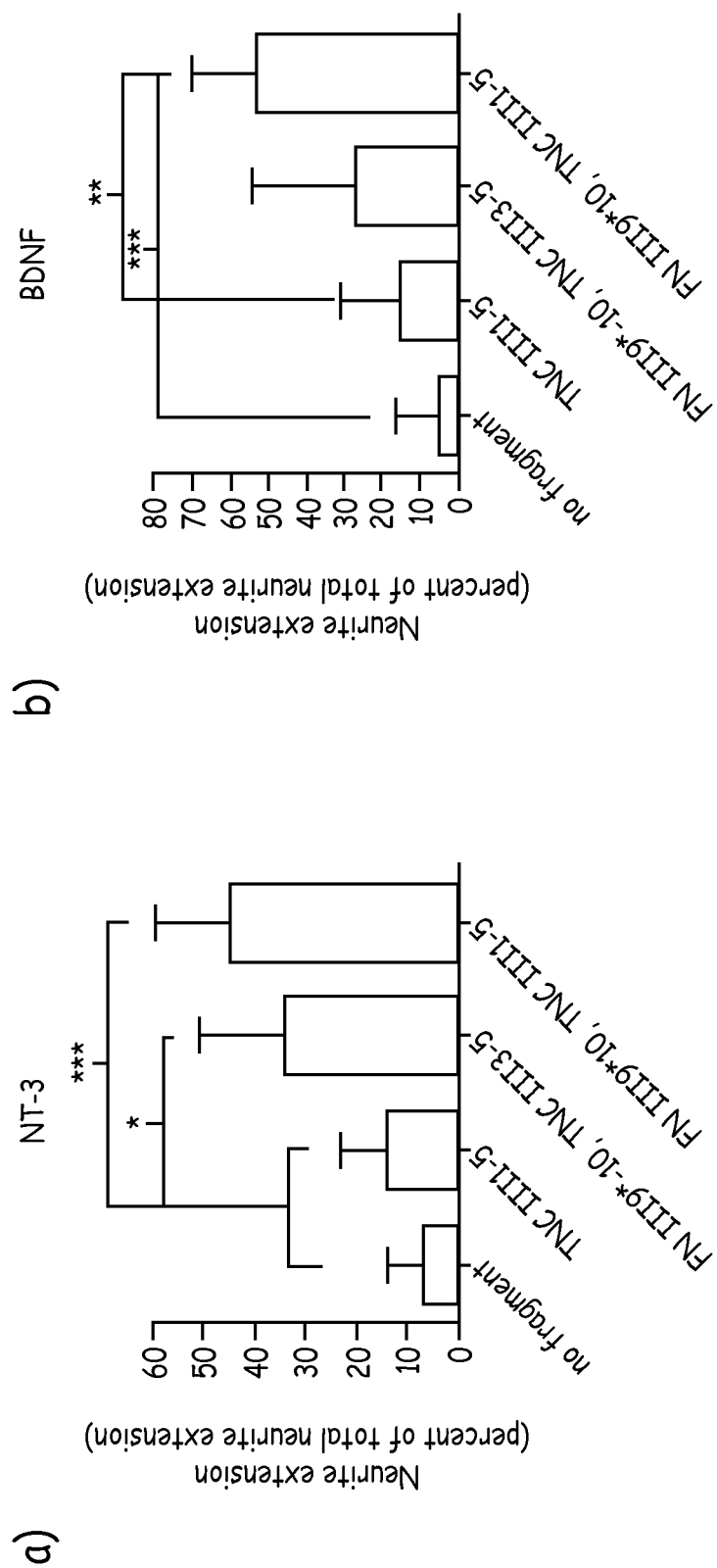
FIG. 16 has two panels of experimental data showing neurite extension on a 2D PEG gel modified with TNC III1-5 and its fusions with FN9*-10; Panel a, with NT-3; Panel b: with BDNF.
Figure 17:
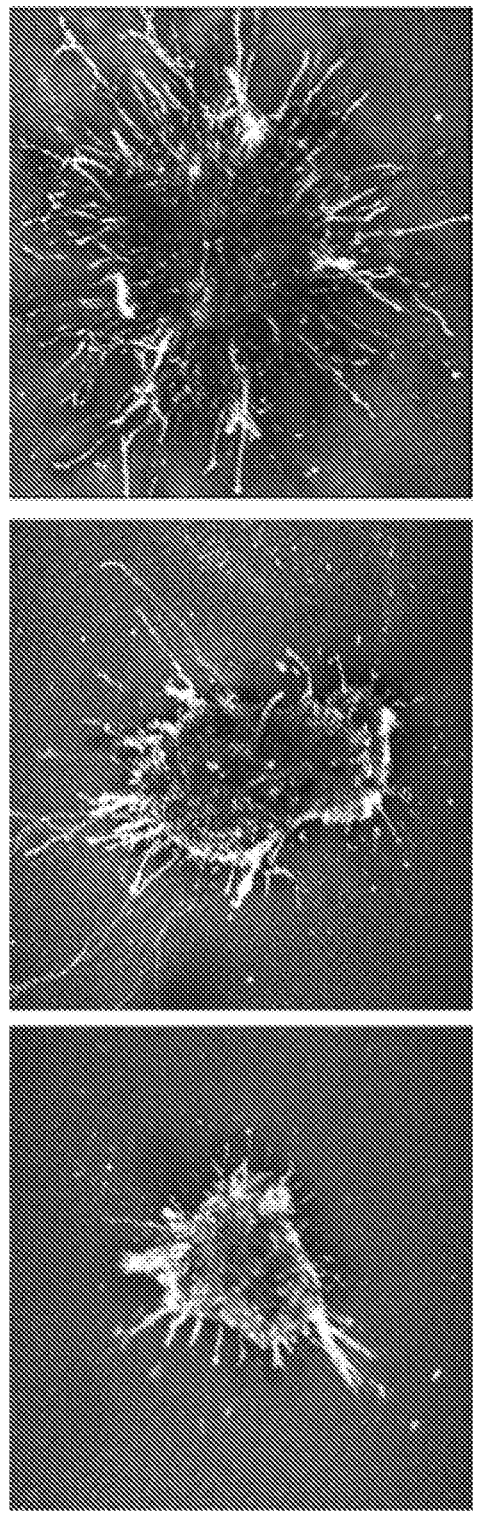
FIG. 17 is a montage of photomicrographs showing cell adhesion, proliferation, migration, and differentiation properties of TNC III1-5 comprising additional domains from fibronectin

Cytokines bound to a heparin binding peptide were demonstrated to retain their activity. Example 14 (FIG. 14) and Example 15 (FIG. 15) showed appropriate proliferation and phosphorylation of two cell types (smooth muscle cells and endothelial cells). Heparin binding peptides were also shown to be active when incorporated onto surfaces or into materials, both with and without a molecular fusion to synergistic cell adhesion domains (Example 16, FIGS. 16 and 17).

Figure 18:
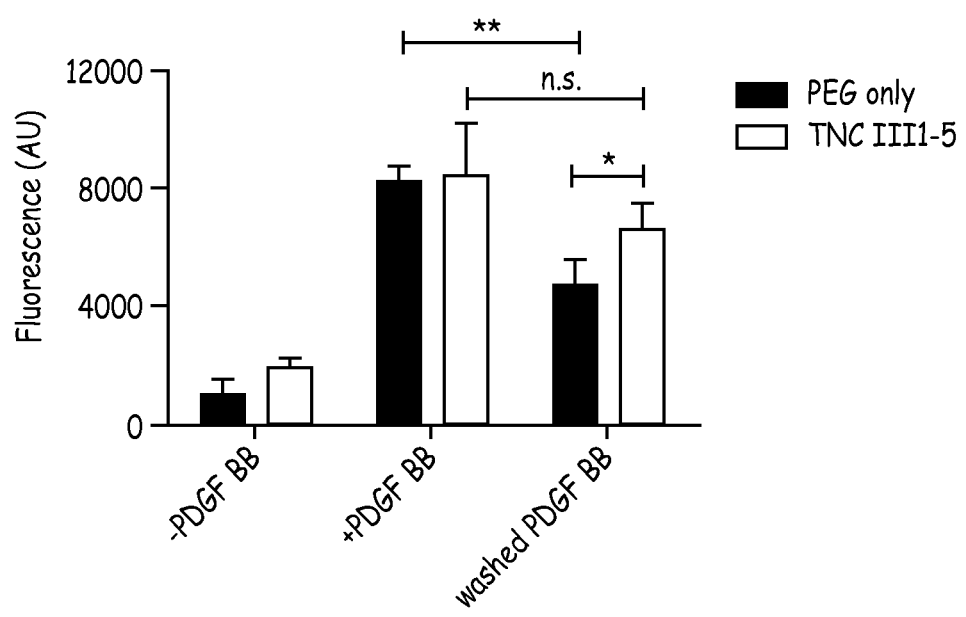
FIG. 18 is a bar graph of experimental data that shows that removal of unbound PDGF-BB from the gels resulted in a significant reduction of proliferation for unmodified gels ($p<0.01$), but not for gels modified with TNC III1-5. Gels, for which unbound PDGF-BB was removed, resulted in significantly increased proliferation when modified with TNC III1-5 ($p<0.05$).
Figure 19:
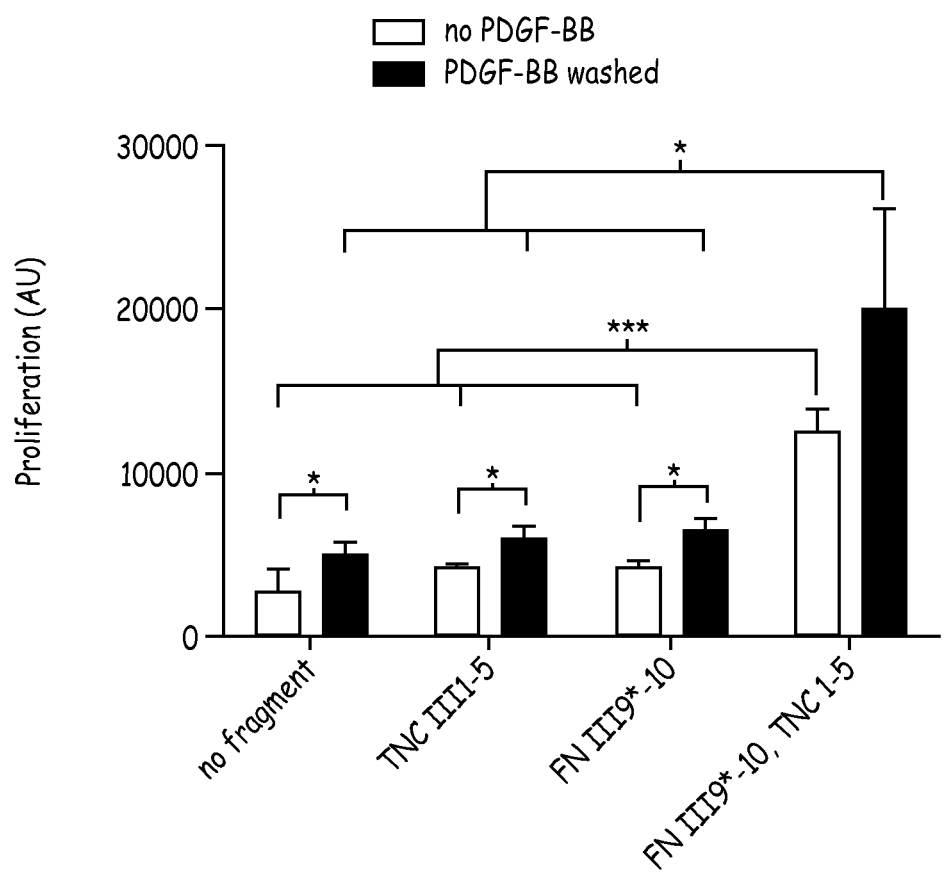
FIG. 19 is a bar graph of experimental data that shows that the addition of the fibronectin integrin binding domain FN III9*-10 to TNC III1-5 significantly enhanced SMC proliferation on top of a PEG gel.

Moreover, heparin-binding peptides effectively withstood challenges by processes known to remove unbound cytokines. In Example 17, FIG. 18, removal of unbound PDGF-BB from the gels resulted in a significant reduction of proliferation for unmodified gels (p<0.01), but not for gels modified with TNC III1-5. Gels, for which unbound PDGF-BB was removed, resulted in significantly increased proliferation when modified with TNC III1-5 (p<0.05). As shown in FIG. 19, the addition of the fibronectin integrin binding domain FN III9*-10 to TNC III1-5 significantly enhanced smooth muscle cell (SMC) proliferation on top of a PEG gel.

An embodiment of a heparin binding peptide is an isolated polypeptide comprising a heparin binding peptide having at least 85% homology to (a) at least a portion of a Tenascin (TNC) III1-5 domain or a TNC III5 domain, or (b) at least a portion of a fibrinogen β15-66 domain. The detailed sequences for these domains are listed below. The heparin binding peptide may comprise at least a portion of a Tenascin III3-5 domain. As discussed, the heparin binding peptides bind certain cytokines. Embodiments this include a polypeptide wherein the heparin binding peptide binds one or more, e.g., at least 10 or at least twenty of the growth factors or growth factor-binding proteins chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF. The IGF-BPs are binding proteins (BPs) to growth factors. Artisans will immediately appreciate that all the ranges and values within the explicitly stated ranges are contemplated, so that a homology of at least 90%, 95%, or 99% is contemplated. Further, the portion of the domain may range in size, provided it retains the indicated function, e.g., from 50% to 100% of the total residues; artisans will immediately appreciate that all the ranges and values within the explicitly stated ranges are contemplated. Artisans having reviewed this disclosure will readily be able to determine operable truncations of the full sequences that are provided herein, with such optimization being routine. Moreover, conservative substitutions of between 0% to 15% of the residues may be readily identified. Artisans can easily determine if a particular sequence meets these criteria merely by making a comparison to the disclosed sequences and assaying suitable cytokine binding.

Certain embodiments are directed to a composition comprising a peptide, or an isolated (or purified) peptide, comprising a number of consecutive amino acid sequences between about 70% and 100% of the consecutive amino acid residues of a sequence chosen from the group consisting of SEQ ID NOs 1, 9, 2, 8, 3, 4, 5, 6, or 7, and conservative substitutions thereof, wherein said sequence provides a cytokine binding function. Alternatively the number of consecutive residues may be chosen to be more than about 85%, more than about 90%, more than about 95%, and so forth; artisans will immediately appreciate that all the ranges and values within the explicitly stated ranges are contemplated, e.g., 99% or 98%. The sequence may have, e.g., a conservative substitution of at least one and no more than two amino acids of the sequences, or 1, 2, or 3 substitutions, or between 1 and 5 substitutions. Moreover, the substitution of L-amino acids in the discovered sequence with D-amino acids can be frequently accomplished, as in Giordano. The peptide may further comprise a bioactive agent, e.g., a therapeutic agent.

Data herein shows that the specific binding domains could be part of a molecular fusion and retain function. Indeed, many sequences in the biological arts are known to be effective when they are part of even very large molecules, e.g., the RGD cell adhesion motif. Even though some molecules will fold in a way that confounds the specific binding of such relatively small sequences, artisans are very familiar with techniques for creating even very large molecules that employ such sequences in an effective manner.

Certain embodiments provide various polypeptide sequences and/or purified or isolated polypeptides. A polypeptide is a term that refers to a chain of amino acid residues, regardless of post-translational modification (e.g., phosphorylation or glycosylation) and/or complexation with additional polypeptides, synthesis into multisubunit complexes, with nucleic acids and/or carbohydrates, or other molecules. Proteoglycans therefore also are referred to herein as polypeptides. As used herein, a "functional polypeptide" is a polypeptide that is capable of promoting the indicated function. Polypeptides can be produced by a number of methods, many of which are well known in the art. For example, polypeptides can be obtained by extraction (e.g., from isolated cells), by expression of a recombinant nucleic acid encoding the polypeptide, or by chemical synthesis. Polypeptides can be produced by, for example, recombinant technology, and expression vectors encoding the polypeptide introduced into host cells (e.g., by transformation or transfection) for expression of the encoded polypeptide.

There are a variety of conservative changes that can generally be made to an amino acid sequence without altering activity. These changes are termed conservative substitutions or mutations; that is, an amino acid belonging to a grouping of amino acids having a particular size or characteristic can be substituted for another amino acid. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Conservative substitutions also include substituting optical isomers of the sequences for other optical isomers, specifically D amino acids for L amino acids for one or more residues of a sequence. Moreover, all of the amino acids in a sequence may undergo a D to L isomer substitution. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free $NH_2$. Moreover, point mutations, deletions, and insertions of the polypeptide sequences or corresponding nucleic acid sequences may in some cases be made without a loss of function of the polypeptide or nucleic acid fragment. Substitutions may include, e.g., 1, 2, 3, or more residues. The amino acid residues described herein employ either the single letter amino acid designator or the three-letter abbreviation. Abbreviations used herein are in keeping with the standard polypeptide nomenclature, J. Biol. Chem., (1969), 243, 3552-3559. All amino acid residue sequences are represented herein by formulae with left and right orientation in the conventional direction of amino-terminus to carboxy-terminus.

In some cases a determination of the percent identity of a peptide to a sequence set forth herein may be required. In such cases, the percent identity is measured in terms of the number of residues of the peptide, or a portion of the peptide. A polypeptide of, e.g., 85%, 90%, or 95% identity, may also be a portion of a larger peptide.

The term purified as used herein with reference to a polypeptide refers to a polypeptide that has been chemically synthesized and is thus substantially uncontaminated by other polypeptides, or has been separated or purified from other most cellular components by which it is naturally accompanied (e.g., other cellular proteins, polynucleotides, or cellular components). An example of a purified polypeptide is one that is at least 70%, by dry weight, free from the proteins and naturally occurring organic molecules with which it naturally associates. A preparation of the purified polypeptide therefore can be, for example, at least 80%, at least 90%, or at least 99%, by dry weight, the polypeptide. Polypeptides also can be engineered to contain a tag sequence (e.g., a polyhistidine tag, a myc tag, or a FLAG® tag) that facilitates the polypeptide to be purified or marked (e.g., captured onto an affinity matrix, visualized under a microscope). Thus a purified composition that comprises a polypeptide refers to a purified polypeptide unless otherwise indicated. The term isolated indicates that the polypeptides or nucleic acids of the invention are not in their natural environment. Isolated products of the invention may thus be contained in a culture supernatant, partially enriched, produced from heterologous sources, cloned in a vector or formulated with a vehicle, etc.

Polypeptides may include a chemical modification; a term that, in this context, refers to a change in the naturally-occurring chemical structure of amino acids. Such modifications may be made to a side chain or a terminus, e.g., changing the amino-terminus or carboxyl terminus. In some embodiments, the modifications are useful for creating chemical groups that may conveniently be used to link the polypeptides to other materials, or to attach a therapeutic agent.

Specific binding, as that term is commonly used in the biological arts, refers to a molecule that binds to a target with a relatively high affinity compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and specifically binding protein-receptor interactions; while such molecules may bind tissues besides their targets from time to time, such binding is said to lack specificity and is not specific binding.

Further embodiments related to a pharmaceutically acceptable compound comprising a heparin binding peptide specifically bound to a cytokine. The peptide may be part of a molecular fusion, a polymer, part of a biomaterial, or be free of any of the foregoing. The compound may comprise a plurality of heparin binding peptides specifically bound to a cytokine, e.g., one or more growth factors or growth factor-binding proteins chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF.

A preferred embodiment is a pharmaceutically acceptable molecular complex between TNC III1-5 or smaller regions within that domain and cytokines. The term molecular complex (or sometimes called a molecular conjugate), refers to a biophysical binding interaction produced by presenting the two partners in the complex, namely the TNC III1-5 domain and the cytokine. Simple mixing of the two biomolecules can lead to formation of the molecular complex. It is demonstrated herein that TNC III1-5 binds to FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF. A preferred embodiment is a molecular complex between TNC III5 and a cytokine.

A preferred embodiment is a pharmaceutically acceptable molecular complex between Fg β15-66 and a cytokines. A preferred embodiment is a pharmaceutically acceptable molecular complex between Fg β15-66 and VEGF-A165, VEGF-B, PlGF-2, PlGF-3, PDGF-AB, PDGF-BB, FGF-2, FGF-5, FGF-7, FGF-10, TGF-β1, TGF-β2, BMP-2, BMP-2/7, NT-3, BDNF, IGFBP-3 or IGFBP-5.

The molecular complexes between Fg β15-66 and cytokines can be further immobilized into biomaterial matrices, forming additional preferred embodiments. The protein containing the Fg β15-66 domain can be fused to a transglutaminase (TG) substrate that can covalently bind to natural protein biomaterials such as fibrin biomaterial or to synthetic biomaterials engineered to comprise counter-substrates for transglutaminases. A preferred embodiment is a biomaterial matrix that comprises bound Fg β15-66. A preferred embodiment is a biomaterial matrix that further comprises molecular complexes between the Fg β15-66 domain and cytokines. A preferred embodiment is a pharmaceutical formulation of a tissue repair matrix comprising the Fg β15-66 domain and a cytokine, including molecular complexes with cytokines, the cytokines or cytokine-biding proteins including VEGF-A165, VEGF-B, PlGF-2, PlGF-3, PDGF-AB, PDGF-BB, FGF-2, FGF-5, FGF-7, FGF-10, TGF-β1, TGF-β2, BMP-2, BMP-2/7, NT-3, BDNF, IGFBP-3 and IGFBP-5.

Molecular Fusion

Embodiments include a heparin binding peptide in a molecular fusion with a bioactive agent, e.g., a therapeutic agent, marker, cell adhesion molecule, antigen, protein, protein drug, or cytokine. A molecular fusion may be formed between a first heparin binding peptide and a second peptide. Instead of second peptide a chemical moiety may be used, e.g., a marker, fluorescent marker. The fusion comprises the peptides conjugated directly or indirectly to each other. The peptides may be directly conjugated to each other or indirectly through a linker. The linker may be a peptide, a polymer, an aptamer, a nucleic acid, or a particle. The particle may be, e.g., a microparticle, a nanoparticle, a polymersome, a liposome, or a micelle. The polymer may be, e.g., natural, synthetic, linear, or branched. A fusion protein that comprises the first peptide and the second peptide is an example of a molecular fusion of the peptides, with the fusion protein comprising the peptides directly joined to each other or with intervening linker sequences and/or further sequences at one or both ends. The conjugation to the linker may be through covalent bonds. Methods include preparing a molecular fusion or a composition comprising the molecular fusion, including such a composition in a pharmaceutically acceptable form.

Embodiments include a molecular fusion of a polypeptide that comprises a heparin binding peptide and a transglutaminase substrate (TG). An embodiment of a TG substrate is a peptide that comprises residues 1-8 of alpha 2-plasmin inhibitor (NQEQVSPL) (SEQ ID NO:10). Embodiments include such a polypeptide being a recombinant fusion polypeptide. The molecular fusion may be further comprising a cell adhesion moiety having a specific binding affinity for a cell adhesion molecule. Various cell adhesion moieties are known, for instance, wherein the cell adhesion moiety comprises a ligand for a glycoprotein or a cell surface receptor. Or the cell adhesion moiety may comprise a ligand with specific binding to the cell adhesion molecule and the cell adhesion molecule is a cell surface receptor chosen from the group consisting of an integrin, and a cadherin. Or the cell adhesion moiety may comprise an integrin-binding peptide chosen from the group consisting of Tenascin III3, an RGD sequence. Embodiments include the polypeptide being a fusion polypeptide and further comprising a fibronectin III9 domain, fibronectin III9* domain, fibronectin III9-10 domain, or a fibronectin III9*-10 domain. Embodiments include the polypeptide comprising the fibronectin III9-10 domain and a HBD sequence taken from a domain chosen from the group consisting of TNC III1-5, TNCIII3-5, and TNC III5. Embodiments include the polypeptide comprising the fibronectin III9*-10 domain and a HBD sequence taken from a domain chosen from the group consisting of TNC III1-5, TNCIII3-5, and TNC III5.

The term molecular fusion, or the term conjugated, refers to direct or indirect association by chemical bonds, including covalent, electrostatic ionic, or charge-charge. The conjugation creates a unit that is sustained by chemical bonding. Direct conjugation refers to chemical bonding to the agent, with or without intermediate linkers or chemical groups. Indirect conjugation refers to chemical linkage to a carrier. The carrier may largely encapsulate the agent, e.g., a polymersome, a liposome or micelle or some types of nanoparticles, or have the agent on its surface, e.g., a metallic nanoparticle or bead, or both, e.g., a particle that includes some of the agent in its interior as well as on its exterior. The carrier may also encapsulate an antigen for immunotolerance. For instance a polymersome, liposome, or a particle may be made that encapsulates the antigen. The term encapsulate means to cover entirely, effectively without any portion being exposed, for instance, a polymersome may be made that encapsulates an antigen or an agent.

Conjugation may be accomplished by covalent bonding of the peptide to another molecule, with or without use of a linker. The formation of such conjugates is within the skill of artisans and various techniques are known for accomplishing the conjugation, with the choice of the particular technique being guided by the materials to be conjugated. The addition of amino acids to the polypeptide (C- or N-terminal) which contain ionizable side chains, i.e. aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, i.e. homo- or hetero-bi-functional PEG (e.g., Lutolf and Hubbell, *Biomacromolecules* 2003; 4:713-22, Hermanson, *Bioconjugate Techniques*, London. Academic Press Ltd; 1996). In some embodiments, a soluble polymer linker is used, and may be administered to a patient in a pharmaceutically acceptable form. Or a drug may be encapsulated in polymerosomes or vesicles or covalently attached to the peptide ligand.

The molecular fusion may comprise a particle. The heparin binding peptide may be attached to the particle. An antigen, agent, or other substance may be in or on the particle. Examples of nanoparticles, micelles, and other particles are found at, e.g., US 2008/0031899, US 2010/0055189, US 2010/0003338, which applications are hereby incorporated by reference herein for all purposes, including combining the same with a ligand as set forth herein; in the case of conflict, however, the instant specification controls.

Nanoparticles may be prepared as collections of particles having an average diameter of between about 10 nm and about 200 nm, including all ranges and values between the explicitly articulated bounds, e.g., from about 20 to about 200, and from about 20 to about 40, to about 70, or to about 100 nm, depending on the polydispersity which is yielded by the preparative method. Various nanoparticle systems can be utilized, such as those formed from copolymers of poly (ethylene glycol) and poly(lactic acid), those formed from copolymers of poly(ethylene oxide) and poly(beta-amino ester), and those formed from proteins such as serum albumin. Other nanoparticle systems are known to those skilled in these arts. See also Devalapally et al., *Cancer Chemother Pharmacol.*, Jul. 25, 2006; Langer et al., *International Journal of Pharmaceutics*, 257:169-180 (2003); and Tobío et al., *Pharmaceutical Research*, 15(2):270-275 (1998).

Larger particles of more than about 200 nm average diameter incorporating the heparin binding ligands may also be prepared, with these particles being termed microparticles herein since they begin to approach the micron scale and fall approximately within the limit of optical resolution. For instance, certain techniques for making microparticles are set forth in U.S. Pat. Nos. 5,227,165, 6,022,564, 6,090,925, and 6,224,794.

Functionalization of nanoparticles to employ targeting capability requires association of the targeting polypeptide with the particle, e.g., by covalent binding using a bioconjugation technique, with choice of a particular technique being guided by the particle or nanoparticle, or other construct, that the polypeptide is to be joined to. In general, many bioconjugation techniques for attaching peptides to other materials are well known and the most suitable technique may be chosen for a particular material. For instance, additional amino acids may be attached to the polypeptide sequences, such as a cysteine in the case of attaching the polypeptide to thiol-reactive molecules.

The molecular fusion may comprise a polymer. The polymer may be branched or linear. The molecular fusion may comprise a dendrimer. In general, soluble hydrophilic biocompatible polymers may be used so that the conjugate is soluble and is bioavailable after introduction into the patient. Examples of soluble polymers are polyvinyl alcohols, polyethylene imines, and polyethylene glycols (a term including polyethylene oxides) having a molecular weight of at least 100, 400, or between 100 and 400,000 (with all ranges and values between these explicit values being contemplated). Solubility in this context refers to a solubility in water or physiological saline of at least 1 gram per liter. Domains of biodegradable polymers may also be used, e.g., polylactic acid, polyglycolic acid, copolymers of polylactic and polyglycolic acid, polycaprolactones, polyhydroxy butyric acid, polyorthoesters, polyacetals, polydihydropyrans, and polycyanoacylates.

Embodiments include a polymer comprising a polypeptide comprising a synthetic heparin binding peptide, with the heparin binding peptide having at least 85% homology to at least a portion of a Tenascin (TNC) III1-5 domain or a TNC III5 domain, wherein the polymer is not TNC or having at least 85% homology to at least a portion of a fibrinogen β15-66 domain wherein the polymer is not fibrinogen. For example embodiments include the polymers listed above as well as a polysaccharide, polyethylene glycol, polyalkylene oxide, collagen, or gelatin. The polymer may further comprises a transglutaminase substrate (TG), a cytokine, with the cytokine being specifically bound by the heparin binding peptide.

In some embodiments, a polypeptide-polymer association, e.g., a molecular fusion, is prepared and introduced into the body as a purified composition in a pharmaceutically acceptable condition, or with a pharmaceutical excipient. The site of introduction may be, e.g., systemic, or at a tissue or a transplantation site.

Embodiments include a solution comprising a molecular fusion. Examples of a solution are: a cell culture medium; a cell culture medium supplement; a sterile solution; a sterile aqueous solution; a pharmaceutically acceptable solution. A preferred embodiment is a cell culture supplement comprising the TNC III1-5 domain. A preferred embodiment is a cell culture surface comprising the TNC III1-5 domain. A preferred embodiment is a cell culture supplement comprising the TNC III3-5 domain. A preferred embodiment is a cell culture surface comprising the TNC III35 domain. A preferred embodiment is a cell culture supplement comprising the TNC III5 domain. A preferred embodiment is a cell culture surface comprising the TNC III5 domain.

Since the TNC III1-5 domain is constituted of FN type III repeats, it may be further engineered to provide additional adhesion domains from proteins other than TNC, such as the FN III 9-10 cell binding domain from FN, the FN III9*-10 variant cell binding domain from FN, or any other cell binding domain from FN type III repeats from both TNC and FN.

Processes of cell adhesion, proliferation, migration, and differentiation are tightly regulated by integrin receptors. Especially, these cellular processes required synergistic signals between integrins and cytokine receptors. For example, endothelial cell and mesenchymal stem cells adhesion, proliferation, migration, and/or differentiation are dependent of the cooperation between $\alpha_5\beta_1$ integrin and cytokine receptors (Martino, Tortelli, et al., 2011). Because some integrins such as the integrin $\alpha_5\beta_1$ require an additional sequence next to RGD to transmit signals, the addition of other integrin binding sites or sequences to TNC III1-5, TNC III3-5, or TNC III5 would potentiate the cooperation of stronger signals to control cellular processes into TNC fragments that bind cytokines.

A preferred embodiment is the fusion protein FN III9-10-TNC III1-5 or such a fusion protein with a smaller domain from TNC III1-5, including FN III9-10-TNC III3-5 and FN III9-10-TNC III5. A preferred embodiment is the fusion protein FN III9*-10-TNC III1-5 or such a fusion protein with a smaller domain from TNC III1-5, including FN III9*-10-TNC III3-5 and FN III9*-10-TNC III5. A preferred embodiment is a pharmaceutical formulation of a tissue repair matrix comprising a biomaterial matrix bound to the fusion protein FN III9-10-TNC III1-5 or such a fusion protein with a smaller domain from TNC III1-5, including FN III9-10-TNC III3-5 and FN III9-10-TNC III5. A preferred embodiment is a pharmaceutical formulation of a tissue repair matrix comprising a biomaterial matrix bound to the fusion protein FN III9*-10-TNC III1-5 or such a fusion protein with a smaller domain from TNC III1-5, including FN III9*-10-TNC III3-5 and FN III9*-10-TNC III5.

Scaffolds

Scaffolds are matrices. The term matrix refers to a three-dimensional structure, including a block, sheet, or film; it is a term used in contrast to a soluble or fluid material. The scaffolds have to withstand mechanical loads, contain suitable degradation kinetics, and present bioactive molecules. Scaffolds function as a fusion of cell carrier and drug delivery device for the purpose of tissue engineering. To mimic the natural microenvironment for cells in order to induce tissue repair and regeneration, synthetic materials can be modified with ECM fragments. ECM fragments described in this report may be designed to form a molecular fusion with a transglutaminase (TG) substrate at the N terminus, consisting of residues 1-8 of the protein alpha2 plasmin inhibitor (α2PI-8, NQEQVSPL (SEQ ID NO:10)). Factor XIIIa can therefore be used as a transglutaminase to catalyze the reaction between the glutamines of this sequence (NQEQVSPL) (SEQ ID NO:10)) and the lysines of different biomaterials. The coagulation enzyme, factor XIIIa, will covalently bind the free amine group of the lysines (Lys) to the gamma-carboxamid group of glutamine (Gln), resulting in bonds that exhibit high resistance to proteolytic degradation. For example, natural fibrin hydrogels are cross-linked by this mechanism and TG-TNC III1-5 can therefore be cross-linked inside the gel (Schense and Hubbell, 1999).

Modification of synthetic hydrogels with TG-TNC III1-5 is possible by engineering counter-substrates for transglutaminases, such as lysines inside poly ethylene glycol (PEG-Lys) hydrogels. PEG is modified with lysines by chemically cross-linking a lysine containing peptide that includes a cysteine to form a disulfide-bridged polymer conjugate with PEG-vinyl sulfone (PEG-VS). The SH group of the cysteine functions as nucleophile (Mikael donor) in a Mikael type addition, with VS functioning as Michael acceptor (Lutolf, Lauer-Fields, et al., 2003). This technology has been used to make TG-PEG gels, which are cross-linked by two multi-arm PEG-peptide conjugates, PEG-Lys and PEG-Gln, in the presence of factor XIII, which allows for incorporation of other proteins containing a TG substrate (Ehrbar, Rizzi, et al., 2007). Alternatively, TNC III1-5 can be produced with a cysteine to chemical crosslink the fragment directly into a PEG-VS gel.

The molecular complexes between TNC III1-5 or smaller regions within that domain and cytokines can be further immobilized into biomaterial matrices, forming additional preferred embodiments. The protein containing the TNC III1-5 domain, or smaller domains such as TNC III3-5 or TNC III5, can be fused to a transglutaminase substrate that can covalently bind to natural protein biomaterials such as fibrin or to synthetic biomaterials engineered to comprise counter-substrates for transglutaminases. We produced domain TG-TNC III1-5 to obtain a stable protein including domain TNC III3 as integrin binding domain and TNCIII5 to bind cytokines, with an additional TG domain for fibrin and biomaterial incorporation. Thus, a preferred embodiment is a fusion between TNC III1-5 and a TG domain for immobilization to fibrin or a biomaterial matrix under the influence of factor XIIIa A preferred embodiment is a fusion between TNC III3-5 and a TG domain. A preferred embodiment is a fusion of TNC III5 and a TG domain.

A preferred embodiment is a pharmaceutical formulation of a tissue repair matrix comprising a biomaterial matrix bound to the fusion protein FN III9-10-TNC III1-5 or such a fusion protein with a smaller domain from TNC III1-5, including FN III9-10-TNC III3-5 and FN III9-10-TNC III5, that further comprises a molecular complex with a cytokine, the cytokines including FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, or HGF. A preferred embodiment is a pharmaceutical formulation of a tissue repair matrix comprising a biomaterial matrix bound to the fusion protein FN III9*-10-TNC III1-5 or such a fusion protein with a smaller domain from TNC III1-5, including FN III9*-10-TNC III3-5 and FN III9*-10-TNC III5, that further comprises a molecular complex with a cytokine, the cytokines including FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, or HGF.

A preferred embodiment is a biomaterial matrix that comprises bound TNC III1-5 or smaller regions within that domain. A preferred embodiment is a biomaterial matrix that further comprises molecular complexes between the TNC III1-5 domain and cytokines. Further preferred embodiments are formed from smaller domains within TNC III1-5, specifically TNC III3-5 and especially TNC III5.

A preferred embodiment is a pharmaceutical formulation of a biomaterial matrix comprising the TNC III1-5 domain or a smaller region within that domain, such as TNC III3-5 or TNC III5, and a cytokine, including molecular complexes with cytokines, the cytokines including FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, or HGF.

An embodiment is a biomaterial matrix comprising a polymeric matrix that comprises a polypeptide that comprises a plurality of heparin binding domains (HBD) having at least 85% homology to at least a portion of a Tenascin (TCN) III1-5 domain or at least a portion of a TNC III5 domain and one or more cytokines specifically bound to the HBDs. The biomaterial matrix may be made comprising at least three cytokines specifically bound to an HBD, with each of the three cytokines filling at least about 5% of the HBDs present in the matrix.

An embodiment is a biomaterial scaffold comprising a polymeric matrix that comprises a polypeptide that comprises a plurality of heparin binding domains (HBD) having at least 85% homology to at least a portion of a fibrinogen β15-66 domain, and at least three cytokines specifically bound to an HBD, with each of the three cytokines filling at least about 5% of the HBDs present in the matrix.

An embodiment is a biomaterial scaffold comprising a polypeptide comprising a synthetic heparin binding domains (HBD), with the HBD having at least 85% homology to at least a portion of a Tenascin (TNC) III1-5 domain or at least a portion of a TNC III5 domain wherein the polymer is not TNC or having at least 85% homology to at least a portion of a fibrinogen β15-66 domain wherein the polymer is not fibrinogen, wherein the polypeptide further comprises a transglutaminase substrate, with the polypeptide being covalently linked by a transglutaminase-medicated chemical reaction that covalently links the substrate to the matrix. The biomaterial scaffold may be made comprising copolymers that comprise a transglutaminase substrate, with the copolymers being covalently linked to each other with bonds formed by a transglutaminase enzyme. The copolymers may comprise a hydrophilic polymer (a polymer having a solubility of at least 1 g/100 ml water). The biomaterial scaffold may be made further comprising at least three cytokines specifically bound to an HBD, with each of the three cytokines filling at least about 5% of the HBDs present in the matrix. The biomaterial scaffold may be made wherein the cytokines are chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, and HGF. Additionally or alternatively, the cytokines may comprise IGF-1 bound via IGF-BP3 or IGF-BP5. The biomaterial scaffold may be made wherein the TG substrate comprises residues 1-8 of alpha2-plasmin inhibitor (NQEQVSPL) (SEQ ID NO:10). The biomaterial scaffold may be made with the polypeptide being a recombinant fusion polypeptide and further comprising a cell adhesion moiety having a specific binding affinity for a cell adhesion molecule. The biomaterial scaffold may be made wherein the cell adhesion moiety comprises a ligand with specific binding to a glycoprotein or a cell surface receptor. The biomaterial scaffold may be made wherein the cell adhesion moiety comprises a ligand with specific binding to the cell adhesion molecule and the cell adhesion molecule is a cell surface receptor chosen from the group consisting of an integrin, and a cadherin. The biomaterial scaffold may be made wherein the cell adhesion moiety comprises an integrin-binding peptide chosen from the group consisting of Tenascin III3 and an RGD sequence. The biomaterial scaffold may be made with the polypeptide being a fusion polypeptide and further comprising at least a portion of one of more of: a fibronectin III9 domain, fibronectin III9* domain, fibronectin III9-10 domain, or a fibronectin III9*-10 domain. The biomaterial scaffold may be made comprising the fibronectin III9-10 domain and a HBD sequence taken from a domain chosen from the group consisting of TNC III1-5, TNCIII3-5, and TNC III5. The biomaterial scaffold may be made comprising the fibronectin III9*-10 domain and a HBD sequence taken from a domain chosen from the group consisting of TNC III1-5, TNCIII3-5, and TNC III5. The biomaterial scaffold may be made for providing a sterile and pharmaceutically acceptable tissue repair matrix, for example: for skin tissue, nerve tissue, or bone tissue. The biomaterial scaffold may be made comprising one or more of VEGF-A165, PDGF-BB, BMP-2, NT-3, and BDNF.

Fibrin is a useful base matrix, and heparin binding peptides and molecular fusions described herein may be used with the same. Other materials may also be engineered to include TG or moieties that interact with transglutaminases to receive a TG molecular fusion. U.S. Pat. Nos. 7,241,730, 6,331,422, 6,607,740, 6,723,344, US Pub 2007/0202178, US Pub 2007/0264227 are hereby incorporated herein by reference for all purposes; in case of conflict, the specification is controlling.

Tissue Regeneration, Healing, and Treatment

Example 18 provides a demonstration of improving tissue healing with a molecular fusion of a heparin binding domain. The domain was fused with a TG and incorporated into a biomaterial matrix with a transglutaminase. The heparin binding peptide was effective for delivering cytokines. The model was a TG-to-Fg β15-66 molecular fusion within PEG gels as assessed by using a diabetic wound healing animal model. Functionalized matrices with above mentioned TNC, FN, fibrinogen fragments may be used to enhance skin healing. Preclinical evaluations of cytokines for chronic skin-wound healing are generally performed in rodents and most commonly in the db/db diabetic mouse (Hanft, Pollak, et al., 2008; Robson, Phillips, et al., 2001; Robson, Phillips, et al., 1992; Robson, Phillips, et al., 1992). These models are accepted as being predictive, despite the fact that the optimal disease model does not yet exist for human chronic wounds. Nevertheless, there is consensus that the genetically modified db/db mouse represents a clinically relevant model for diabetes-impaired skin-wound healing (Sullivan, Underwood, et al., 2004; Davidson, 1998). Success in the db/db mouse model directly opens the way for clinical trials (Hanft, Pollak, et al., 2008; Robson, Phillips, et al., 1992). Compared to wild-type mice, this strain heals wounds principally by the formation of granulation tissue rather than by contraction, and its impairment is due to lower levels of several GFs and receptors (Davidson, 1998).

Full-thickness back-skin wounds of these mice (4 wounds per mouse) would be treated with a low dose of combined cytokines (for example 100 ng of VEGF-A165 and 100 ng of PDGF-BB) delivered by a matrix functionalized with TNC fragment. Wound histology would be analyzed after 7, 10, or 15 days. Cytokines delivered in matrices only would be ineffective, given the low dose administered and the lack of smart delivery system. For example, 20 µg/wound of VEGF-A165 or 10 µg/wound of PDGF-BB (REGRANEx®) applied topically for five consecutive days has been reported to be efficient in the db/db mouse (Chan, Liu, et al., 2006; Galiano, Tepper, et al., 2004). Thus, the wounds that receive matrices containing cytokines only should not differ from wounds treated with matrix alone, in either amount of granulation tissue or extent of wound closure (the latter indicated by re-epithelialization). In contrast, the delivery of cytokines in TNC fragments—modified matrix would led to significantly faster wound closure and greater development of granulation tissue. Angiogenesis is a crucial step in sustaining newly formed granulation tissue within the wound bed (Gurtner, Werner, et al., 2008). As such, higher percentages of $CD31^+$ endothelial cells would be present in the wounds treated with cytokines delivered by TNC fragment-functionalized matrices compared to wounds treated with the cytokines only. Immuohistological analysis for CD31 and desmin (an smooth muscle cells marker) should confirm that angiogenesis within the granulation tissues is more pronounced when cytokines are delivered within TNC fragments-functionalized matrices.

Examples 19 and 20 provide detailed descriptions for applications of heparin binding peptides for treatment of bone and nerve tissues.

Surface Modifications

Embodiments include a surface modified to contain one or more of the moieties descried herein. In general, techniques for making a molecular fusion can be adapted to modifying a surface, or related techniques known to the artisan are generally available for a wide range of surfaces. Embodiments include a layer or coating of a molecular fusion placed on a surface. Embodiments include a surface comprising one or more immobilized moieties chosen from the group consisting of at least a portion of a Tenascin (TNC) III1-5 domain, at least a portion of a TNC III5 domain, at least a portion of a fibrinogen β15-66 domain, at least a portion of one of more of: a fibronectin III9 domain, fibronectin III9* domain, fibronectin III9-10 domain, or a fibronectin III9*-10 domain.

Embodiments include the surface being chosen from the group consisting of a medical device, a stent, a vascular graft, a cell culture surface, a cell culture vessel, a cell carrier, tissue culture plastic, an affinity column, and a cell separations device. Embodiments include the surface comprising one or more cytokines specifically bound to a heparin binding domain portion of: the TNC III1-5 domain, the TNC III5 domain, or the β15-66 domain. Embodiments include the surface comprising at least three of the cytokines specifically bound to an HBD, with each of the three cytokines filling at least about 5% of the HBDs present in the scaffold. Embodiments include the surface wherein the cytokines are chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF. Embodiments include the surface wherein the moieties are adsorbed or covalently bound.

Cells

The heparin binding peptides have a number of uses for cells. The uses include in vitro uses for cell culture, such as delivery of one or more cytokines, for release of cytokines, for delivery of the same to a cell surface. These uses include ex vivo and in vivo uses for exposing cells to the materials whereby the cells bind the molecular fusions of heparin binding peptides.

An embodiment is a collection of cells, the cells comprising one or more immobilized moieties chosen from the group consisting of at least a portion of a Tenascin (TNC) III1-5 heparin binding domain (HBD), at least a portion of a TNC III5 HBD, at least a portion of a fibrinogen β15-66 domain, at least a portion of one of more of: a fibronectin III9 domain, fibronectin III9* domain, fibronectin III9-10 domain, or a fibronectin III9*-10 domain. An embodiment is the collection comprising at least three of cytokines specifically bound to an HBD, with each of the three cytokines filling at least about 5% of the HBDs present in the scaffold. An embodiment is the collection wherein the cytokines are chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, and HGF or IGF-1 bound via IGF-BP3 or IGF-BP5. An embodiment is the collection wherein the moieties are adsorbed or covalently bound. An embodiment is the collection wherein the immobilized moieties chosen from the group consisting of at least a portion of a Tenascin (TNC) III1-5 domain and at least a portion of a TNC III5 domain.

Antibodies

Embodiments include a composition that blocks specific binding to a heparin binding domain (HBD), the composition comprising an antibody, antibody fragment, scFv, or aptamer that specifically binds the HBD, with the HBD being chosen from the group consisting of a Tenascin (TNC) III1-5 domain, a TNC III5 domain, and a fibrinogen β15-66 domain. An embodiment is a composition wherein the HBD comprises the TNCIII5. An embodiment is a composition wherein the HBD comprises the a fibrinogen β15-66 domain. An embodiment is a composition that comprises the antibody, the antibody fragment, or the scFv. An embodiment is a composition wherein the antibody, the antibody fragment, or the scFv is a humanized antibody or comprises a portion of a humanized antibody. An embodiment is a composition blocks binding of the HBD to one or more cytokines or cytokine-binding proteins are chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF. An embodiment is a composition in a pharmaceutically acceptable formulation. An embodiment is a composition in a pharmaceutically acceptable formulation comprising a pharmaceutically acceptable vehicle or excipient. An embodiment is a composition for treating a cancer comprising any of the antibody-related embodiments herein.

Techniques for raising an antibody against an antigen are well known. The term antigen, in this context, refers to a site recognized by a host immune system that responds to the antigen. Antigen selection is known in the arts of raising antibodies, among other arts. Embodiments include use of these peptides in a molecular fusion and other methods presented herein. Artisans reading this disclosure will be able to create antibodies that specifically bind the indicated domains, and block adhesion of cytokines to the same. Examples 21-22 relate to making antibodies or fragments thereof.

The term peptide is used interchangeably with the term polypeptide herein. Antibodies and antibody fragments are peptides. The term antibody fragment refers to a portion of an antibody that retains the antigen-binding function of the antibody. The fragment may literally be made from a portion of a larger antibody or alternatively may be synthesized de novo. Antibody fragments include, for example, a single chain variable fragment (scFv) An scFv is a fusion protein of the variable regions of the heavy (VH) and light chains (VL) of immunoglobulin, connected with a linker peptide, e.g., about 10 to about 50 amino acids. The linker can either connect the N-terminus of the VH with the C-terminus of the VL, or vice versa. The term scFv includes divalent scFvs, diabodies, triabodies, tetrabodies and other combinations of antibody fragments. Antibodies have an antigen-binding portion referred to as the paratope. The term peptide ligand refers to a peptide that is not part of a paratope. A preferred embodiment is a pharmaceutical formulation of an antibody or antibody fragment that binds to TNC III5 and blocks cytokine binding.

Administration

Pharmaceutically acceptable carriers or excipients may be used to deliver embodiments as described herein. Excipient refers to an inert substance used as a diluent or vehicle for a therapeutic agent. Pharmaceutically acceptable carriers are used, in general, with a compound so as to make the compound useful for a therapy or as a product. In general, for any substance, a carrier is a material that is combined with the substance for delivery to an animal. Conventional pharmaceutical carriers, aqueous, powder or oily bases, thickeners and the like may be necessary or desirable. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in the arts. Thus a pharmaceutically acceptable compositions are highly purified to be free of contaminants, are sterile, biocompatible and not toxic, and further may include a carrier, salt, or excipient suited to administration to a patient. In the case of water as the carrier, the water is highly purified and processed to be free of contaminants, e.g., endotoxins.

The compounds described herein may be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. Thus the deliverable compound may be made in a form suitable for oral, rectal, topical, intravenous injection, intra-articular injection, or parenteral administration. Carriers include solids or liquids, and the type of carrier is chosen based on the type of administration being used. Suitable binders, lubricants, disintegrating agents, coloring agents, flavoring agents, flow-inducing agents, and melting agents may be included as carriers, e.g., for pills. For instance, an active component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. The compounds can be administered orally in solid dosage forms, such as capsules, tablets, and powders, or in liquid dosage forms, such as elixirs, syrups, and suspensions. The active compounds can also be administered parentally, in sterile liquid dosage forms. Buffers for achieving a physiological pH or osmolarity may also be used.

EXAMPLES

Example 1

Production of TNC Domains

TNC III1-5 was expressed in mammalian cells, HEK-293E, using the vector pSecTag A (Invitrogen), which uses an Ig kappa leader sequence for secretion of the TNC fragment out of the cell. The signal sequence is followed by a SfiI cloning site which codes for the amino acids AAQPA. Immediately after the cloning site a factor Xa cleavage site was introduced if it was needed for complete removal of the leader peptide. Following the factor Xa cleavage site, is the transglutaminase substrate, residues 1-8 of alpha2-plasmin inhibitor (NQEQVSPL) (SEQ ID NO:10 A short linking sequence of GGS was added before the addition of the TNC III1-5, residues E622 to A1074. At the C-terminus of the construct is a short linker sequence, GGGS, followed by a 6×His tag (see SEQ ID NO:1).

HEK-293E cells were transfected with 1.25 μg of the plasmid per $10^5$ cells per 1 mL of final growth medium (Excell 293, 4 mM glutamine, 3.75 mM valproic acid). The culture medium was harvested after 7 d of shaker flask expression and cells were removed by filtration. The protein was then purified using and FPLC (Akta Explorer, GE Healthcare) with a HisTrap HP column (GE Healthcare). After elution of the protein, the buffer was change by dialysis within Tris-buffer (20 mM Tris-HCl, 150 mM NaCl, pH 7.4).

```
SEQ ID NO: 1: TNC III1-5 signal sequence, factor
Xa cleavage site, transglutaminase substrate,
the TNC III1-5, with a His tag
METDTLLLWVLLLWVPGSTGDAAQPAIEGRNQEQVSPLGGSEVSPPKDLV

VTEVTEETVNLAWDNEMRVTEYLVVYTPTHEGGLEMQFRVPGDQTSTIIQ

ELEPGVEYFIRVFAILENKKSIPVSARVATYLPAPEGLKFKSIKETSVEV

EWDPLDIAFETWEIIFRNMNKEDEGEITKSLRRPETSYRQTGLAPGQEYE

ISLHIVKNNTRGPGLKRVTTTRLDAPSQIEVKDVTDTTALITWFKPLAEI

DGIELTYGIKDVPGDRTTIDLTEDENQYSI

GNLKPDTEYEVSLISRRGDMSSNPAKETFTTGLDAPRNLRRVSQTDNSIT

LEWRNGKAAIDSYRIKYAPISGGDHAEVDVPKSQQATTKTTLTGLRPGTE
```

-continued

YGIGVSAVKEDKESNPATINAATELDTPKDLQVSETAETSLTLLWKTPLA

KFDRYRLNYSLPTGQWVGVQLPRNTTSYVLRGLEPGQEYNVLLTAEKGRH

KSKPARVKASTEQAGGGSHHHHHH*

SEQ ID NO: 9: TNC III1-5 signal sequence
EVSPPKDLVVTEVTEETVNLAWDNEMRVTEYLVVYTPTHEGGLEMQFRVP

GDQTSTIIQELEPGVEYFIRVFAILENKKSIPVSARVATYLPAPEGLKFK

SIKETSVEVEWDPLDIAFETWEIIFRNMNKEDEGEITKSLRRPETSYRQT

GLAPGQEYEISLHIVKNNTRGPGLKRVTTTRLDAPSQIEVKDVTDTTALI

TWFKPLAEIDGIELTYGIKDVPGDRTTIDLTEDENQYSIGNLKPDTEYEV

SLISRRGDMSSNPAKETFTTGLDAPRNLRRVSQTDNSITLEWRNGKAAID

SYRIKYAPISGGDHAEVDVPKSQQATTKTTLTGLRPGTEYGIGVSAVKED

KESNPATINAATELDTPKDLQVSETAETSLTLLWKTPLAKFDRYRLNYSL

PTGQWVGVQLPRNTTSYVLRGLEPGQEYNVLLTAEKGRHKSKPARVKAST

EQ

Example 2

Production of Fibrinogen Domain cDNAs encoding for human Fg β15-66 was purchased from GenScript, and inserted in the expression vector pGEX-6P-1 for expression as a GST fusion protein supplemented with a C-terminus 6×His-tag. GST-Fg β15-66 was generated in BL21 *E. coli* and purified by GST affinity chromatography (ÄKTA Explorer, GE Healthcare) (Martino, Mochizuki, et al., 2009). The GST-tags were removed using 2 U of PRESCISSION protease (GE Healthcare) per mg of fusion protein. Cleaved fusion proteins were further purified using an HisTrap column (GE Healthcare). Monomers of heparin-binding-domains were dimerized at $Cys_{65}$ by adding 1 mM DTT and dialyzing against Tris buffer (20 mM Tris, 150 mM NaCl, pH 8.0) for 48 h. Monomers and dimers were separated using an HisTrap column (GE Healthcare), and dimers were dialyzed against PBS before storage. Fibrinogen fragments were verified as >99% pure by SDS-PAGE and MALDI-TOF.

SEQ ID NO: 2: GS linker, transglutaminase substrate, the Fg β15-66, with a His tag
GSNQEQVSPLGHRPLDKKREEAPSLRPAPPPISGGGYRARPAKAAATQKK

VERKAPDAGGCGHHHHHH*;

with the Fg β15-66 being
(SEQ ID NO: 8)
GHRPLDKKREEAPSLRPAPPPISGGGYRARPAKAAATQKKVERKAPDAGG

CG

Example 3

Binding of TNC III1-5 Domains to Cytokines

Figure 3:
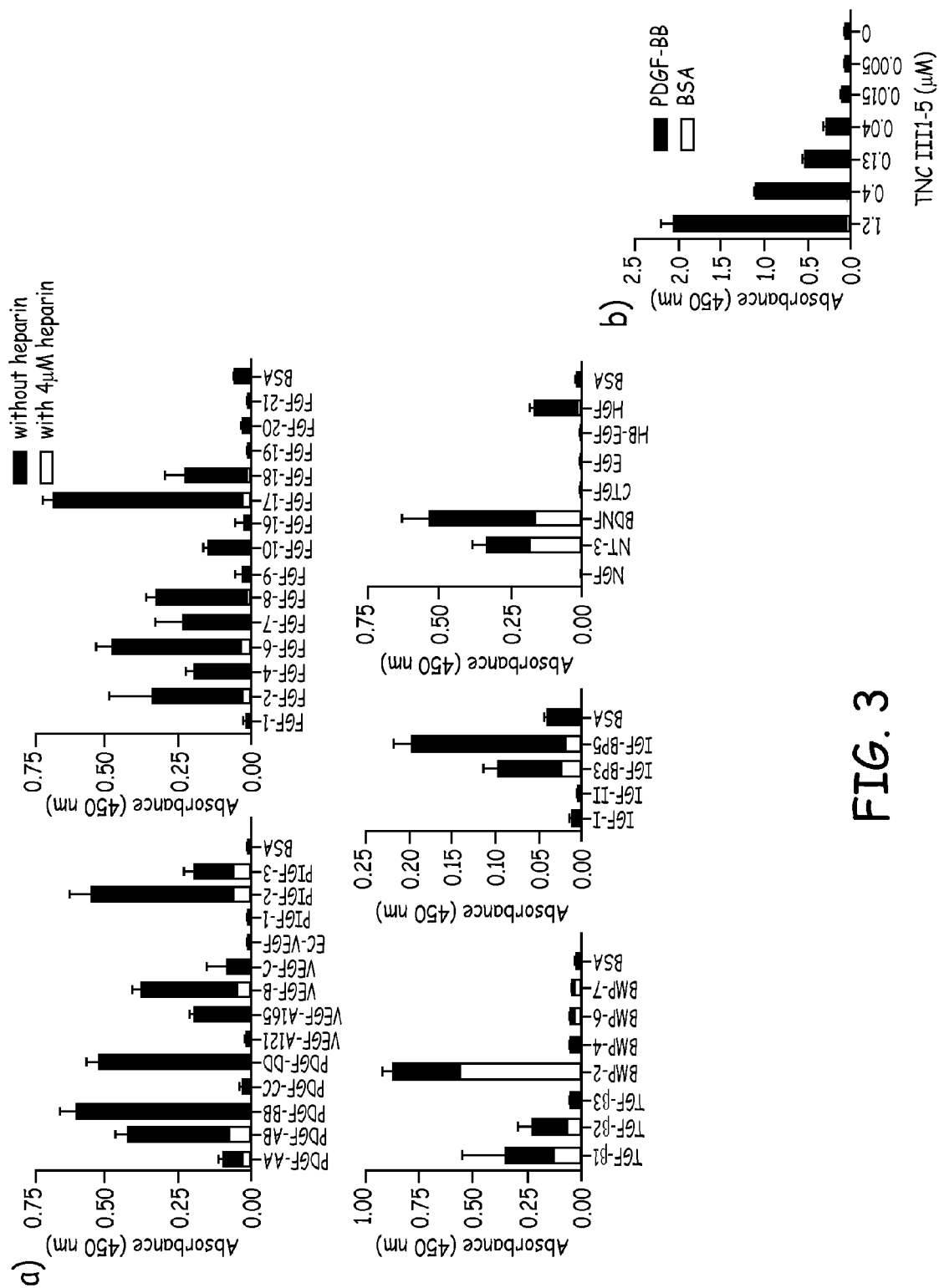
FIG. 3 is a two-panel figure of experimental results. Panel a) Binding of 100 nM TNC III1-5 to cytokines, with and without the presence of 4 μM heparin. Panel b) Binding of different doses of TNC III1-5 to PDGF-BB.

ELISA plates were coated with cytokines or BSA and further incubated with TNC III1-5 to analyze binding of TNC III1-5 to a wide variety of cytokines. The list of cytokines that showed positive binding to TNC III1-5 were FGF-2, FGF-4, FGF-6, FGF-7, FGF-10, FGF-17, FGF-18, TGF-β1, TGF-β2, NT-3, BDNF, PLGF-2, PLGF-1, BMP-2, PDGF-AA, PDGF-AB, PDGF-BB, PDGF-DD, VEGF-A165, VEGF-B, VEGF-C, IGF-BP3, IGF-BP5, HGF. A large amount of heparin (4 µM) impaired binding of TNC III1-5 to these cytokines. Results are depicted in FIG. 3. Method: 50 nM of cytokine was coated for (1 hr, 37° C.). After blocking with 2% BSA (1 hr, RT). 100 nM TNC III1-5 was applied in PBST (0.05% tween, 0.1% bovine serum albumin (BSA)) (1 hr, RT). TNC III1-5 was detected with horseradish peroxidase (HRP)-anti-HIS in PBST (1 hr, RT) and developed with 3,3',5,5'-tetramethylbenzidine (TMB), a soluble colorimetric HRP enzyme. Addition of sulfuric acid stop solution changes the color to yellow, enabling accurate measurement of the intensity at 450 nm using a spectrophotometer or plate reader. A positive signal above background levels, binding to BSA, demonstrated binding of TNC III1-5 to specific morphogens. Heparin (4 µM) was added to TNC III1-5 to test the effect of blocking the heparin binding site of TNC III1-5, which has been defined as domain TNC III5 (Weber, Zimmermann, et al., 1995).

Example 4

Binding of Fg β15-66 to Cytokines

Figure 4A:
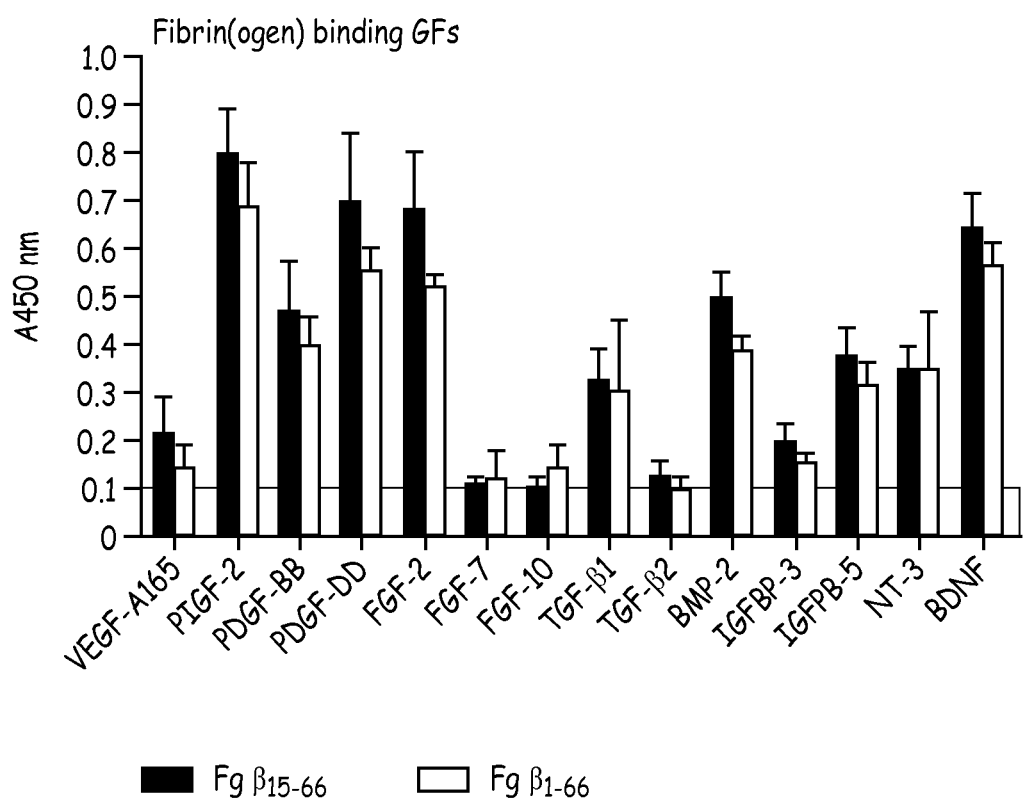
FIG. 4A is a bar graph of experimental results showing growth factors with binding to certain Fg domains.
Figure 4B:
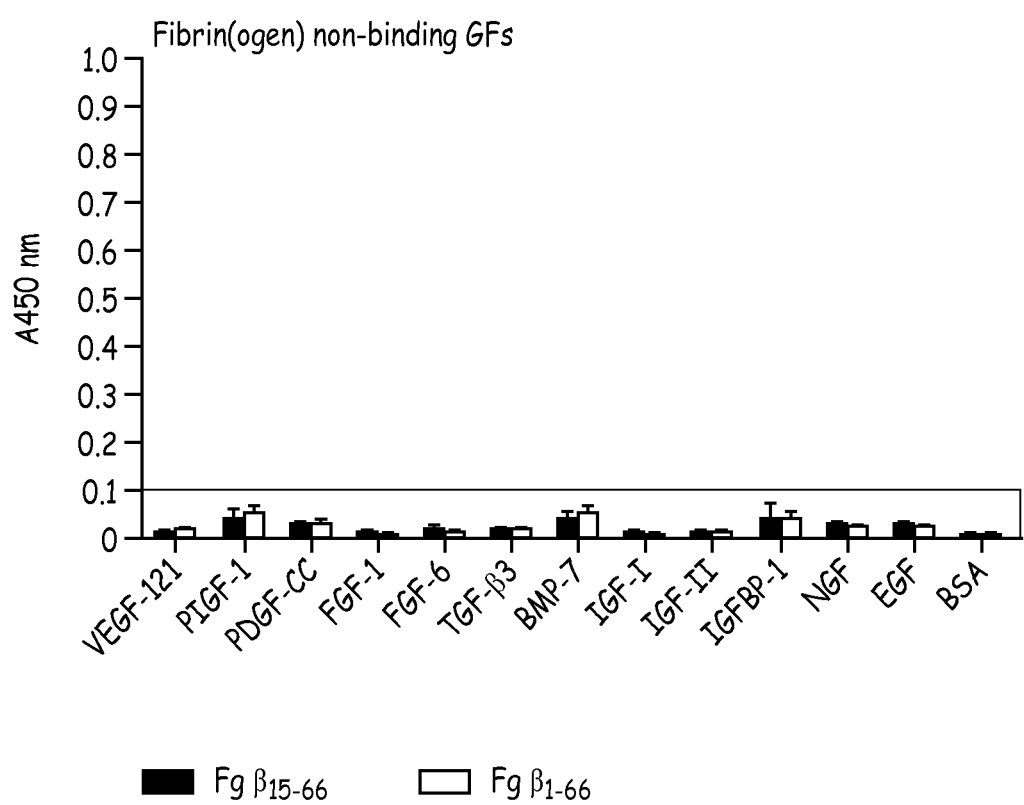
FIG. 4B is a bar graph of experimental results showing growth factors that did not display binding to certain Fg domains.

ELISA plates were coated with cytokines or BSA and further incubated with Fg β15-66 to analyze binding of TNC III1-5 to a wide variety of cytokines. The list of cytokines that showed positive binding to Fg β15-66 were VEGF-A165, VEGF-B, PlGF-2, PlGF-3, PDGF-AB, PDGF-BB, FGF-2, FGF-5, FGF-7, FGF-10, TGF-β1, TGF-β2, BMP-2, BMP-2/7, NT-3, BDNF, IGFBP-3 and IGFBP-5. Results are depicted in FIG. 4. Method: The methods were analogous to those used in Example 3.

Example 5

Affinity of Cytokines to TNC III1-5

Figure 5:
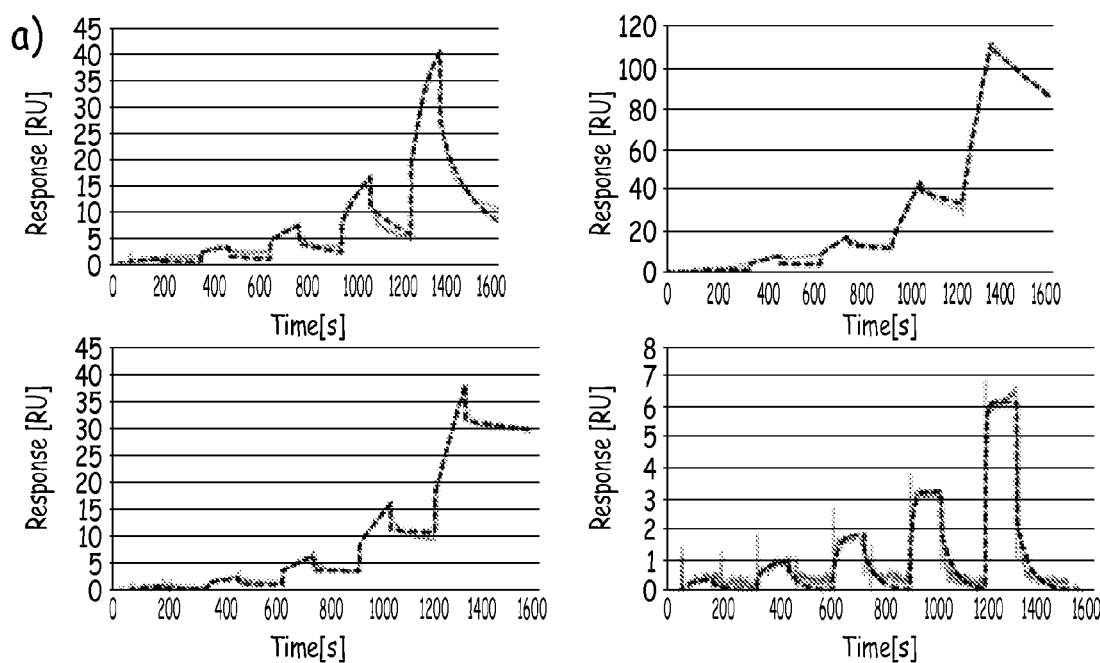
FIG. 5 is a two-panel figure of experimental results: Panel a) Experiment curves (grey full line) of response of TGF-β1, PDGF-BB, NT-3, and FGF-2 respectively to TNC III5 relative to BSA. Fits of the experimental data with Langmuir binding kinetics are shown with black dashed lines; Panel b) Calculation of kinetic parameter, $k_{on}$, $k_{off}$, and $K_D$ ($k_{off}/k_{on}$).

Surface plasmon resonance (SPR) was done to quantify the affinity of specific cytokines to TNC III1-5. $K_D$ affinity values for TGF-β1, PDGF-BB, NT-3, and FGF-2 to TNC III5 were measured to be respectively 20.3 nM, 3.9 nM, 21.0 nM, 15.6, nM, with a lower $K_D$ corresponding to a higher affinity. Method: Surface plasmon resonance chips were functionalized with TNC III1-5 or BSA and cytokines were injected over the chips at different concentrations. The chips contained gold with free carboxyl groups that were activated to bind TNC III1-5 in one channel and BSA as a reference protein in another channel. The specific response of a cytokine to TNC III1-5 (in RU) was obtained relative to the response to BSA. Results are depicted in FIG. 5.

Example 6

Affinity of Cytokines to Fg β15-66

Figure 6:
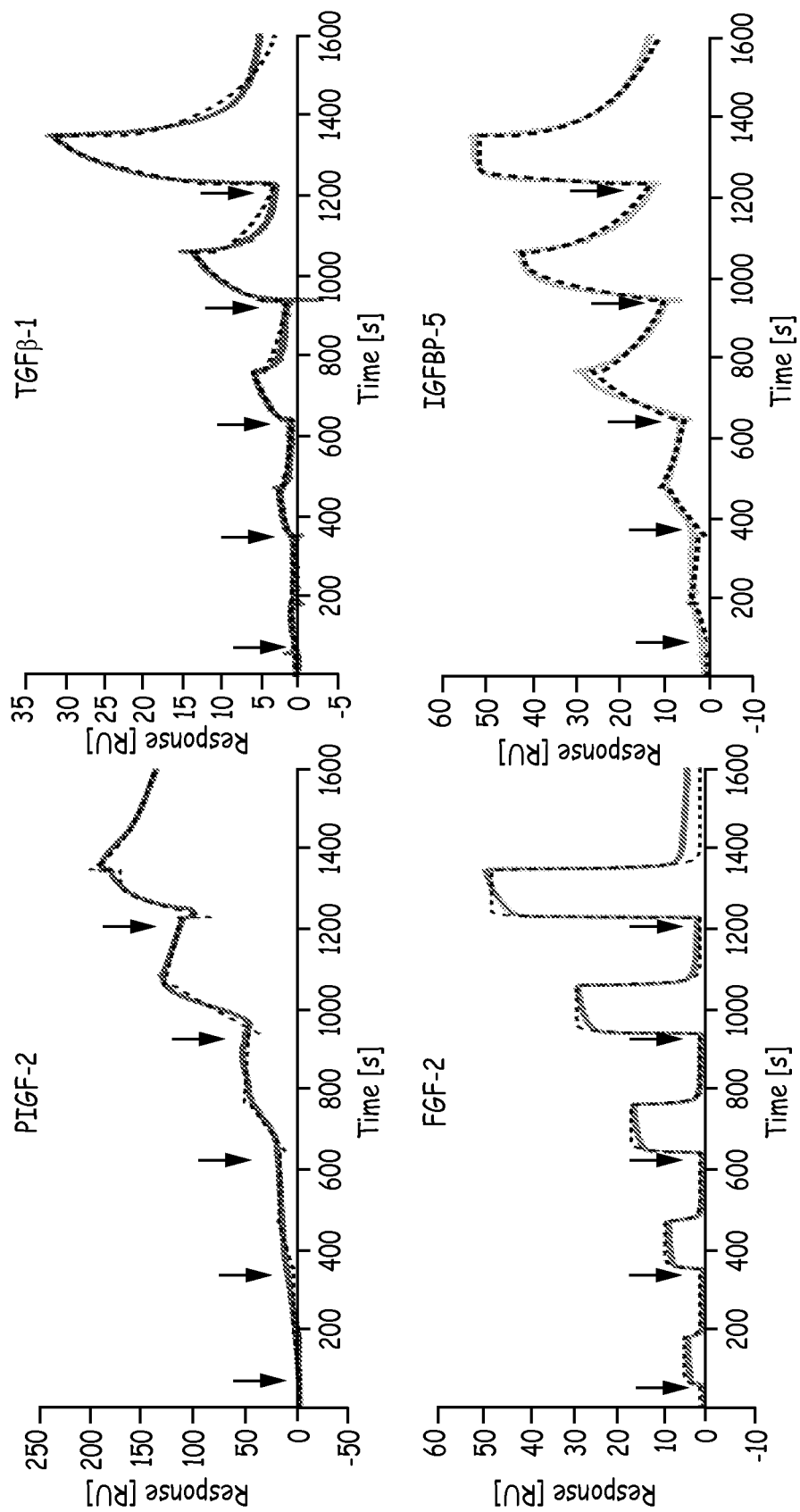
FIG. 6 shows graphs of Experiment curves (solid) of response of PlGF-2, TGF-β1, FGF-2, and IGFBP-5 to Fg β15-66. Fits of the experimental data with Langmuir binding kinetics are shown with dashed lines. Please note that the lower right panel has almost exact overlay of solid and dashed lines, with the solid line being faint.

Surface plasmon resonance (SPR) was done to quantify the affinity of specific cytokines to Fg β15-66. $K_D$ affinity values for PlGF-2, TGF-β1, FGF-2, and IGFBP-5 to Fg β15-66 were measured to be respectively 1.9 nM, 56.5 nM, 53 nM, 19.6, nM, with a lower $K_D$ corresponding to a higher affinity. Method: The methods used above were analogous to those used in Example 5. Fits of the experimental data were made with Langmuir binding kinetics. Results are depicted in FIG. 6.

Example 7

Blocking of TNC III1-5 Binding to Cytokines with Competitive Full-Length Tenascin or Heparin ELISA plates were coated with cytokines or BSA and further incubated with TNC III1-5 in the presence of a gradient of full length tenascin or heparin to verify the specificity of the binding. High concentrations of both TNC and heparin competed away binding of TNC III1-5 to the cytokines. TNC bound to the cytokines, making them unavailable for TNC III1-5, while heparin bound to TNC III1-5, blocking it to bind to the cytokines. Method: 50 nM of cytokine was coated for (1 hr, 37° C.). After blocking with 2% BSA (1 hr, RT). 10 nM TNC III1-5 was applied in PBST (0.05% tween, 0.1% bovine serum albumin (BSA)) (1 hr, RT) in the presence of a gradient of full length tenascin (0, 0.2, 0.6, 1.9, 5.6, 17, 50 nM) or heparin (0.01, 0.64, 3.2, 16, 80, 400, 2000, 10000). TNC III1-5 was detected with HRP-anti-HIS in PBST (1 hr, RT) and developed with TMB. Background values were obtained by applying each tenascin (0, 0.2, 0.6, 1.9, 5.6, 17, 50 nM) or heparin (0.01, 0.64, 3.2, 16, 80, 400, 2000, 10000) concentration to the cytokine without TNC III1-5, and were subtracted as normalization.

Figure 7:
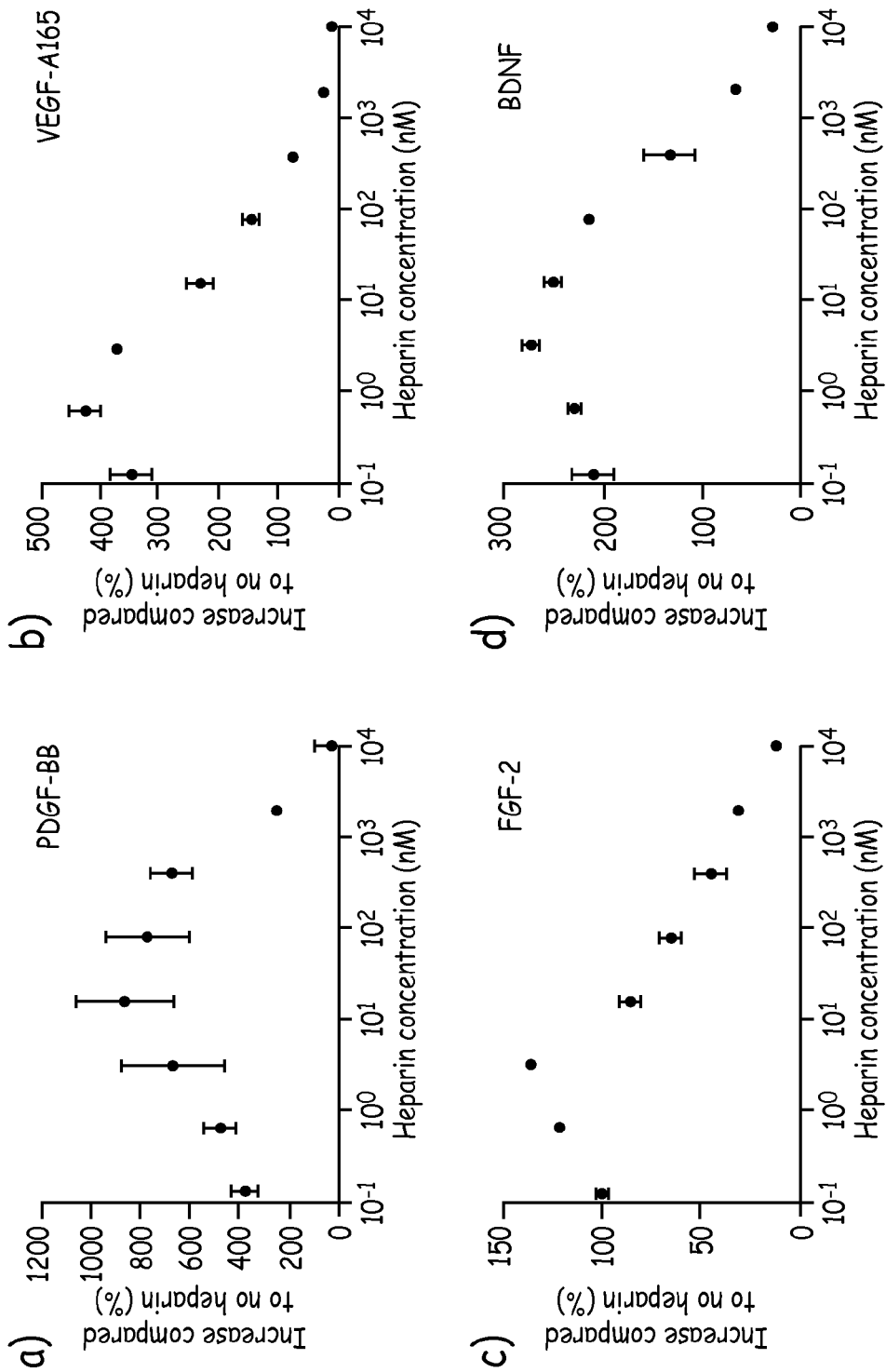
FIG. 7 has four panels that each show, in the presence of a gradient concentration of heparin, the binding of TNC III1-5 to a biomolecule as indicated: Panel a PDGF-BB; Panel b VEGF-A165, Panel c, FGF-2, Panel d and BDNF
Figure 8:
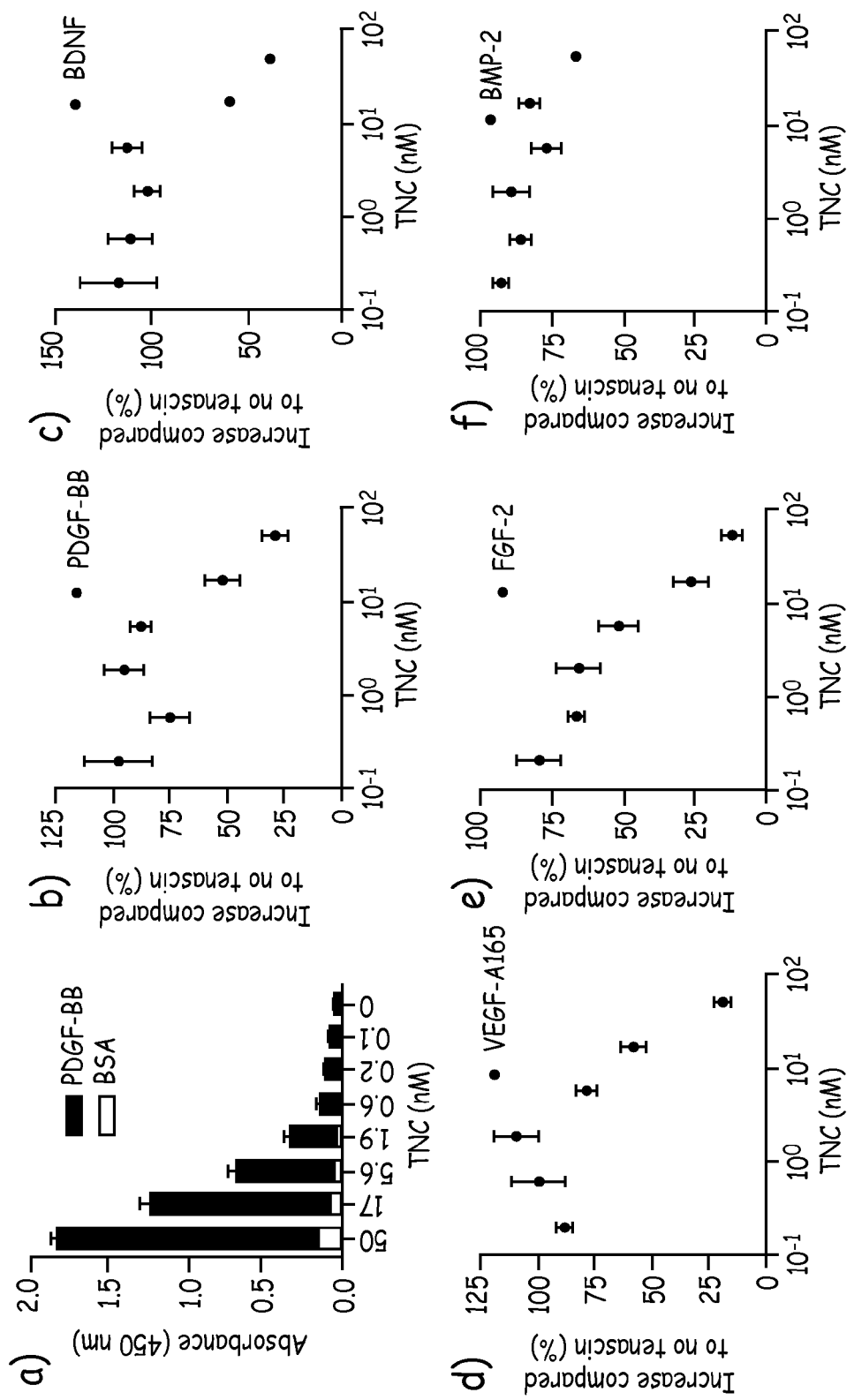
FIG. 8 shows experimental binding data as indicated in each of panels a to f: Panel a: Binding of TNC to PDGF-BB, compared to BSA; Panels b-f as follows: Competition between TNC III1-5 and TNC for: PDGF-BB (Panel b), for BDNF (Panel c), for VEGF-A165 (Panel d), FGF-2 (Panel e), and BMP-2 (Panel f), respectively.

To verify specific binding of tenascin to the cytokines, tenascin (0, 0.1, 0.2, 0.6, 1.9, 5.6, 17, 50 nM) was incubated with PDGF-BB (50 nM) and BSA and detected with mouse anti-tenascin, HRP-anti-mouse, and TMB. Results are shown in FIG. 7. FIG. 8 shows results for tests of binding of TNC to PDGF-BB, compared to BSA or competition between TNC III1-5 and TNC for PDGF-BB, BDNF, VEGF-A165, FGF-2, and BMP-2.

Example 8

Blocking of Fg β15-66 Binding to Cytokines with Competitive Heparin

ELISA plates were coated with cytokines or BSA and further incubated with Fg β15-66 in the presence of a gradient of heparin to verify the specificity of the binding. Method: Analogous to Example 7. Results shown in FIG. 9.

Example 9

Affinity of Cytokines to TNC III5

An ELISA was performed to test the affinity of different domains present in TNC1-5 to PDGF-BB as an example cytokine that has shown to bind TNC III1-5. Domain TNC III5 was defined to be responsible for cytokine binding. Method: ELISA plates were coated with individual TNC domains fused to GST, as well as GST and BSA. Wells were blocked with BSA and then incubated with 2 nM PDGF-BB. Binding of PDGF-BB was detected using an anti-PDGF-BB antibody and then a secondary horseradish peroxidase conjugated antibody. Results shown in FIG. 10.

Example 10

Production of Fusion Fragments Containing TNC and FN Fragments

TNC-FN fragment fusions were created using FN III domains to improve and extent integrin binding. These are shown below, except that a polyHistidine tag was used at the C-terminus (6 histidine residues).

Unique functional fibronectin type III repeats can be composed of various combinations of FN III and TNC III domains. They can be linked together using peptide linking sequences to generate preferred embodiments that combine the properties of each domain. Some fibronectin type III domains can also act as stabilizing elements and linking domains to create the preferred embodiments. Linking sequences between the domains can be composed of the native sequences that exist between the domains, or additional peptide sequences that allow joining of the fibronectin type III domains to generate a function multidomain protein. Here are two examples.

```
SEQ ID NO: 3: TG-FN III9-10/12/TNC III4-5, without
C-terminal His tag
NQEQVSPLAGGLDSPTGIDFSDITANSFTVHWIAPRATITGYRIRHHPEH

FSGRPREDRVPHSRNSITLTNLTPGTEYVVSIVALNGREESPPLIGQQST

VSDVPRDLEVVAATPTSLLISWDAPAVTVRYYRITYGETGGNSPVQEFTV

PGSKSTATISGLKPGVDYTITVYAVTGRGDSPASSKPISINYRTEIDSAT

AIPAPTDLKFTQVTPTSLSAQWTPPNVQLTGYRVRVTPKEKTGPMKEINL

APDSSSVVVSGLMVATKYEVSVYALKDTLTSRPAQGVVTTGLDAPRNLRR

VSQTDNSITLEWRNGKAAIDSYRIKYAPISGGDHAEVDVPKSQQATTKTT

LTGLRPGTEYGIGVSAVKEDKESNPATINAATELDTPKDLQVSETAETSL

TLLWKTPLAKFDRYRLNYSLPTGQWVGVQLPRNTTSYVLR GLEPGQEYN

VLLTAEKGRHK SKPARVKAST EQAGGGS

SEQ ID NO: 4: TG-FN III9-10/TNC III3-5, without
His tag
NQEQVSPLAGGLDSPTGIDFSDITANSFTVHWIAPRATITGYRIRHHPEH

FSGRPREDRVPHSRNSITLTNLTPGTEYVVSIVALNGREESPPLIGQQST

VSDVPRDLEVVAATPTSLLISWDAPAVTVRYYRITYGETGGNSPVQEFTV

PGSKSTATISGLKPGVDYTITVYAVTGRGDSPASSKPISINYRTTTTRLD

APSQIEVKDVTDTTALITWFKPLAEIDGIELTYGIKDVPGDRTTIDLTED

ENQYSIGNLKPDTEYEVSLISRRGDMSSNPAKETFTTGLDAPRNLRRVSQ

TDNSITLEWRNGKAAIDSYRIKYAPISGGDHAEVDVPKSQQATTKTTLTG

LRPGTEYGIGVSAVKEDKESNPATINAATELDTPKDLQVSETAETSLTLL

WKTPLAKFDRYRLNYSLPTGQWVGVQLPRNTTSYVLRGLEPGQEYNVLLT

AEKGRHKSKPARVKASTEQAGGGS

SEQ ID NO: 5: FN III9-10/TNC III1-5, without His
tag
NQEQVSPLAGGLDSPTGIDFSDITANSFTVHWIAPRATITGYRIRHHPEH

FSGRPREDRVPHSRNSITLTNLTPGTEYVVSIVALNGREESPPLIGQQST

VSDVPRDLEVVAATPTSLLISWDAPAVTVRYYRITYGETGGNSPVQEFTV

PGSKSTATISGLKPGVDYTITVYAVTGRGDSPASSKPISINYRTGGSEVS

PPKDLVVTEVTEETVNLAWDNEMRVTEYLVVYTPTHEGGLEMQFRVPGDQ

TSTIIQELEPGVEYFIRVFAILENKKSIPVSARVATYLPAPEGLKFKSIK

ETSVEVEWDPLDIALLTWEIIFRNMNKEDEGEITKSLRRPETSYRQTGLA

PGQEYEISLHIVKNNTRGPGLKRVTTTRLDAPSQIEVKDVTDTTALITWF

KPLAEIDGIELTYGIKDVPGDRTTIDLTEDENQYSIGNLKPDTEYEVSLI

SRRGDMSSNPAKETFTTGLDAPRNLRRVSQTDNSITLEWRNGKAAIDSYR
```

-continued

IKYAPISGGDHAEVDVPKSQQATTKTTLTGLRPGTEYGIGVSAVKEDKES

NPATINAATELDTPKDLQVSETAETSLTLLWKTPLAKFDRYRLNYSLPTG

QWVGVQLPRNTTSYVLRGLEPGQEYNVLLTAEKGRHKSKPARVKASTEQA

GGGS

SEQ ID NO: 6: FN III9-10/Fg β15-66, without His tag
NQEQVSPLAGGLDSPTGIDFSDITANSFTVHWIAPRATITGYRIRHHPEH

FSGRPREDRVPHSRNSITLTNLTPGTEYVVSIVALNGREESPPLIGQQST

VSDVPRDLEVVAATPTSLLISWDAPAVTVRYYRITYGETGGNSPVQEFTV

PGSKSTATISGLKPGVDYTITVYAVTGRGDSPASSKPISINYRTGHRPLD

KKREEAPSLRPAPPPISGGGYRARPAKAAATQKKVERKAPDAGGCG

SEQ ID NO: 7: FN III9-10/12-14/Fg β15-66, without His tag
NQEQVSPLAGGLDSPTGIDFSDITANSFTVHWIAPRATITGYRIRHHPEH

FSGRPREDRVPHSRNSITLTNLTPGTEYVVSIVALNGREESPPLIGQQST

VSDVPRDLEVVAATPTSLLISWDAPAVTVRYYRITYGETGGNSPVQEFTV

PGSKSTATISGLKPGVDYTITVYAVTGRGDSPASSKPISINYRTEIDSAT

AIPAPTDLKFTQVTPTSLSAQWTPPNVQLTGYRVRVTPKEKTGPMKEINL

APDSSSVVVSGLMVATKYEVSVYALKDTLTSRPAQGVVTTLENVSPPRRA

RVTDATETTITISWRTKTETITGFQVDAVPANGQTPIQRTIKPDVRSYTI

TGLQPGTDYKIYLYTLNDNARSSPVVIDASTAIDAPSNLRFLATTPNSLL

VSWQPPRARITGYIIKYEKPGSPPREVVPRPRPGVTEATITGLEPGTEYT

IYVIALKNNQKSEPLIGRKKTFKGHRPLDKKREEAPSLRPAPPPISGGGY

RARPAKAAATQKKVERKAPDAGGCG

Example 11

Molecular Fusion (Morphogen) Binding of Fusion Protein FN III9*-10,TNC III1-5

Figure 11:
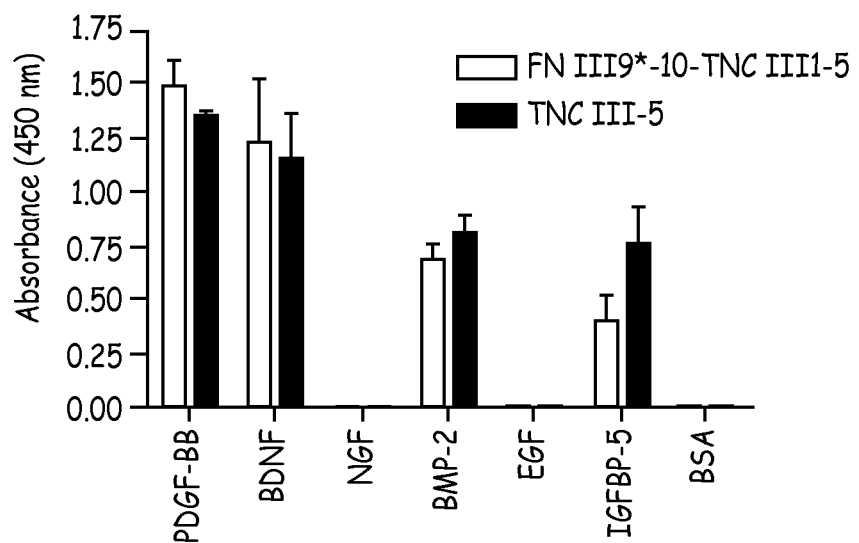
FIG. 11 is a bar graph showing the binding of FN III9*-10, TNC III1-5 to morphogens compared to TNC III1-5.

The molecular fusion protein FN III9*-10-TNC III1-5 demonstrated similar binding to select biomolecules compared to TNC III1-5. FIG. 11 shows the results. Method: The methods used above were analogous to those used in Example 3.

Example 12

Figure 12:
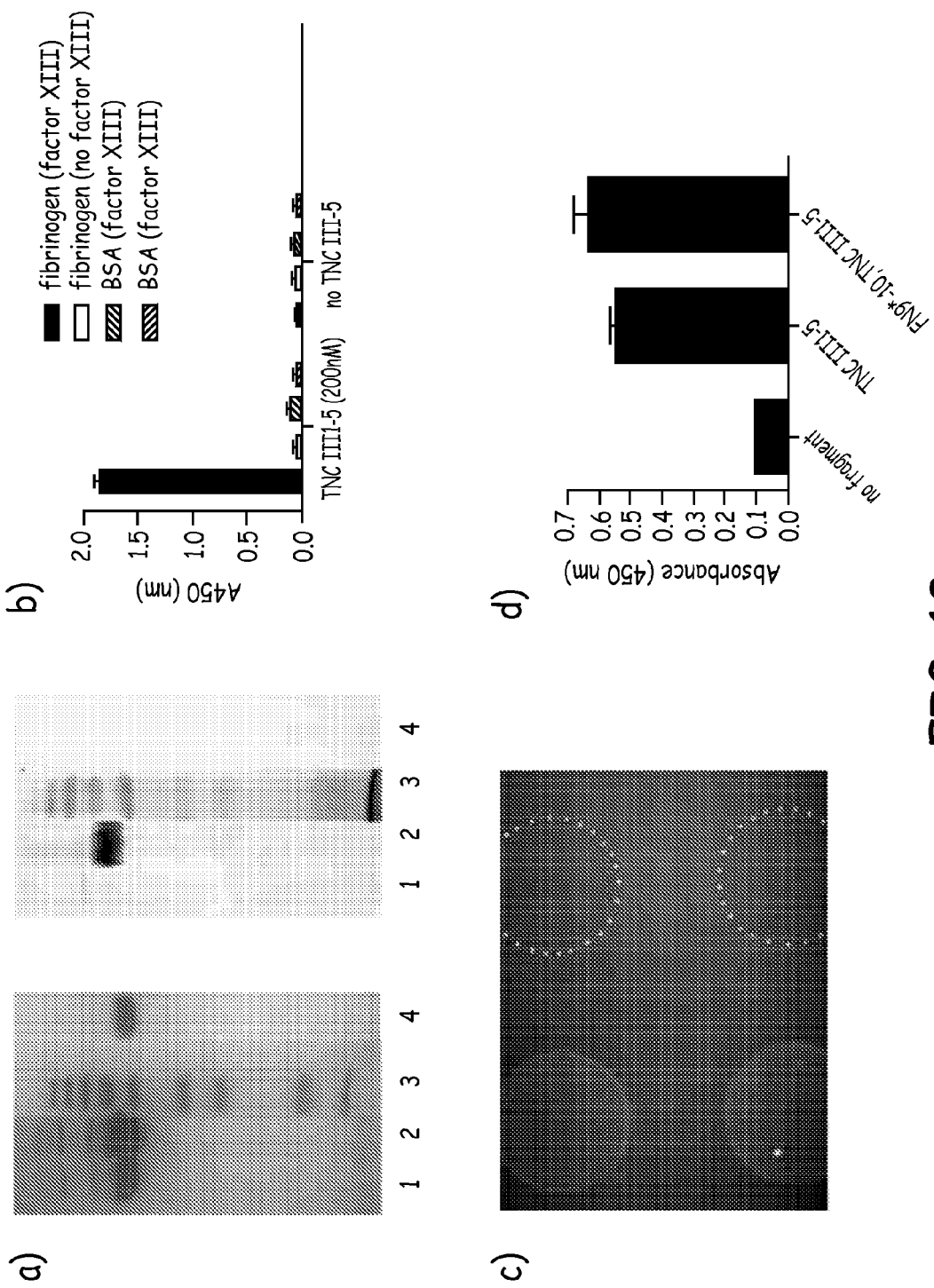
FIG. 12 is a montage of experimental results with four Panels a to d. Panel a: Binding of TG-TNC III1-5 to a fluorescent dye TAMRA (lane 1: water plus activated factor XIIIa and TAMRA, lane 2: TG-TNC III1-5 plus activated factor XIIIa and TAMRA, lane 3: ladder, lane 4: TG-TNC III1-5 and TAMRA), Panel b: Binding of TG-TNC III1-5 to fibrinogen coated surfaces. Panel c: Binding of TG-TNC III1-5 to a PEG-lysine gel (left spots (450 μm): TG-TN III1-5, right spots, marked by white dotted line: water). Panel d: Binding of TG-TNC III1-5 and TG-FN III9*-10, TNC III1-5 into 3 dimensional 2% TG-PEG gels.

Binding of TG-TNC III1-5 and TG-FN III9*-10, TNC III1-5 to Biomaterials, Such as Fibrinogen and PEG Gels, by Transglutaminase Reaction The activity of the transglutaminase substrate (TG: NQEQVSPL) (SEQ ID NO:10) of the engineered protein TG-TNC III1-5 was confirmed. FIG. 12 depicts results. Methods: A) The TG activity of TG-TNC III1-5 was tested by reaction with a fluorescent TAMRA molecule, containing lysines, with and without the presence of factor XIIIa, the TAMRA molecule, or TG-TNC III1-5. Binding of TNC III1-5 to the fluorescent molecule TAMRA, only in the presence of factor XIIIa, demonstrates specific covalent binding due to the TG substrate. B) The TG activity of TG-TNC III1-5 was tested by reaction with fibrinogen, with and without the presence of factor XIIIa, fibrinogen, or TG-TNC III1-5. Fibrinogen or no protein was coated on an ELISA plate (1 hr, 37° C.), blocked with 2% BSA (1 hr, RT), reacted with or without TG-TNC III1-5 or factor XIIIa C) The TG activity of TG-TNC III1-5 was tested by reaction with PEG-lysines. A robotic spotter was used to bind TG-TNC III1-5 inside 450 μm spots (Gobaa, Hoehnel, et al., 2011), and an immuno-fluorescent stain was used to visualize the location and distribution of TG-TNC III1-5 onto the PEG. D) TG-TNC III1-5 and TG-FN III9*-10,TNC III1-5 (5 μM) were incorporated into a 2% TG-PEG gel. After 2 washed with PBS, 98% and 96% respectively of the fragments was bound into gels, which were sequentially stained with HRP-conjugated anti-HIS, and developed with TMB to read an absorbance at 450 nm.

Example 13

Cytokine Retention in 3 Dimensional PEG Gels Modified with TG-Fg β15-66

Cytokines that demonstrated binding to Fg β15-66 were retained into PEG gels modified with TG-Fg β15-66. Method: TG-PEG gels (1.5%) were fabricated with a TG-RDG integrin binding peptide and with and without TG-Fg β15-66. Different cytokines were mixed within the gels: PlGF-1 that did not bind Fg β15-66 and FGF-2 and PlGF-2 that did bind Fg β15-66. A release study was performed over 7 days, with the release buffer being replaced each day. At day 8, fractions of cytokines remaining in the matrices were quantified, after having digested the matrix by plasmin.

Example 14

Bioactivity Assay of TNC III1-5: Proliferation and Phosphorylation Properties of Cytokines with and without TNC III1-5

Figure 14:
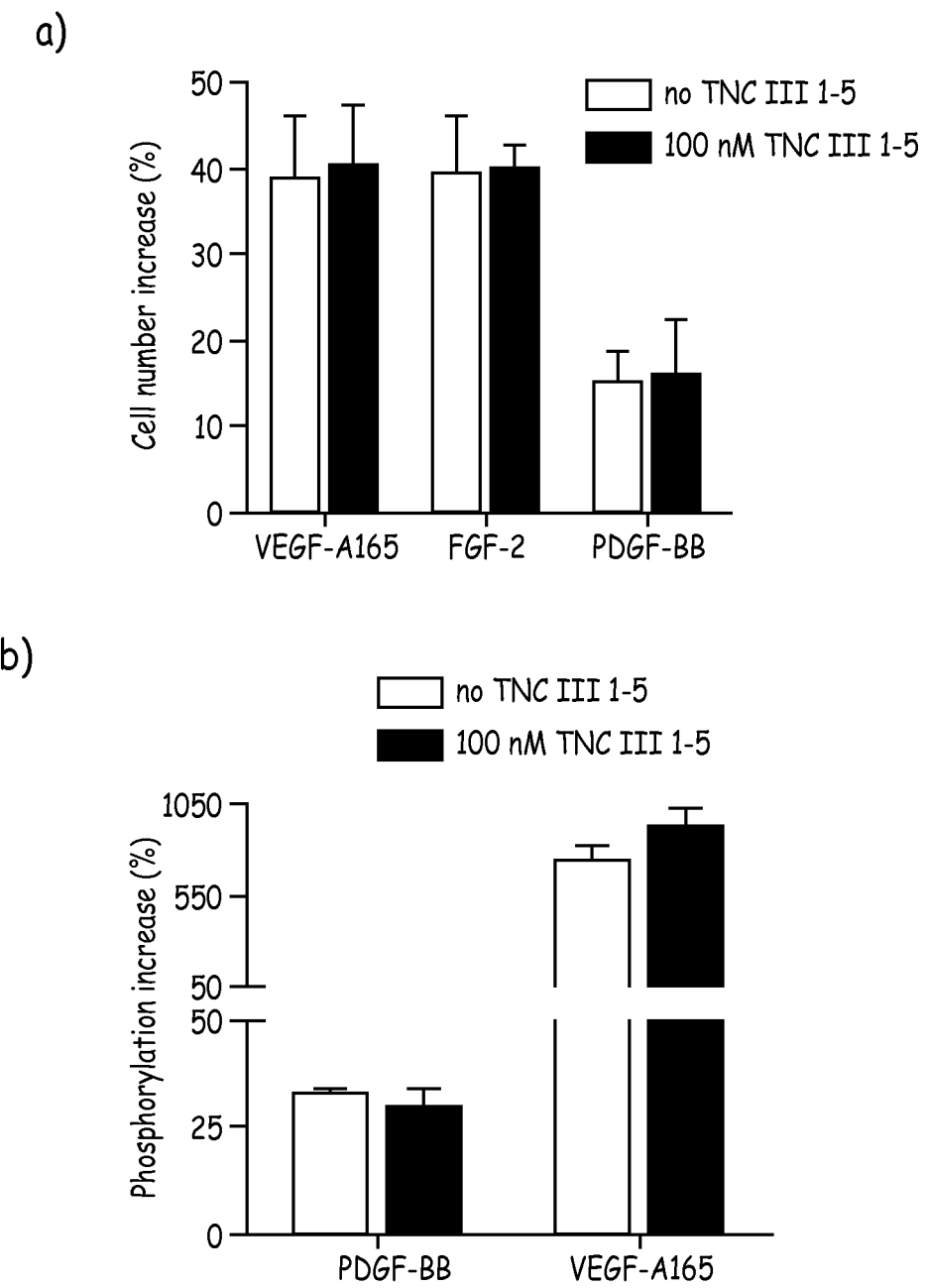
FIG. 14 has two panels of experimental data. Panel a. Proliferation assay of HUVEC and SMC cells with VEGF- A165 and PDGF-BB respectively, with and without the presence of TNC III1-5. Panel b. Phosphorylation assay of HUVEC and SMC cells with VEGF-A165 and PDGF-BB respectively, with and without the presence of TNC III1-5.

To verify that cytokines bound to TNC III1-5 are still bioactive, the proliferation and phosphorylation of a variety of different cell types was tested: smooth muscle cells and endothelial cell. FIG. 14 depicts results.
Methods
Proliferation Assay:
a. HUVECs: serum starved human umbilical vein endothelial cells (HUVECs), in Endothelial
Basal Medium MCDB-131 with 1% FBS, were plated in 96-well cell culture plate (5000 cells/well) with VEGF-A165 (5 ng/mL), with or without 100 nM TNC III1-5. After 72 hrs, the cell number was quantified using almarBlue (AbD Serotec), and the percent proliferation was calculated over the condition without cytokines or TNC III1-5.
b. SMCs: serum starved human smooth muscle cells (SMCs), in DMEM with 1% FBS, were plated in 96-well cell culture plates (2,500 cells/well) with PDGF-BB (5 ng/mL) or FGF-2 (5 ng/mL), with or without 100 nM TNC III1-5. After 72 hrs, the cell number was quantified using CyQUANT, and the percent proliferation was calculated over the condition without cytokines or TNC III1-5.
B) Phosphorylation Assay:
a. HUVECs: 6 well plates were pre-coated with 50 μg/mL type-I collagen (1 hr, 37° C.). HUVEC cells (600,000 cells/well) were seeded and cultured for 24 hours in Endothelial cell growth medium and starved for 24 hours in MCDB-131 with 0.5% FBS. VEGF-A165 (5 ng/mL)

was added to MCDB 131 media containing 1% FBS and 0.1% BSA and incubated with or without 100 nM TNC III1-5 for 15 minutes.

b. SMCs: SMC (360,000 cells/well) were seeded and cultured in DMEM containing 10% FBS, and starved for 24 hours in DMEM containing 0.5% FBS. PDGF-BB (5 ng/mL) was added to DMEM media without FBS and 0.1% BSA and incubated with or without 100 nM TNC III1-5 for 15 minutes.

After starvation, the cells were washed with 1× PBS, and the different media samples were added to the cells for 5 minutes at 37° C. As a control, media was added without cytokines, but also with or without TNC III1-5 (100 nM). After 5 minutes incubation, the cells were lysed in 500 βL lysis buffer per well for 30 min at 4° C., and the lysate frozen in low binding Eppendorf tubes. The amount of tyrosine-phosphorylated VEGF receptor 2 (phospho-VEGF R2) and PDGF receptor β (phospho-PDGF R β) in the lysate was measured using a sandwich ELISA (Human Phospho-VEGF R2/KDR and Phospho-PDGF Rbeta DuoSet IC, R&D, Minneapolis, Minn.), and normalized to the total protein content in the lysate, which was obtained by a bicinchoninic acid (BCA) protein assay (Thermo Fisher Scientific, Rockford, Ill.).

Example 15

Bioactivity Assay of Fg β15-66: Proliferation and Phosphorylation Properties of Cytokines with and without Fg β15-66

Figure 15:
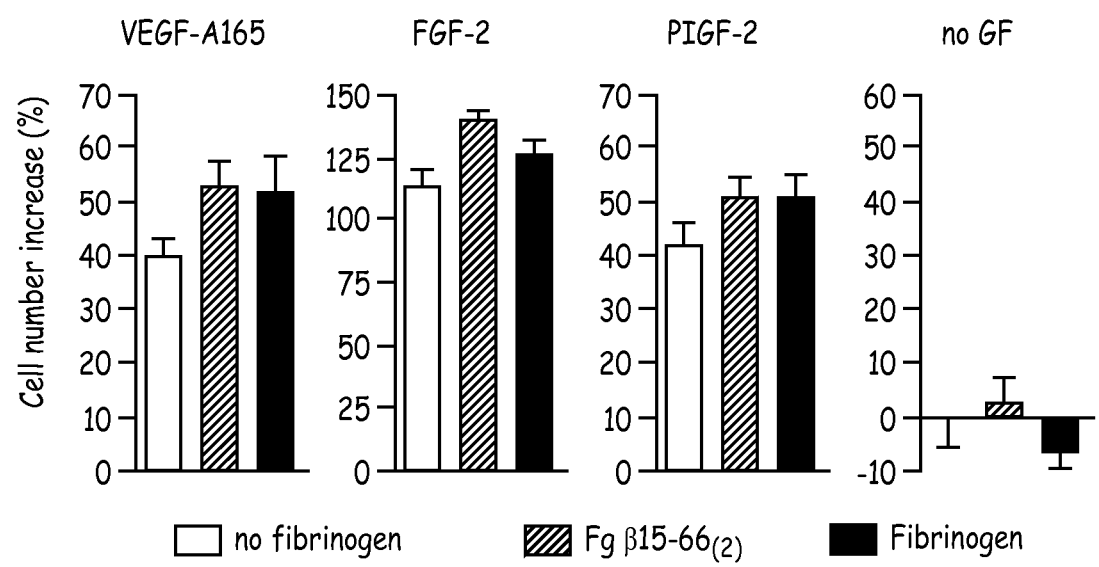
FIG. 15 is a bar graph of experimental data that shows a proliferation increase of HUVEC after 72 hours over baseline (proliferation without cytokine and Fg β15-66). Cytokines significantly increased cell proliferation, but no synergistic effect were found between cells treated with cytokines alone and cells treated with cytokines plus fibrinogen or Fg β15-66.

To verify that cytokines bound to Fg β15-66 are still bioactive, the proliferation of HUVEC cells was tested for different cytokines with and without the presence of Fg β15-66. Results are shown in FIG. 15. Method: HUVEC cells were stimulated with various cytokines: VEGF-A165, PlGF-2, and FGF-2 with or without fibrinogen or Fg β15-66 in excess (≥100-fold molar excess).

Example 16

Neurite Extension on/in PEG Gels Modified with TNC III1-5 or Fusion Proteins Containing TNC III5 and Fibronectin Domains The ability of TNC III1-5 or fusion proteins containing fibronectin domains to promote neurite extension was tested by linking these fragments to a PEG gel. Method 1: TNC fragments are bound to 2 dimensional PEG gels containing a lysine using a robotic spotter. The different fragments are deposited in the presence of factor XIIIa onto 450 µm spots, while neurons are seeded on the entire gel. Neurons were dissociated from dorsal root ganglions (DRGs) from day 8-10 embryonic chickens. The media contained 10 ng/mL NT-3 or BDNF and 10% FBS. Neurites are stained with a neuronal class III®-tubulin (TUJ1) monoclonal antibody plus goat rhodamine (TRITC) anti-mouse. Neurite extension is quantified in Image J or Neuron J. Results in FIGS. 16 and 17.

Example 17

Smooth Muscle Cell Proliferation on PEG Gels Modified with TNC III1-5 or Fusion Proteins Containing TNC III5 and Fibronectin Domains TG-PEG gels (2%), modified with TNC III1-5 and FN III9*-10, TNC III1-5 enhanced SMC proliferation in the presence of PDGF-BB. Results are detailed in FIGS. 18 and 19.

Method: Three different gels were fabricated, unmodified PEG, and PEG gels modified with TNC III1-5 or FN III9*-10,TNC III1-5 (5 µM). Unbound fragment was washed from the gels. Sequentially, gels were incubated for 1 hour at 37° C. with 100 µL DMEM without PDGF-BB or with PDGF-BB (1 ng per gel). For one set of gels, the media containing PDGF-BB was removed and gels were washed for 1 hour at RT. Cells were added to each gel and a proliferation assay with Alamar Blue was performed at 72 hours.

Example 18

Treatment of Skin Wounds

Figure 20:
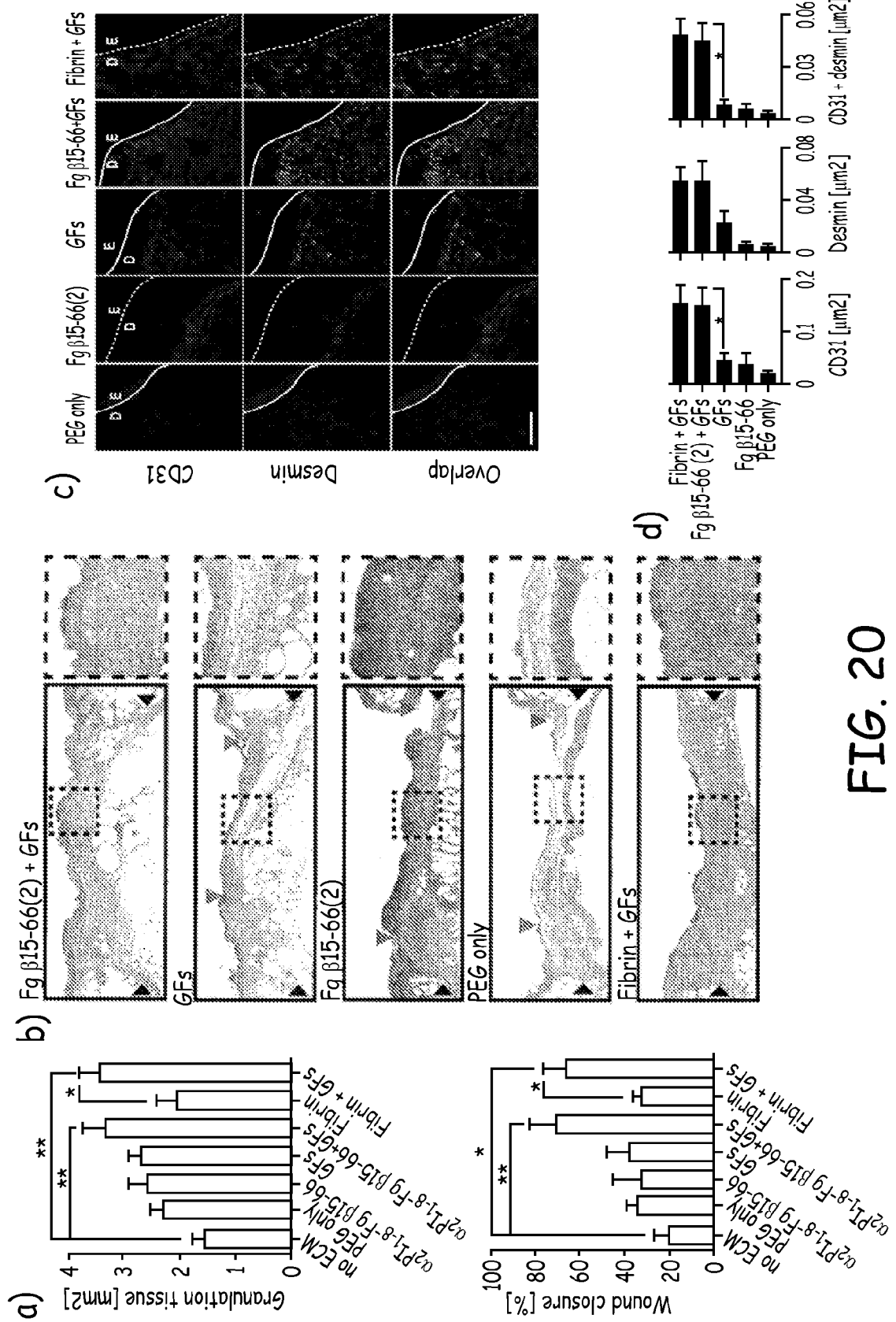
FIG. 20 is a montage of experimental results having panels a through d. Panel a: Wound closure and granulation tissue area at 10 days (n=8 per matrix). For statistical comparisons ANOVA with Tukey's test was used; *$p<0.05$, **$p<0.01$. Panel b: Representative histology (hematoxylin and eosin staining). Black arrows indicate wound edges; light arrows indicate tips of epithelium tongue. The granulation tissue is characterized by a large number of cells (granulocytes) with nuclei that stain darkly. Muscle under the wounds is stained. Fat tissue appears as transparent bubbles. Scale bar=1 mm. Higher magnification (5×) of the granulation tissue is shown on the right. Panel c: Angiogenesis within the granulation tissue was assessed with a staining for endothelial ($CD31^+$ cells) and smooth muscle cells ($desmin^+$ cells) in the wound tissue. Representative images are shown: E, epidermis; D, dermis; hashed line, basement membrane. Scale bar=0.2 mm. Panel d: The graphs show quantification of stained area for CD31 and desmin as well as the overlay (mean±SEM; n=5). *$p<0.05$, Student's t test.

Delivering cytokines within the TG-PEG gels functionalized with a molecule fusion protein of TG-Fg β15-66 enhanced skin-wound healing in diabetic mice. Method: Full-thickness back-skin wounds were treated with combined FGF-2 and PlGF-2. Seven groups were tested: treatment (no ECM); fibrin only; fibrin containing cytokines; PEG only, PEG containing cytokines; PEG functionalized with TG-Fg β15-66, and PEG functionalized with TG-Fg β15-66 containing cytokines. After 10 days, wound closure and granulation tissue area were evaluated by histology. FIG. 20 details the results.

Example 19

Treatment of Bone Lesions

Functionalized matrices with above mentioned TNC, FN, fibrinogen fragments could be useful in engineering a microenvironment for bone healing. Since, the cytokines BMP-2 and PDGF-BB are beneficial for bone repair (Hollinger, Hart, et al., 2008), TNC-functionalized matrices containing a low dose of combined BMP-2 (100 ng) and PDGF-BB (100 ng), could enhance bone repair. A relevant model to illustrate human translational potential is the critical-size calvarial defect in a skeletally mature rat, which is a standard and clinically relevant model for nonunion bone healing (Muschler, Raut, et al.; Hollinger and Kleinschmidt, 1990). Preclinical evaluations of bone repair materials and osteoinductive proteins commonly include critical-size bone defect models, such as the critical-size calvarial defect in the rat (Hollinger and Kleinschmidt, 1990). Defects measuring 6 mm each would be treated. After 4 weeks, bone healing—characterized by bone tissue deposition and coverage of the defects—would be analyzed using microcomputed tomography (microCT) and histology. The delivery of cytokines alone in matrix would not increase bone healing, when compared to the lesions treated with matrix only as a control. For comparison, while 1 µg is usually insufficient to treat calvarial defect of 6 mm in the rat (Schmoekel, Weber, et al., 2005), and milligram-quantities of BMP-2 are needed to treat tibial fractures in humans (Gautschi, Frey, et al., 2007). In contrast, cytokines delivered within the TNC fragment-functionalized matrix would led to a marked increase of bone tissue deposition, and a faster closure of the defect. Moreover, the amount of MSC recruited in the TNC-fragment matrices would be higher than in matrices containing only cytokines.

Example 20

Treatment of Nerve Lesions

Functionalized matrices with above mentioned TNC, FN, fibrinogen fragments could be useful in engineering a microenvironment for nerve regeneration. Both NT-3 and BDNF have shown to bind TNC III5, and play an important role to regenerate motor neuronal tracts after spinal cord injury (Jones, Oudega, et al., 2001). The integrin binding domains present in FN III9*-10 and TNC III3 can enhance integrin signaling and promote neurite extension (Andrews, Czvitkovich, et al., 2009). Both fibrin and TG-PEG gels, modified with fragments containing TNC, FN, and fibrinogen domains, can be injected after spinal cord injury and provide a supportive environment for nerve regeneration. A contusion mouse model can be used to analyze neurite extension into the gel after injury (Tysseling-Mattiace, Sahni, et al., 2008). In addition, the engineering of biomaterial matrices with fragments containing TNC, FN, and fibrinogen domains, in combination with specific cytokines may function as a support for cell transplantations to enhance survival and control migration of these transplanted cells (Sharp, Frame, et al., 2010), rendering cell-based therapies after nerve injury in more successful therapies by combining them with drug and material based therapies.

Example 21

Discovery of Antibodies to TNC III5

The finding of the cytokine-binding domain of TNC, TNC III5, allows clinicians to immunize mice with this fragment or parts of TNC III1-5 to obtain specific monoclonal antibodies against this domain or nearby domains. Alternatively, peptide libraries can be used to find a sequence that binds TNC III1-5 or TNC III5. The complementarity determining regions (CDR) of the discovered monoclonal antibody are then affinity matured using scFV display techniques.

Example 22

Antibody Discovery to Block Cytokine Binding to TNC III5

An antibody against TNC III5 may be produced in an attempt to block morphogen binding to this domain.

Method: A protein fragment, containing domain TNC III5, will be injected into mice to create antibodies against this domain. To ensure the proper folding of the domain, TNC III5 will be flanked by its natural neighboring domains and with a potential extra GST domain in front of the fragment: for example GST-TNC III4-5-A1 (see Example 1). It is then routine to screen the produced antibody titers to select the antibody that binds TNC III5 separately and full length TNC.

References:

1 Schonherr E & Hausser H J (2000) "Extracellular matrix and cytokines: a functional unit." Developmental immunology 7 (2-4): 89-101.

2 Martino M M & Hubbell J A (2010) "The 12th-14th type III repeats of fibronectin function as a highly promiscuous growth factor-binding domain." The FASEB journal: official publication of the Federation of American Societies for Experimental Biology 24(12):4711-4721.

3 Martino M M, Tortelli F, Mochizuki M, Traub S, Ben-David D, Kuhn G A, Muller R, Livne E, Eming S A, & Hubbell J A (2011) "Engineering the growth factor microenvironment with fibronectin domains to promote wound and bone tissue healing." Science translational medicine 3(100):100ra189.

4 Kleinman H K, Philp D, & Hoffman M P (2003) "Role of the extracellular matrix in morphogenesis." Curr Opin Biotechnol 14(5):526-532.

5 Discher D E, Mooney D J, & Zandstra P W (2009) "Growth factors, matrices and forces combine and control stem cells." Science 324:1673-1677.

6 Berrier A L & Yamada K M (2007) "Cell-matrix adhesion." J Cell Physiol 213:565-573.

7 Hinz B (2009) "The myofibroblast: paradigm for a mechanically active cell." J Biomech:doi:10.1016/j.jbiomech.2009.1009.1020.

8 Schultz G S & Wysocki A (2009) "Interactions between extracellular matrix and growth factors in wound healing." Wound Repair Regen 17:153-162.

9 Lindahl U & Li J P (2009) "Interactions between heparan sulfate and proteins—design and functional implications." Int Rev Cell Molec Biol 276:105-159.

10 Makarenkova H P, Hoffman M P, Beenken A, Eliseenkova A V, Meech R, Tasau C, Patel V N, Lang R A, & Mohammadi M (2009) "Differential interactions of FGFs with heparan sulfate control gradient formation and branching morphogenesis." Sci Signal 2:ra55.

11 Trebaul A, Chan E K, & Midwood K S (2007) "Regulation of fibroblast migration by tenascin-C." Biochem Soc Trans 35(Pt 4):695-697.

12 Orend G (2005) "Potential oncogenic action of tenascin-C in tumorigenesis." Int J Biochem Cell Biol 37(5): 1066-1083.

13 Udalova I A, Ruhmann M, Thomson S J, & Midwood K S (2011) "Expression and immune function of tenascin-C." Crit Rev Immunol 31(2):115-145.

14 Jones F S & Jones P L (2000) "The tenascin family of ECM glycoproteins: structure, function, and regulation during embryonic development and tissue remodeling." Dev Dyn 218(2):235-259.

15 Joester A & Faissner A (2001) "The structure and function of tenascins in the nervous system." Matrix Biol 20(1):13-22.

16 Imanaka-Yoshida K, Matsuura R, Isaka N, Nakano T, Sakakura T, & Yoshida T (2001) "Serial extracellular matrix changes in neointimal lesions of human coronary artery after percutaneous transluminal coronary angioplasty: clinical significance of early tenascin-C expression." Virchows Arch 439(2):185-190.

17 Golledge J, Clancy P, Maguire J, Lincz L, & Koblar S (2011) "The role of tenascin C in cardiovascular disease." Cardiovasc Res 92(1):19-28.

18 O'Connell J T, Sugimoto H, Cooke V G, Macdonald B A, Mehta A I, Lebleu V S, Dewar R, Rocha R M, Brentani R R, Resnick M B, Neilson E G, Zeisberg M, & Kalluri R (2011) "VEGF-A and Tenascin-C produced by S100A4+ stromal cells are important for metastatic colonization." Proc Natl Acad Sci USA 108(38):16002-16007.

19 Oskarsson T, Acharyya S, Zhang X H, Vanharanta S, Tavazoie S F, Morris P G, Downey R J, Manova-Todorova K, Brogi E, & Massague J (2011) "Breast cancer cells produce tenascin C as a metastatic niche component to colonize the lungs." Nat Med 17(7):867-874.

20 Midwood K S, Hussenet T, Langlois B, & Orend G (2011) "Advances in tenascin-C biology." Cell Mol Life Sci 68(19):3175-3199.

21 Weisel J W (2007) "Structure of fibrin: impact on clot stability." Journal of thrombosis and haemostasis: JTH 5 Suppl 1:116-124.

22 Mosesson M W (2005) "Fibrinogen and fibrin structure and functions." Journal of thrombosis and haemostasis: JTH 3(8):1894-1904.
23 Hantgan R R, Francis C W, & Marder V J (1994) Chapter 14: Fibrinogen structure and physiology (Lippincott Company, Philadelphia) 3rd Ed.
24 Ugarova T P & Yakubenko V P (2001) "Recognition of fibrinogen by leukocyte integrins." Annals of the New York Academy of Sciences 936:368-385.
25 Flick M J, Du X, Witte D P, Jirouskova M, Soloviev D A, Busuttil S J, Plow E F, & Degen J L (2004) "Leukocyte engagement of fibrin(ogen) via the integrin receptor alphaMbeta2/Mac-1 is critical for host inflammatory response in vivo." The Journal of clinical investigation 113(11):1596-1606.
26 Janmey P A, Winer J P, & Weisel J W (2009) "Fibrin gels and their clinical and bioengineering applications." Journal of the Royal Society, Interface/the Royal Society 6(30):1-10.
27 Lorand L & Graham R M (2003) "Transglutaminases: crosslinking enzymes with pleiotropic functions." Nature reviews. Molecular cell biology 4(2):140-156.
28 Standeven K F, Carter A M, Grant P J, Weisel J W, Chernysh I, Masova L, Lord S T, & Ariens R A (2007) "Functional analysis of fibrin {gamma}-chain cross-linking by activated factor XIII: determination of a cross-linking pattern that maximizes clot stiffness." Blood 110(3):902-907.
29 Weisel J W (2004) "The mechanical properties of fibrin for basic scientists and clinicians." Biophys Chem 112(2-3):267-276.
30 Schense J C & Hubbell J A (1999) "Cross-linking exogenous bifunctional peptides into fibrin gels with factor XIIIa." Bioconjug Chem 10(1):75-81.
31 Patterson J, Martino M M, & Hubbell J A (2010) "Biomimetic materials in tissue engineering." Materials Today 13(1-2):14-22.
32 Sahni A, Khorana A A, Baggs R B, Peng H, & Francis C W (2006) "FGF-2 binding to fibrin(ogen) is required for augmented angiogenesis." Blood 107(1):126-131.
33 Peng H, Sahni A, Fay P, Bellum S, Prudovsky I, Maciag T, & Francis C W (2004) "Identification of a binding site on human FGF-2 for fibrinogen." Blood 103(6):2114-2120.
34 Werner S & Grose R (2003) "Regulation of wound healing by growth factors and cytokines." Physiological reviews 83(3):835-870.
35 Sahni A, Odrljin T, & Francis C W (1998) "Binding of basic fibroblast growth factor to fibrinogen and fibrin." Journal of Biological Chemistry 273(13):7554-7559.
36 Krammer A, Craig D, Thomas W E, Schulten K, & Vogel V (2002) "A structural model for force regulated integrin binding to fibronectin's RGD-synergy site." Matrix Biol 21(2):139-147.
37 Mao Y & Schwarzbauer J E (2005) "Fibronectin fibrillogenesis, a cell-mediated matrix assembly process." Matrix Biol 24(6):389-399.
38 Pankov R & Yamada K M (2002) "Fibronectin at a glance." J Cell Sci 115(Pt 20):3861-3863.
39 Upton Z, Webb H, Hale K, Yandell C A, McMurtry J P, Francis G L, & Ballard F J (1999) "Identification of vitronectin as a novel insulin-like growth factor-II binding protein." Endocrinology 140(6):2928-2931.
40 Kricker J A, Towne C L, Firth S M, Herington A C, & Upton Z (2003) "Structural and functional evidence for the interaction of insulin-like growth factors (IGFs) and IGF binding proteins with vitronectin." Endocrinology 144(7):2807-2815.
41 Schoppet M, Chavakis T, Al-Fakhri N, Kanse S M, & Preissner K T (2002) "Molecular interactions and functional interference between vitronectin and transforming growth factor-beta." Lab Invest 82(1):37-46.
42 Leahy D J, Hendrickson W A, Aukhil I, & Erickson H P (1992) "Structure of a fibronectin type III domain from tenascin phased by MAD analysis of the selenomethionyl protein." Science 258(5084):987-991.
43 Peng Q, Zhuang S, Wang M, Cao Y, Khor Y, & Li H (2009) "Mechanical design of the third FnIII domain of tenascin-C." Journal of molecular biology 386(5):1327-1342.
44 Yokosaki Y, Matsuura N, Higashiyama S, Murakami I, Obara M, Yamakido M, Shigeto N, Chen J, & Sheppard D (1998) "Identification of the ligand binding site for the integrin alpha9 beta1 in the third fibronectin type III repeat of tenascin-C." The Journal of biological chemistry 273(19):11423-11428.
45 Weber P, Zimmermann D R, Winterhalter K H, & Vaughan L (1995) "Tenascin-C binds heparin by its fibronectin type III domain five." J Biol Chem 270(9): 4619-4623.
46 Weisel J W, Stauffacher C V, Bullitt E, & Cohen C (1985) "A model for fibrinogen: domains and sequence." Science 230(4732): 1388-1391.
47 Odrljin T M, Shainoff J R, Lawrence S O, & Simpson-Haidaris P J (1996) "Thrombin cleavage enhances exposure of a heparin binding domain in the N-terminus of the fibrin beta chain." Blood 88(6):2050-2061.
48 Mardon H J & Grant K E (1994) "The role of the ninth and tenth type III domains of human fibronectin in cell adhesion." FEBS Lett 340(3):197-201.
49 Mould A P, Askari J A, Aota S, Yamada K M, Irie A, Takada Y, Mardon H J, & Humphries M J (1997) "Defining the topology of integrin alpha5beta1-fibronectin interactions using inhibitory anti-alpha5 and anti-beta1 monoclonal antibodies. Evidence that the synergy sequence of fibronectin is recognized by the amino-terminal repeats of the alpha5 subunit." J Biol Chem 272(28): 17283-17292.
50 Danen E H, Aota S, van Kraats A A, Yamada K M, Ruiter D J, & van Muijen G N (1995) "Requirement for the synergy site for cell adhesion to fibronectin depends on the activation state of integrin alpha 5 beta 1." J Biol Chem 270(37):21612-21618.
51 van der Walle C F, Altroff H, & Mardon H J (2002) "Novel mutant human fibronectin FIII9-10 domain pair with increased conformational stability and biological activity." Protein engineering 15 (12): 1021-1024.
52 Gurtner G C, Werner S, Barrandon Y, & Longaker M T (2008) "Wound repair and regeneration." Nature 453 (7193):314-321.
53 Herbert S P & Stainier D Y (2011) "Molecular control of endothelial cell behaviour during blood vessel morphogenesis." Nature reviews. Molecular cell biology 12(9): 551-564.
54 Karp J M & Leng Teo G S (2009) "Mesenchymal stem cell homing: the devil is in the details." Cell Stem Cell 4(3):206-216.
55 Eming S A, Hammerschmidt M, Krieg T, & Roers A (2009) "Interrelation of immunity and tissue repair or regeneration." Seminars in cell & developmental biology 20(5):517-527.

56 Lutolf M P & Hubbell J A (2005) "Synthetic biomaterials as instructive extracellular microenvironments for morphogenesis in tissue engineering." Nat Biotechnol 23(1):47-55.

57 Atala A (2008) "Advances in tissue and organ replacement." Curr Stem Cell Res Ther 3(1):21-31.

58 Huebsch N & Mooney D J (2009) "Inspiration and application in the evolution of biomaterials." Nature 462(7272):426-432.

59 Affolter M & Basler K (2007) "The Decapentaplegic morphogen gradient: from pattern formation to growth regulation." Nature reviews. Genetics 8(9):663-674.

60 Vilcek J & Feldmann M (2004) "Historical review: Cytokines as therapeutics and targets of therapeutics." Trends in pharmacological sciences 25(4):201-209.

61 Cross M & Dexter T M (1991) "Growth factors in development, transformation, and tumorigenesis." Cell 64(2):271-280.

62 Oviedo N J & Beane W S (2009) "Regeneration: The origin of cancer or a possible cure?" Seminars in cell & developmental biology 20(5):557-564.

63 Schafer M & Werner S (2008) "Cancer as an overhealing wound: an old hypothesis revisited." Nature reviews. Molecular cell biology 9(8):628-638.

64 Wrzesinski S H, Wan Y Y, & Flavell R A (2007) "Transforming growth factor-beta and the immune response: implications for anticancer therapy." Clinical cancer research: an official journal of the American Association for Cancer Research 13(18 Pt 1):5262-5270.

65 Bierie B & Moses H L (2010) "Transforming growth factor beta (TGF-beta) and inflammation in cancer." Cytokine & growth factor reviews 21(1):49-59.

66 Untergasser G, Gander R, Lilg C, Lepperdinger G, Plas E, & Berger P (2005) "Profiling molecular targets of TGF-beta1 in prostate fibroblast-to-myofibroblast transdifferentiation." Mechanisms of ageing and development 126(1):59-69.

67 Wesche J, Haglund K, & Haugsten E M (2011) "Fibroblast growth factors and their receptors in cancer." The Biochemical journal 437(2):199-213.

68 Lohela M, Bry M, Tammela T, & Alitalo K (2009) "VEGFs and receptors involved in angiogenesis versus lymphangiogenesis." Current opinion in cell biology 21(2):154-165.

69 Issa A, Le T X, Shoushtari A N, Shields J D, & Swartz M A (2009) "Vascular endothelial growth factor-C and C-C chemokine receptor 7 in tumor cell-lymphatic crosstalk promote invasive phenotype." Cancer research 69(1):349-357.

70 Wang Z, Ahmad A, Li Y, Kong D, Azmi A S, Banerjee S, & Sarkar F H (2010) "Emerging roles of PDGF-D signaling pathway in tumor development and progression." Biochimica et biophysica acta 1806(1):122-130.

71 Lam C T, Yang Z F, Lau C K, Tam K H, Fan S T, & Poon R T (2011) "Brain-derived neurotrophic factor promotes tumorigenesis via induction of neovascularization: implication in hepatocellular carcinoma." Clinical cancer research: an official journal of the American Association for Cancer Research 17(10):3123-3133.

72 Kramer F, Stover T, Warnecke A, Diensthuber M, Lenarz T, & Wissel K (2010) "BDNF mRNA expression is significantly upregulated in vestibular schwannomas and correlates with proliferative activity." Journal of neuro-oncology 98(1):31-39.

73 Lutolf M P, Lauer-Fields J L, Schmoekel H G, Metters A T, Weber F E, Fields G B, & Hubbell J A (2003) "Synthetic matrix metalloproteinase-sensitive hydrogels for the conduction of tissue regeneration: engineering cell-invasion characteristics." Proc Natl Acad Sci USA 100(9):5413-5418.

74 Ehrbar M, Rizzi S C, Hlushchuk R, Djonov V, Zisch A H, Hubbell J A, Weber F E, & Lutolf M P (2007) "Enzymatic formation of modular cell-instructive fibrin analogs for tissue engineering." Biomaterials 28(26):3856-3866.

75 Mosesson M W (2005) "Fibrinogen and fibrin structure and functions." Journal of Thrombosis and Haemostasis 3(8):1894-1904.

76 Martino M M, Mochizuki M, Rothenfluh D A, Rempel S A, Hubbell J A, & Barker T H (2009) "Controlling integrin specificity and stem cell differentiation in 2D and 3D environments through regulation of fibronectin domain stability." Biomaterials 30(6):1089-1097.

77 Ehrbar M, Rizzi S C, Schoenmakers R G, Miguel B S, Hubbell J A, Weber F E, & Lutolf M P (2007) "Biomolecular hydrogels formed and degraded via site-specific enzymatic reactions." Biomacromolecules 8(10):3000-3007.

78 Gobaa S, Hoehnel S, Roccio M, Negro A, Kobel S, & Lutolf M P (2011) "Artificial niche microarrays for probing single stem cell fate in high throughput." Nat Methods.

79 Hanft J R, Pollak R A, Barbul A, van Gils C, Kwon P S, Gray S M, Lynch C J, Semba C P, & Breen T J (2008) "Phase I trial on the safety of topical rhVEGF on chronic neuropathic diabetic foot ulcers." J Wound Care 17(1):30-32, 34-37.

80 Robson M C, Phillips T J, Falanga V, Odenheimer D J, Parish L C, Jensen J L, & Steed D L (2001) "Randomized trial of topically applied repifermin (recombinant human keratinocyte growth factor-2) to accelerate wound healing in venous ulcers." Wound Repair Regen 9(5):347-352.

81 Robson M C, Phillips L G, Lawrence W T, Bishop J B, Youngerman J S, Hayward P G, Broemeling L D, & Heggers J P (1992) "The safety and effect of topically applied recombinant basic fibroblast growth factor on the healing of chronic pressure sores." Ann Surg 216(4):401-406; discussion 406-408.

82 Robson M C, Phillips L G, Thomason A, Robson L E, & Pierce G F (1992) "Platelet-derived growth factor BB for the treatment of chronic pressure ulcers." Lancet 339(8784):23-25.

83 Sullivan S R, Underwood R A, Gibran N S, Sigle R O, Usui M L, Carter W G, & Olerud J E (2004) "Validation of a model for the study of multiple wounds in the diabetic mouse (db/db)." Plast Reconstr Surg 113(3):953-960.

84 Davidson J M (1998) "Animal models for wound repair." Arch Dermatol Res 290 Suppl:S1-11.

85 Chan R K, Liu P H, Pietramaggiori G, Ibrahim S I, Hechtman H B, & Orgill D P (2006) "Effect of recombinant platelet-derived growth factor (Regranex) on wound closure in genetically diabetic mice." J Burn Care Res 27(2):202-205.

86 Galiano R D, Tepper O M, Pelo C R, Bhatt K A, Callaghan M, Bastidas N, Bunting S, Steinmetz H G, & Gurtner G C (2004) "Topical vascular endothelial growth factor accelerates diabetic wound healing through increased angiogenesis and by mobilizing and recruiting bone marrow-derived cells." Am J Pathol 164(6):1935-1947.

87 Hollinger J O, Hart C E, Hirsch S N, Lynch S, & Friedlaender G E (2008) "Recombinant human platelet-derived growth factor: biology and clinical applications." J Bone Joint Surg Am 90 Suppl 1:48-54.

88 Muschler G F, Raut V P, Patterson T E, Wenke J C, & Hollinger J O ("The design and use of animal models for translational research in bone tissue engineering and regenerative medicine." Tissue Eng Part B Rev 16(1): 123-145.

89 Hollinger J O & Kleinschmidt J C (1990) "The critical size defect as an experimental model to test bone repair materials." J Craniofac Surg 1(1):60-68.

90 Schmoekel H G, Weber F E, Schense J C, Gratz K W, Schawalder P, & Hubbell J A (2005) "Bone repair with a form of BMP-2 engineered for incorporation into fibrin cell ingrowth matrices." Biotechnol Bioeng 89(3):253-262.

91 Gautschi O P, Frey S P, & Zellweger R (2007) "Bone morphogenetic proteins in clinical applications." ANZ J Surg 77(8):626-631.

92 Jones L L, Oudega M, Bunge M B, & Tuszynski M H (2001) "Neurotrophic factors, cellular bridges and gene therapy for spinal cord injury." The Journal of physiology 533(Pt 1):83-89.

93 Andrews M R, Czvitkovich S, Dassie E, Vogelaar C F, Faissner A, Blits B, Gage F H, ffrench-Constant C, & Fawcett J W (2009) "Alpha9 integrin promotes neurite outgrowth on tenascin-C and enhances sensory axon regeneration." The Journal of neuroscience: the official journal of the Society for Neuroscience 29(17):5546-5557.

94 Tysseling-Mattiace V M, Sahni V, Niece K L, Birch D, Czeisler C, Fehlings M G, Stupp S I, & Kessler J A (2008) "Self-assembling nanofibers inhibit glial scar formation and promote axon elongation after spinal cord injury." The Journal of neuroscience: the official journal of the Society for Neuroscience 28(14):3814-3823.

95 Sharp J, Frame J, Siegenthaler M, Nistor G, & Keirstead H S (2010) "Human embryonic stem cell-derived oligodendrocyte progenitor cell transplants improve recovery after cervical spinal cord injury." Stem cells 28(1):152-163.

All references, patents, patent applications, publications, and articles set forth herein are hereby incorporated by reference herein for all purposes; in case of conflict, the instant specification controls.

Further Disclosure

1. An isolated polypeptide comprising a heparin binding peptide having at least 85% homology to at least a portion of a Tenascin (TNC) III1-5 domain or a TNC III5 domain, or at least a portion of a fibrinogen β15-66 domain. 2. The polypeptide of 1 wherein the heparin binding peptide comprises at least a portion of a Tenascin III3-5 domain. 3. The polypeptide of 1 wherein the heparin binding peptide comprises at least a portion of a fibrinogen β15-66 domain. 4. The polypeptide of any of 1-3 wherein the heparin binding peptide binds to at least twenty (alternatively at least 5) of the growth factors or growth factor-binding proteins, e.g., as chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF. 5. A biomaterial comprising any of 1-4. Or a compound comprising any of 1-4 specifically bound to a cytokine in a molecular complex. 6. A polymer comprising a polypeptide of 1. The synthetic polymer of 6 comprising a polysaccharide, polyethylene glycol, polyalkylene oxide, collagen, or gelatin. 7. The polymer of 6 or 7 wherein the polymer further comprises a transglutaminase (TG) substrate. 8. The polymer of any of 6-7 further comprising a cytokine, with the cytokine being specifically bound by the heparin binding peptide. 9. A solution comprising any of 1-7. For example: a cell culture supplement or a cell culture medium. 10. The solution of 8 further comprising a cytokine specifically bound to a heparin binding domain. 11. A biomaterial scaffold comprising a polymeric matrix that comprises the polypeptide or the biomaterial of 1-10. 12. A surface comprising one or more immobilized moieties of any of 1-11. 13. The surface of 12 being chosen from the group consisting of a medical device, a stent, a vascular graft, a cell culture surface, a cell culture vessel, a cell carrier, tissue culture plastic, an affinity column, and a cell separations device.

14. An isolated synthetic heparin binding peptide having at least 85% homology to SEQ ID NO:9 or at least 85% homology to SEQ ID NO:8. 15. The peptide of 14 wherein the homology is at least about 95%. 16. A molecular fusion comprising a bioactive agent and a heparin binding peptide of 14 or 15. 17. A biomaterial scaffold comprising a polypeptide or molecular fusion of any of 14-16. 18. The peptide, molecular fusion or scaffold of any of 1-4 wherein the heparin binding peptide comprises SEQ ID NO:9 or SEQ ID NO:8; or wherein the heparin binding peptide of SEQ ID NO: 8 is truncated at one or both ends and comprises a subsequence of 45 residues of SEQ ID NO:8; or wherein the heparin binding peptide of SEQ ID NO: 9 is truncated at one or both ends and comprises a subsequence of 410 residues of SEQ ID NO:9; or wherein the heparin binding peptide binds to at least five of growth factors or growth factor-binding proteins, e.g., those chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF.

19. The peptide, molecular fusion or scaffold of any of 14-18 being a fusion protein; or further comprising a transglutaminase (TG) substrate; or wherein the TG substrate comprises residues 1-8 of alpha2-plasmin inhibitor; or further comprising a cell adhesion moiety having a specific binding affinity for a cell adhesion molecule, e.g., the cell adhesion moiety comprises a ligand for a glycoprotein or a cell surface receptor, or, e.g., the cell adhesion moiety is a cell surface receptor selected from the group consisting of an integrin and a cadherin, or, e.g., the cell adhesion moiety comprises an integrin-binding peptide chosen from the group consisting of Tenascin III3 and an RGD sequence.

20. The peptide, molecular fusion or scaffold of any of 14-20 further comprising a fibronectin III9 domain, fibronectin III9* domain, fibronectin III9-10 domain, or a fibronectin III9*-10 domain; or further comprising a fibronectin III9-10 domain and a heparin binding domain sequence taken from a domain chosen from the group consisting of TNC III1-5, TNCIII3-5, and TNC III5; or further comprising a fibronectin III9*-10 domain and a HBD sequence taken from a domain chosen from the group consisting of TNC III1-5, TNCIII3-5, and TNC III5.

21. A biomaterial comprising the peptide, molecular fusion or scaffold of any of 14-20.

22. A compound comprising the peptide, molecular fusion or scaffold of any of 14-21 specifically bound to a cytokine in a molecular complex, e.g., cytokine being selected from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF.

23. A polymer comprising the polypeptide or molecular fusion of any of 14-22. 24. The polymer of 10 comprising a polysaccharide, a polyethylene glycol, a polyalkylene oxide, a collagen, or a gelatin.

25. A biomaterial scaffold of any of 14-24 comprising a polypeptide that comprises a plurality of heparin binding peptides having at least 85% homology to a Tenascin (TNC) III1-5 domain (SEQ ID NO:9) or a fibrinogen β15-66 domain (SEQ ID NO:8). 26. The biomaterial scaffold of claim 12 comprising at least three cytokines specifically bound to the plurality of heparin binding peptides, with each of the three cytokines filling at least about 5% of the heparin binding peptides present in the scaffold; or wherein the polypeptide further comprises a transglutaminase substrate, with the polypeptide being covalently linked by a transglutaminase-mediated chemical reaction that covalently links the substrate to the matrix, or comprising copolymers that comprise a transglutaminase substrate, with the copolymers being covalently linked to each other with bonds formed by a transglutaminase enzyme, e.g., wherein the copolymers comprise a hydrophilic polymer. 27. The biomaterial scaffold of claim 25 further comprising at least three cytokines specifically bound to the heparin binding peptides, with each of the three cytokines filling at least about 5% of the HBDs present in the matrix. 28. The biomaterial scaffold of 25 or 27 wherein the cytokines are chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, and HGF, or the cytokines are IGF-1 bound via IGF-BP3 or IGF-BP5. 29. The biomaterial scaffold of any of 25-28 providing a sterile and pharmaceutically acceptable tissue repair matrix. 30. The biomaterial scaffold of any of 25-28 comprising one or more of VEGF-A165, PDGF-BB, BMP-2, NT-3, and BDNF.

31. A composition that blocks specific binding to a heparin binding domain (HBD), the composition comprising an antibody, antibody fragment, scFv, or aptamer that specifically binds the HBD, with the HBD being chosen from the group consisting of a Tenascin (TNC) III1-5 domain, a TNC III5 domain, and a fibrinogen β15-66 domain. 32. The composition of 18 wherein the HBD comprises the TNCIII5. 33. The composition of 31 wherein the HBD comprises the a fibrinogen β15-66 domain. 34. The composition of any of 31-33 wherein the composition comprises the antibody, the antibody fragment, or the scFv. 35. The composition of any of 31-34 wherein the composition comprises the antibody, the antibody fragment, or the scFv, said antibody, antibody fragment, or scFv being a humanized antibody or comprising a portion of a humanized antibody. 36. The composition of any of 31-35 wherein the composition blocks binding of the HBD to one or more cytokines or cytokine-binding proteins, e.g., chosen from the group consisting of FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF. 37. The composition of any of 31-36 in a pharmaceutically acceptable formulation. 38. A medicament for treating a cancer comprising the composition of any of 31-37.

39. A surface of an object of a cell surface comprising one or more immobilized moieties chosen from the group consisting of a peptide with at least about 85% homology to a Tenascin (TNC) III1-5 domain, a peptide with at least about 85% homology to a TNC III5 domain, a peptide with at least about 85% homology to a fibrinogen β15-66 domain, a peptide with at least about 85% homology to a fibronectin III9 domain, a peptide with at least about 85% homology to a fibronectin III9* domain, a peptide with at least about 85% homology to a fibronectin III9-10 domain, and a peptide with at least about 85% homology to a fibronectin III9*-10 domain. 40. The surface of claim 39 being chosen from the group consisting of a medical device, a stent, a vascular graft, a cell culture surface, a cell culture vessel, a cell carrier, tissue culture plastic, an affinity column, and a cell separations device. 41. The surface of claim 39 or 40 comprising one or more cytokines specifically bound to a heparin binding domain portion of: the TNC III1-5 domain, the TNC III5 domain, or the β15-66 domain. 42. The surface of claim 41 comprising at least three of the cytokines specifically bound to an HBD, with each of the three cytokines filling at least about 5% of the HBDs present in the scaffold. 43. The surface of claim 41 or 42 wherein the cytokines are chosen from the group consisting of, e.g., FGF-2, FGF-4, FGF-6, FGF-7, FGF-10, FGF-17, FGF-18, TGF-β1, TGF-β2, NT-3, BDNF, PlGF-2, PlGF-3, BMP-2, PDGF-AA, PDGF-AB, PDGF-BB, PDGF-DD, VEGF-A165, VEGF-B, VEGF-C, IGF-BP3, IGF-BP5, and HGF. 42. The surface of any of claims 37-40 wherein the moieties are adsorbed or covalently bound. 43. The surface of claim 37 being the cell surface.

44. A use of the molecular fusion, the biomaterial, the compound, the polymer, the scaffold, the composition, the peptide, or the surface of any of 1-43 for treatment of a tissue. 45. The use of 44, with the tissue being a skin tissue, nerve tissue, or bone tissue.

45. A use of the molecular fusion, the biomaterial, the compound, the polymer, the scaffold, the composition, the peptide, or the surface of any of 1-43 for preparation of a medicament for treating a patient. 47. The use of 45 wherein the medicament is for use in a treatment of cancer or treatment of a tissue.

The invention claimed is:

1. A biomaterial scaffold comprising a biomaterial matrix that comprises a synthetic polypeptide that comprises SEQ ID NO:8 or SEQ ID NO:9, with the biomaterial scaffold being pharmaceutically acceptable and free of fibrin.

2. The biomaterial scaffold of claim 1 comprising a plurality of said synthetic polypeptides and at least three cytokines being different types of cytokines relative to each other and collectively specifically bound to the plurality of synthetic polypeptides, with each of the three cytokines filling at least about 5% of the synthetic polypeptides present in the scaffold.

3. The biomaterial scaffold of claim 1 wherein the polypeptide further comprises a transglutaminase substrate, with the polypeptide being covalently linked by a transglutaminase-mediated chemical reaction that covalently links the substrate to the scaffold.

4. The biomaterial scaffold of claims 1 further comprising a cytokine specifically bound to the polypeptide, wherein the cytokine is chosen from the group consisting of fibroblast growth factor-2 (FGF-2), fibroblast growth factor-4 (FGF-4), fibroblast growth factor-6 (FGF-6), fibroblast growth factor-7 (FGF-7), fibroblast growth factor-10 (FGF-10), fibroblast growth factor-17 (FGF-17), fibroblast growth factor-18 (FGF-18), transforming growth factor-β1 (TGF-β1), transforming growth factor-β2 (TGF-β2), neurotrophin-3 (NT-3), brain-derived neurotrophic factor (BDNF), placental growth factor-2 (PlGF-2), placental growth factor-3 (PlGF-3), bone morphogenetic protein-2 (BMP-2), platelet derived growth factor AA (PDGF-AA), platelet derived growth factor AB (PDGF-AB), platelet derived growth factor BB (PDGF-BB), platelet derived growth factor DD (PDGF-DD), vascular endothelial growth factor-A165 (VEGF-A165), vascular endothelial growth factor-B (VEGF-B), vascular endothelial growth factor-C (VEGF-C), hepatocyte growth factor (HGF), fibroblast growth factor-5 (FGF-5), and bone morphogenetic protein-2/7 (BMP-2/7) or IGF-1 bound via insulin-like growth factor-binding protein-3 (IGF-BP3) or insulin-like growth factor-binding protein-5 (IGF-BP5), with the IGF-BP3 or IGF-BP5 being specifically bound to the polypeptide.

5. The biomaterial scaffold of claim 1 being a sterile and pharmaceutically acceptable tissue repair matrix.

6. The biomaterial scaffold of claim 1 comprising one or more of VEGF-A165, PDGF-BB, BMP-2, NT-3, and BDNF.

7. The biomaterial scaffold of claim 1 wherein the peptide consists of SEQ ID NO:8 or SEQ ID NO:9.

8. A surface that is free of fibrin and free of fibrinogen comprising one or more immobilized moieties chosen from the group consisting of a synthetic peptide that comprises SEQ ID NO:8 or SEQ ID NO:9 the surface being chosen from the group consisting of a stent, a vascular graft, a cell culture surface, a cell culture vessel, a cell carrier, and tissue culture plastic; said moieties being immobilized to the surface.

9. The surface of claim 8 being a surface of a medical device.

10. The surface of claim 8 comprising one or more cytokines specifically bound to a domain selected from the group consisting of the TNC III1-5 domain and the β15-66 domain.

11. The surface of claim 8 further comprising at least three different cytokines specifically bound to at least about 5% of the peptides immobilized on the surface.

12. The surface of claim 8 wherein one or more cytokines are specifically bound to the peptide.

13. The surface of claim 8 further comprising a cytokine specifically bound to the peptide, wherein the cytokine is selected from the group consisting of fibroblast growth factor-2 (FGF-2), fibroblast growth factor-4 (FGF-4), fibroblast growth factor-6 (FGF-6), fibroblast growth factor-7 (FGF-7), fibroblast growth factor-10 (FGF-10), fibroblast growth factor-17 (FGF-17), fibroblast growth factor-18 (FGF-18), transforming growth factor-β1 (TGF-β1), transforming growth factor-β2 (TGF-β2), neurotrophin-3 (NT-3), brain-derived neurotrophic factor (BDNF), placental growth factor-2 (PlGF-2), placental growth factor-3 (PlGF-3), bone morphogenetic protein-2 (BMP-2), platelet derived growth factor AA (PDGF-AA), platelet derived growth factor AB (PDGF-AB), platelet derived growth factor BB (PDGF-BB), platelet derived growth factor DD (PDGF-DD), vascular endothelial growth factor-A165 (VEGF-A165), vascular endothelial growth factor-B (VEGF-B), and vascular endothelial growth factor-C (VEGF-C), or one or more cytokine-binding factors are specifically bound to the peptide, the cytokine-binding factors being selected from the group consisting of insulin-like growth factor-binding protein-3 (IGF-BP3) and insulin-like growth factor-binding protein-5 (IGF-BP5).

14. The surface of claim 8 wherein the peptide has identity to SEQ ID NO:8 or SEQ ID NO:9.

* * * * *